(12) United States Patent
Jones et al.

(10) Patent No.: US 11,536,719 B2
(45) Date of Patent: Dec. 27, 2022

(54) MOLECULAR NANOTAGS

(71) Applicant: The United States of America, as represented by the Secretary, Dept of Health & Human Services, Bethesda, MD (US)

(72) Inventors: Jennifer C. Jones, Bethesda, MD (US); Aizea Morales-Kastresana, Washington, DC (US); Jay A. Berzofsky, Bethesda, MD (US); Joshua Welsh, North Bethesda, MD (US); Ari Rosner, Edgewater, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 373 days.

(21) Appl. No.: 16/342,345

(22) PCT Filed: Oct. 23, 2017

(86) PCT No.: PCT/US2017/057928
§ 371 (c)(1),
(2) Date: Apr. 16, 2019

(87) PCT Pub. No.: WO2018/076025
PCT Pub. Date: Apr. 26, 2018

(65) Prior Publication Data
US 2019/0242887 A1    Aug. 8, 2019

Related U.S. Application Data

(60) Provisional application No. 62/411,324, filed on Oct. 21, 2016.

(51) Int. Cl.
*G01N 33/543* (2006.01)
*C12Q 1/6834* (2018.01)
(Continued)

(52) U.S. Cl.
CPC ........ *G01N 33/54346* (2013.01); *B82Y 15/00* (2013.01); *C12Q 1/6834* (2013.01);
(Continued)

(58) Field of Classification Search
None
See application file for complete search history.

(56) References Cited

U.S. PATENT DOCUMENTS 5,123,731 A    6/1992  Yoshinaga et al.
7,800,754 B2   9/2010  Kenyon
(Continued)

FOREIGN PATENT DOCUMENTS

CN    1282378       1/2001
CN    101493455 A   7/2009
(Continued)

OTHER PUBLICATIONS

Zhu, S. et al. Light-Scattering Detection below the Level of Single Fluorescent Molecules for High-Resolution Characterization of Functional Nanoparticles, ACS NANO vol. 8(10), pp. 10998-11006 (Year: 2014).*

(Continued)

*Primary Examiner* — Xiaoyun R Xu
(74) *Attorney, Agent, or Firm* — Klarquist Sparkman, LLP

(57) ABSTRACT

A molecular nanotag is disclosed that includes a core nanoparticle with a diameter of less than about 100 nm, with an optional shell surrounding the core, and an armor bound to the surface of the core nanoparticle, or if present, to the surface of the shell. The molecular nanotag also includes a functionalized end with a fixed number of binding sites that can selectively bind to a molecular targeting ligand. Any one of, or any combination of, the core, the shell and the armor contribute to fluorescence, light scattering and/or ligand (Continued)

binding properties of the molecular tag that are detectable by microscopy or in a devices that measures intensity or power of fluorescence and light scattering. The light scattering intensity or power of the assembled structure is detectable above the specific level of the reference noise of a device detecting the light scattering intensity or power, its fluorescence intensity or power has sufficient brightness for detection above the limit of detection for the instrument, and ligand specificity is conferred by the ligand binding component. Methods of biomarker and biosignature detection using the molecular tags are also disclosed.

22 Claims, 29 Drawing Sheets

Specification includes a Sequence Listing.

(51) Int. Cl.
  *B82Y 15/00* (2011.01)
  *G01N 15/14* (2006.01)
  *G01N 21/64* (2006.01)
  G01N 33/574 (2006.01)
  G01N 21/47 (2006.01)

(52) U.S. Cl.
  CPC ..... *G01N 15/1436* (2013.01); *G01N 15/1459* (2013.01); *G01N 15/1484* (2013.01); *G01N 21/6428* (2013.01); *G01N 33/54353* (2013.01); *G01N 33/57434* (2013.01); *G01N 2015/149* (2013.01); *G01N 2021/4707* (2013.01); *G01N 2021/4726* (2013.01)

(56) References Cited

U.S. PATENT DOCUMENTS

| | | | |
|---|---|---|---|
| 8,467,055 | B2 | 6/2013 | Imanishi et al. |
| 8,637,082 | B2 | 1/2014 | Tulsky et al. |
| 8,907,312 | B2 | 12/2014 | Heng et al. |
| 9,442,106 | B2 | 9/2016 | Beck et al. |
| 9,726,609 | B2 | 8/2017 | Natan et al. |
| 9,739,700 | B2 | 8/2017 | Yan et al. |
| 2005/0141843 | A1 | 6/2005 | Warden et al. |
| 2005/0225745 | A1 | 10/2005 | Nagai |
| 2009/0002699 | A1 | 1/2009 | Sutherland et al. |
| 2010/0035243 | A1 | 2/2010 | Muller et al. |
| 2010/0220315 | A1 | 9/2010 | Morrell et al. |
| 2012/0001090 | A1 | 1/2012 | Takasaki et al. |
| 2013/0095575 | A1 | 4/2013 | Jones et al. |
| 2013/0123145 | A1 | 5/2013 | Chakravarthy et al. |
| 2014/0030193 | A1 | 1/2014 | Searson et al. |
| 2014/0228233 | A1 | 8/2014 | Pawlowski et al. |
| 2015/0004598 | A1 | 1/2015 | Gao et al. |
| 2015/0166997 | A1 | 6/2015 | Messmer |
| 2016/0216252 | A1 | 7/2016 | Zhang et al. |
| 2020/0278285 | A1 | 9/2020 | Berzofsky et al. |

FOREIGN PATENT DOCUMENTS

| | | |
|---|---|---|
| CN | 101679022 | 3/2010 |
| CN | 101784886 A | 7/2010 |
| CN | 102998288 A | 3/2013 |
| CN | 103364353 A | 10/2013 |
| CN | 102713612 B | 10/2016 |
| JP | 2009-085840 | 4/2003 |
| JP | 2005-532456 | 10/2005 |
| JP | 2012-023964 | 2/2012 |
| WO | WO 2008/122035 A1 | 10/2008 |
| WO | WO 2010/099118 A1 | 9/2010 |
| WO | WO 2011/119589 A1 | 9/2011 |
| WO | WO 2015/123005 A1 | 8/2015 |
| WO | WO 2016/011383 A1 | 1/2016 |
| WO | WO 2017/072360 A1 | 5/2017 |
| WO | WO 2019/084022 A1 | 5/2019 |

OTHER PUBLICATIONS

Liu, H. Y., et al. Engineering Monovalent Quantum Dot-Antibody Bioconjugates with a Hybrid Gel System, Bioconjugate Chemistry, 22, pp. 510-517 (Year: 2012).*
Gregori, G. et al. Hyperspectral Cytometry at the Single-Cell Level Using a 32-Channel Photodetector, Cytometry Part A, 81A, pp. 35-44 (Year: 2012).*
CN 101493455, English Abstract provided.
CN 101784886, US 2009/0002699 A1 & English Abstract provided.
CN 102998288, English Abstract provided.
CN 103364353, English Abstract provided.
Arakelyan et al., "Nanoparticle-based flow virometry for the analysis of individual virions," *J Clin Invest.* 123:3716-3727, 2013.
Are Quantum Dots Any Good for Flow Cytometry: http://bitesizebio.com/33830/quantum-dots-good-flow-cytometry/ (2017).
Crow et al. "Plasmonic Flow Cytometry by Immunolabeled Nanorods" *Cytometry Part A* 79A:57-65, 2011.
Erdbrügger et al., "Imaging Flow Cytometry Elucidates Limitations of Microparticle Analysis by Conventional Flow Cytometry" *Cytometry A* 85:756-770, 2014.
Farlow et al., "Exclusive formation of monovalent quantum dot imaging probes by steric exclusion" *Nat Methods* 10:1203-1205, 2013.
Gallina et al., "Aptamer-conjugated, fluorescent gold nanorods as potential cancer theradiagnostic agents," *Mat Sci Eng. C* 59:324-332, 2015.
Gardiner et al., "Measurement of refractive index by nanoparticle tracking analysis reveals heterogeneity in extracellular vesicles," *J Extracell Vesicles* 3:25361, 2014.
Gaudin and Barteneva, "Sorting of small infectious virus particles by flow virometry reveals distinct infectivity profiles" *Nat Comm.* 6:6022, 2015.
Gold Nanoparticles for Flow Cytometry (70nm-400nm): http://www.cytodiagnostics.com/store/pc/Gold-Nanoparticles-for-Flow-Cytometry-70nm-400nm-c237.htm (dowloaded Apr. 11, 2019).
Hollingsworth et al. "Giant multishell CdSe nanocrystal quantum dots with suppressed blinking: Novel fluorescent probes for real-time detection of single-molecule events" *Proc SPIE* 7189-718904, 2009.
Introduction to flow cytometry: http://www.abcam.com/protocols/introduction-to-flow-cytometry (downloaded Apr. 11, 2019).
Kaganman "Quantum dots go with the flow" *Nature Methods* 3:662-663 (2006).
Kormelink et al. "Prerequisites for the Analysis and Sorting of Extracellular Vesicle Subpopulations by High-Resolution Flow Cytometry" *Cytometry Part A* 89A:135-147, 2016 (first published Feb. 16, 2015).
Liu and Gao "Engineering Monovalent Quantum Dot—Antibody Bioconjugates with a Hybrid Gel System" *Bioconjuage Chemistry* 22:510-517, 2011.
Morales-Kastresana et al., "Labeling Extracellular Vesicles for Nanoscale Flow Cytometry," *Scientific Reports* 7:1878, 2017.
Qdot® 655 ITK™ Amino (PEG) Quantum Dots, Catalog No. Q21521M, Thermo Fisher Scientific Inc., 2015.
Seo et al. "Production and Targeting of Monovalent Quantum Dots" *J. Vis. Exp.* 92:e52198, 2014.
SNAP-tag® Technologies: Novel Tools to Study Protein Function, New England BioLabs Inc., from NEB expressions Fall 2008, vol. 3.3 by Kai Johnsson, Ph.D., Ecole Polytechnique Fédérale de Lausanne.
Tanev et al. "Flow Cytometry with Gold Nanoparticles and their Clusters as scattering Contrast Agents: FDTD Simulation of Light-Cell Interaction" *J. Biophotonics.* 2:505-520, 2009.
Uddayasankar et al. "Isolation of Monovalent Quantum Dot—Nucleic Acid Conjugates Using Magnetic Beads" *Bioconj Chem.* 25:1342-1350, 2014.

(56) References Cited

OTHER PUBLICATIONS van der Pol et al., "Optical and non-optical methods for detection and characterization of microparticles and exosomes" *J Thromb Haaemost.* 8:2596-2607, 2010.
van der Pol et al., "Single vs. swarm detection of microparticles and exosomes by flow cytometry" *J Thromb Haemost.* 10:919-930, 2012.
van der Vlist et al. "Fluorescent labeling of nano-sized vesicles released by cells and subsequent quantitative and qualitative analysis by high-resolution flow cytometry" *Nature Protocols* 7:1311-1326, 2012.
Vela et al., "Effect of shell thickness and composition on blinking suppression and the blinking mechanism in 'giant' CdSe/CdS nanocrystal quantum dots" *J. Biophotonics.* 3:706-717, 2010.
Verma et al., "Extracellular vesicles: potential applications in cancer diagnosis, prognosis, and epidemiology," *BMC Clin Pathol.* 15.6, 2015.
Welsh et al., "Prospective Use of High-Refractive Index Materials for Single Molecule Detection in Flow Cytometry," *Sensors* 18:2461, 2018, with Supplementary Materials.
Yang et al., "Development of an Ultrasensitive Dual-Channel Flow Cytometer for the Individual Analysis of Nanosized Particles and Biomolecules," *Anal Chem.* 81:2555-2563, 2009.
Zhou et al., "Tandem Phosphorothioate Modifications for DNA Adsorption Strength and Polarity Control on Gold Nanoparticles," *ACS Appl Mater. Interfaces* 6:14795-14800, 2014.
Zhu et al., "Light-scattering detection below the level of single fluorescent molecules for high-resolution characterization of functional nanoparticles," *ACS Nano* 8:10998-11006, 2014.
Zucker et al. "Characterization, Detection, and Counting of Metal Nanoparticles Using Flow Cytometry" *Cytometry Part A* 89A:169-183, 2016.
Written Opinion and International Search Report dated Mar. 27, 2018 for PCT/US2017/057928 (13 pages).
"Performance Testing of CytoFLEX Flow Cytometer," Beckman Coulter, Inc. for News-Medical.Net, Apr. 8, 2015. available at www.newsmedical.net. (7 pages).
Catalog for SpheroTM Rainbow Calibration Particles, 2010-2011, Spherotech, Inc., available at www.spherotech.com. pp. 20-29.
De Rond et al., "Deriving extracellular vesicle size from scatter intensities measured by flow cytometry," *Current Protocols in Cytometry*, e43, doi: 10.1002/cpcy.43, 2018.
Product literature for Cell Sorting Setup Beads, Catalog Nos. C16506, C16507, C16508, C16509, Life Technologies Corporation, available at www.lifetechnologies.com. 4 pages. 2013.
Product literature for Flow Cytometry Size Calibration Kit, Catalog No. F-13838, Molecular Probes, Inc, available at https://assets.thermofisher.com/TFS-Assets/LSG/manuals/mp13838.pdf. 2 pages. 2003.
Product literature for Flow Cytometry Sub-Micron Particle Size Reference Kit, Catalog No. F13839, Molecular Probes, Inc, available at https://assets.thermofisher.com/TFS-Assets/LSG/manuals/mp13839.pdf. 4 pages. 2014.
Supplemental information for Van der Pol et al., "Standardization of extracellular vesicle measurements by flow cytometry through vesicle diameter approximation," Journal of Thrombosis and Haemostasis, vol. 16, No. 6, 1236-1245 (Mar. 25, 2018).

Van Der Pol et al., "Particle size distribution of exosomes and microvesicles determined by transmission electron microscopy, flow cytometry, nanoparticle tracking analysis, and resistive pulse sensing," *Journal of Thrombosis and Haemostasis* 12:1182-1192, 2014.
Van der Pol et al., "Refractive Index Determination of Nanoparticles in Suspension Using Nanoparticle Tracking Analysis," *Nano Letters* 14:6195-6201, 2014.
Van der Pol et al., "Absolute sizing and label-free identification of extracellular vesicles by flow cytometry," *Nanomedicine: Nanotechnology, Biology and Medicine* 14:801-810, 2018.
Van der Pol et al., "Standardization of extracellular vesicle measurements by flow cytometry through vesicle diameter approximation," *Journal of Thrombosis and Haemostasis* 16:1236-1245, 2018.
Wang et al., "Standardization, calibration, and control in flow cytometry," *Current Protocols in Cytometry* 79:1-27, 2017.
Welsh et al., "FCM$_{PASS}$ Software Aids Extracellular Vesicle Light Scatter Standardization," Cytometry, Part A, 1-13, 2019.
International Search Report and Written Opinion for related International Application No. PCT/US2018/057128, dated Feb. 22, 2019, 11 pages.
Andor, "Spectral Flow Cytometry," https://www.oxinst.com/learning/view/article/an-introduction-to-spectral-flow-cytometry, downloaded May 17, 2019.
Exometry BV, Rosetta Calibration Overview, downloaded May 17, 2019.
Welsh, Joshua A., "FCM Pass," Software Overview, v1, downloaded May 17, 2019.
Welsh, Joshua A., "FCM Pass," Software Overview, v2, downloaded May 17, 2019.
Welsh, Joshua A., "Flow Cytometer Optimisation & Standardisation for the Study of Extracellular Vesicles as Translational Biomarkers," Thesis for the degree of Doctor of Philosophy, University of Southampton, Sep. 2016.
PCT/US2018/057128 International Search Report and Written Opinion dated Feb. 22, 2019 (13 pages).
Examination Report for related Australian Application No. 2017345814, 4 pages, dated Sep. 10, 2021.
Kumar et al., "Assembling gold nanoparticles in solution using phosphorothioate DNA as structural interconnects," *Current Science*, 84(1):71-74 (Jan. 2003).
Lee et al., "Reversible Aptamer—Au Plasmon Rulers for Secreted Single Molecules," *Nano Letters*, 15(7):4564-4570 (Jun. 2015).
Notice of Reasons for Refusal for related Japanese Application No. 2019-521089, 13 pages, dated Oct. 5, 2021.
Office Action for related European Application No. 17809073.4, 6 pages, dated Oct. 8, 2021.
Office Action for related Chinese Application No. 201780079138.7, 30 pages, dated Jan. 19, 2022.
Liu et al., "Precise organization of metal nanoparticles on DNA origami template", *Methods*, 67:205-214 (May 15, 2014).
Nakano, "DNA Immobilization and Its Application to Gene Sensors," *Hyomen Kagaku*, 25(12):744-751 (Sep. 6, 2004).
Notice of Reasons for Refusal for related Japanese Application No. 2019-521089, 9 pages, dated Aug. 30, 2022.
Zhou et al., "Tandem Phosphorothioate Modifications for DNA Adsorption Strength and Polarity Control on Gold Nanoparticles," Applied Materials & Interfaces, 6(17):14795-14800 (Aug. 22, 2014).

\* cited by examiner

1 Qdot resolution => 1 Molecule Detection with nanoFACS

FIG. 1A

High Refractive Index Allows Single Nanoparticle Resolution & Counting

→ Because single particle can be resolved with *scattered* (SSc) and/or fluorescent light with NanoFACS, a monovalent particle can be used for ligand enumeration Typical Qdot or other Hi-RI *Nanomaterial*

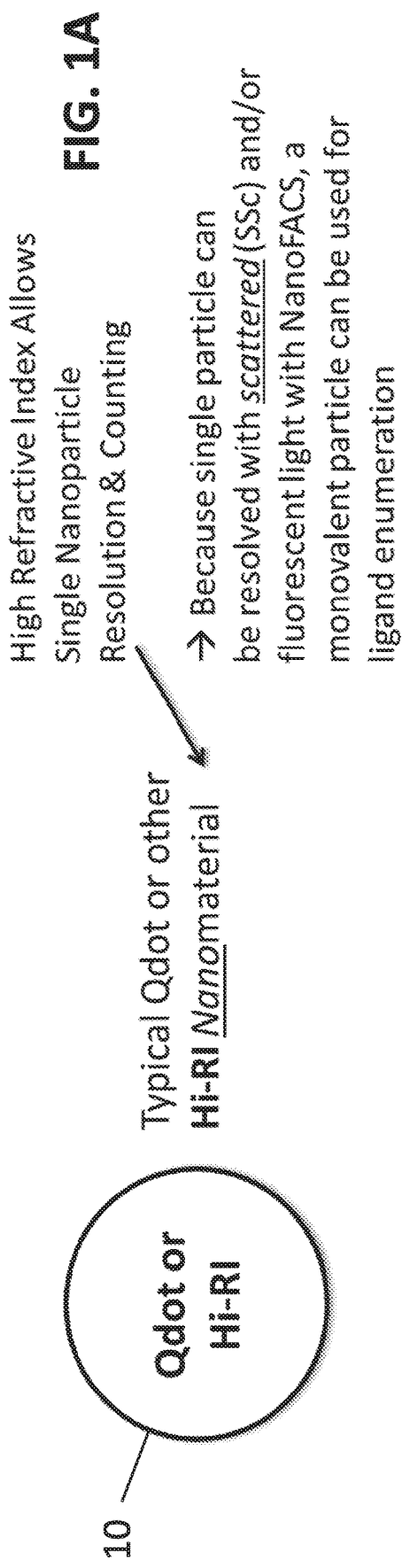

Monovalent "Armored" Qdot with Thiolated Single-strand DNA Armor. Using single functionalized DNA end (LOCK to bind KEY):

Customized Ligand "LOCK-KEY"

| LOCK | KEY (Examples) |
|---|---|
| Benzylguanine | SNAP-Tag |
| Biotin | (divalent SA)-Biotin |
| Oligo | anti-oligo for RNA:Aptamer |
| DCFPyL | PSMA (Prostate Specific Membrane Antigen) |

^small molecule with high PSMA affinity and specificity

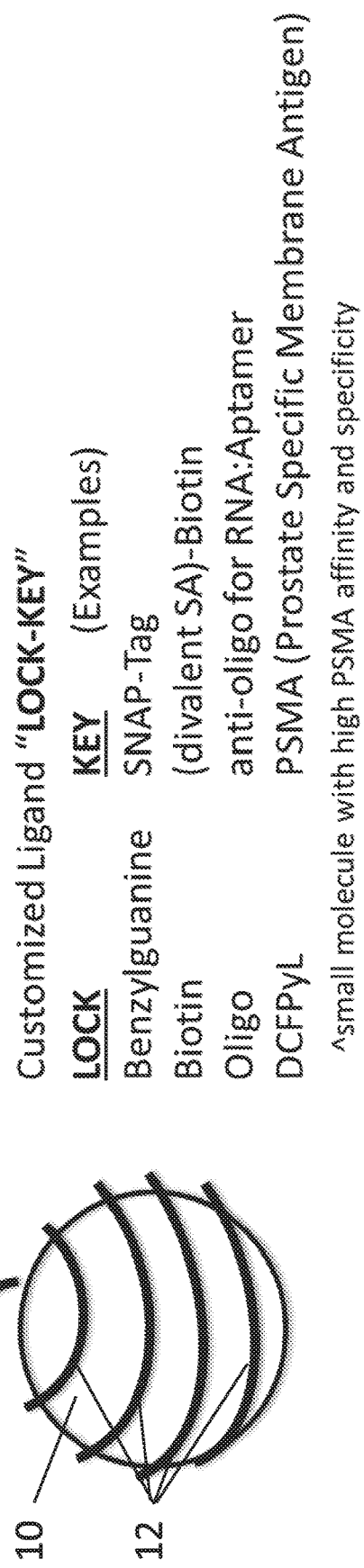

FIG. 1B
Monovalent "Armored" Qdot with Thiolated Single-strand DNA Armor. Using single functionalized DNA end LOCK (to bind KEY).
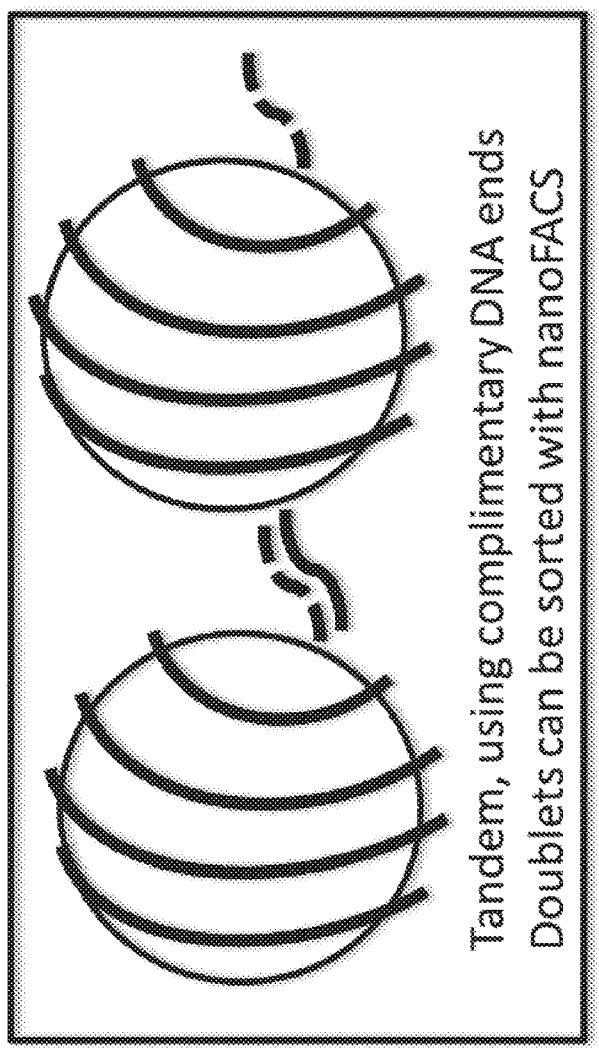
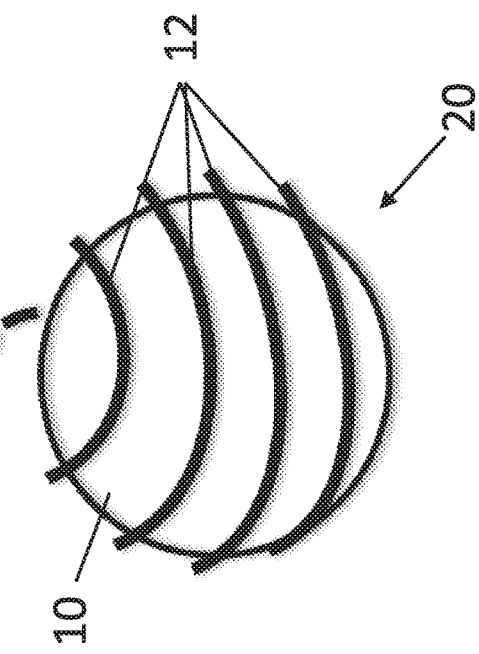

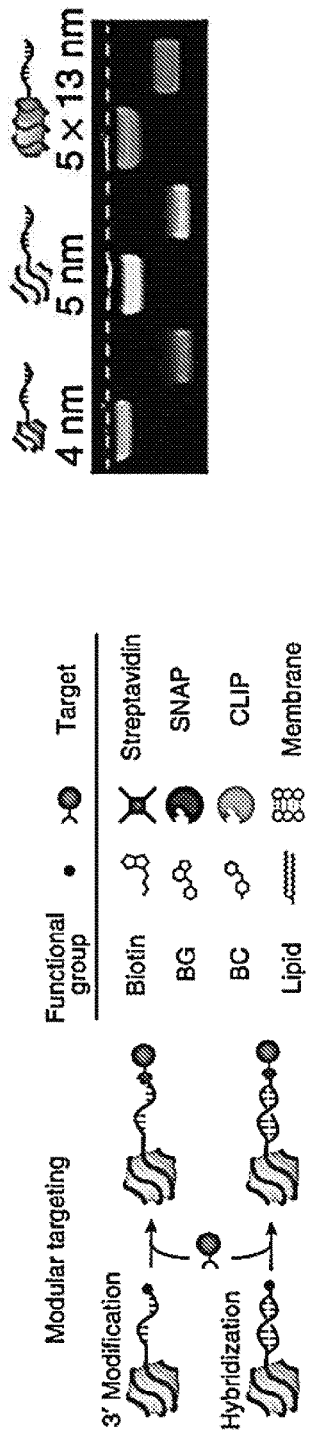
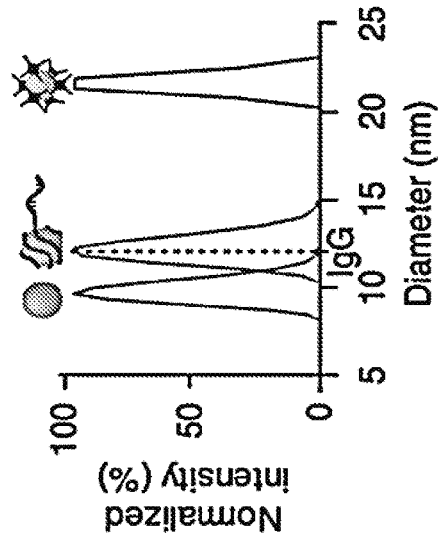
FIG. 1C
Size of Fowler Qdots: "As measured using dynamic light scattering, the hydrodynamic diameter of mQDs that emit at 605 nm was narrowly distributed around 12 nm, only 2 nm greater than that of bare particles (Fig. 1e)."
N.B. – measures of DLS (dynamic light scatter) intensity are not at all the same as scattered light intensity measured with flow cytometry

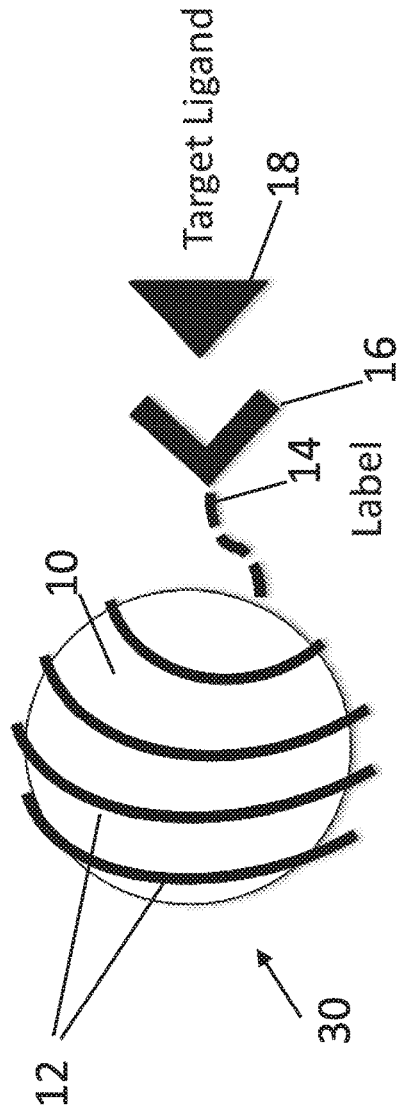
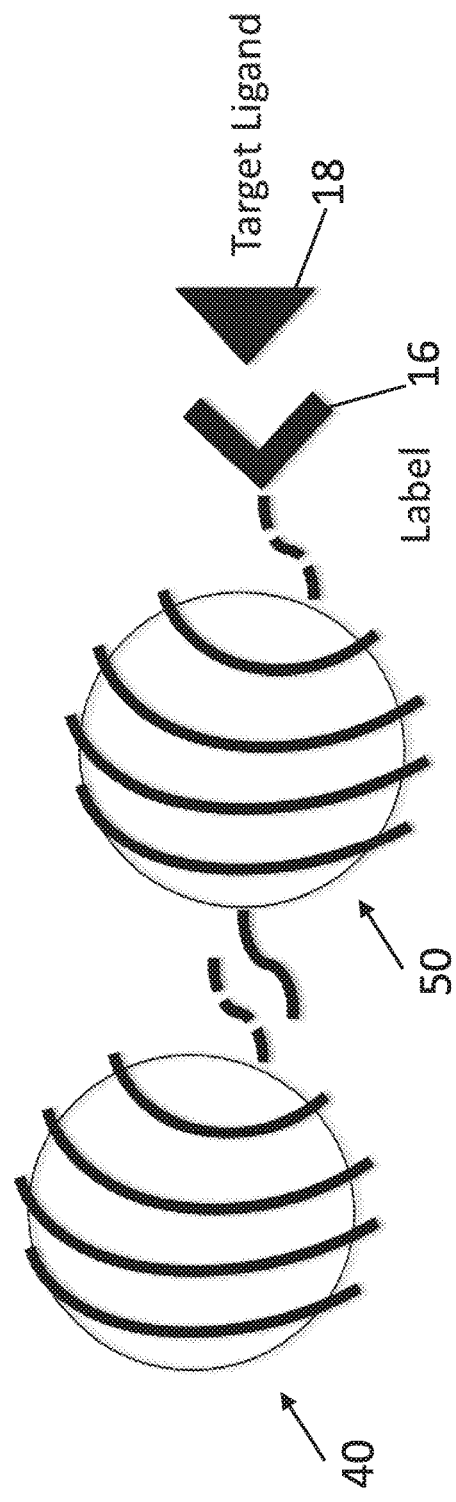
FIG. 1D

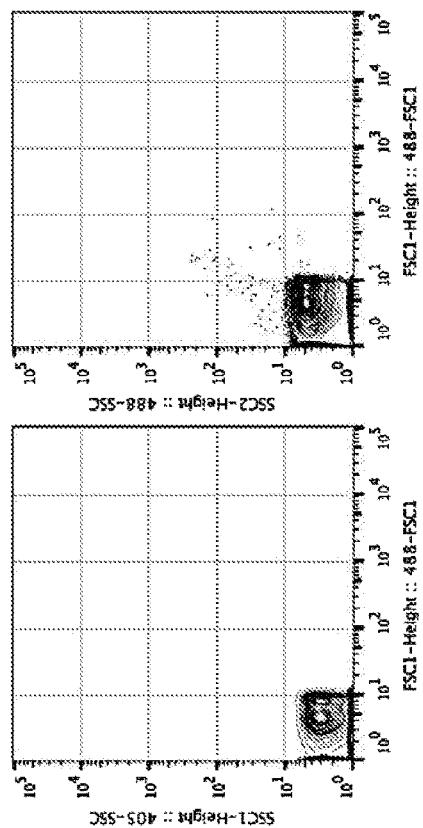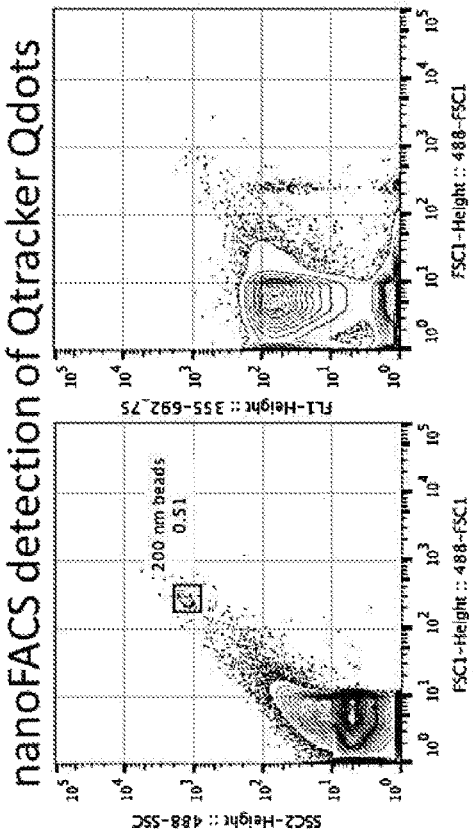
FIG. 4

FIG. 5
Expression of PSMA on EVs derived from prostate lines:
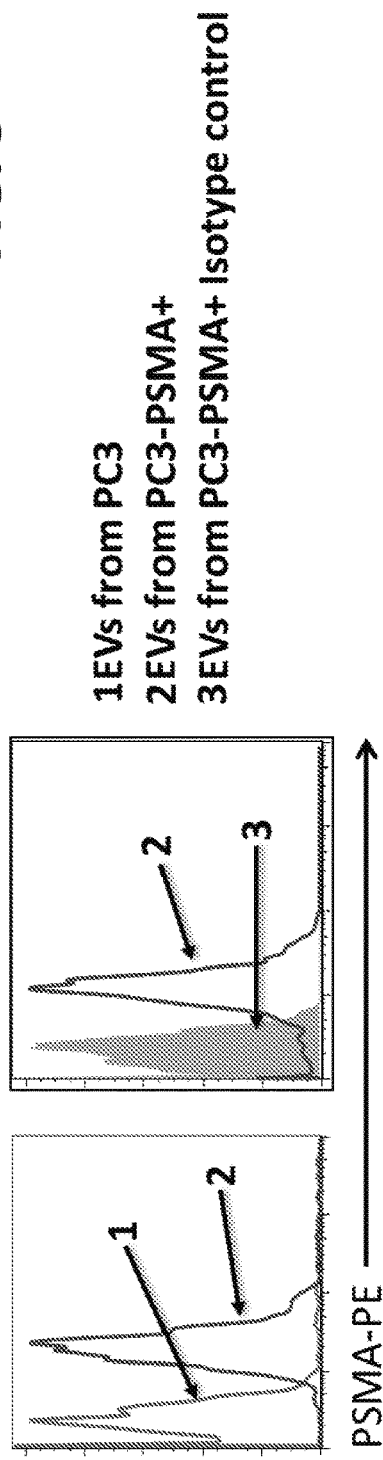
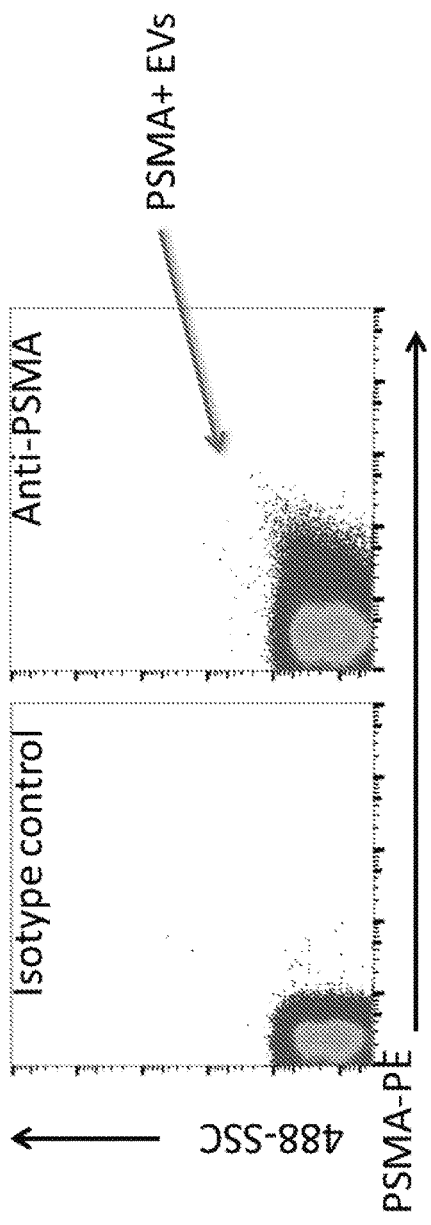

FIG. 7A
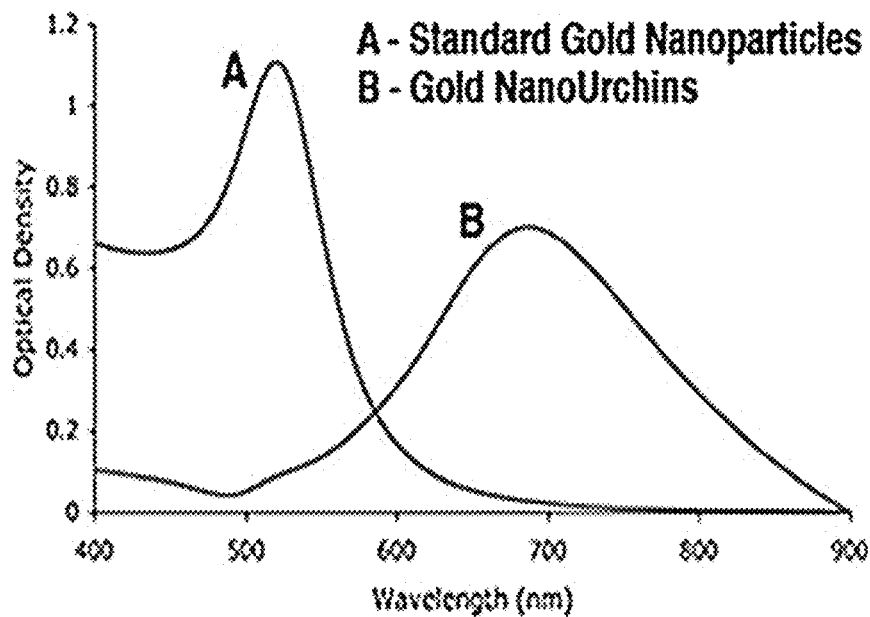
FIG. 7B  Gold Nanospheres
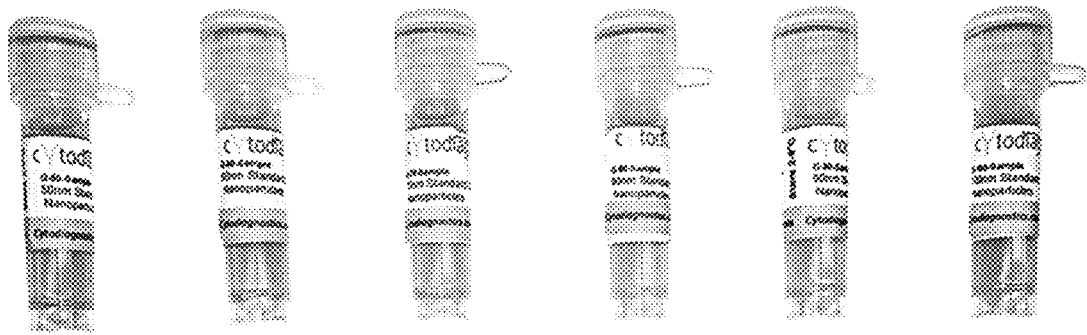
Gold Nanourchins
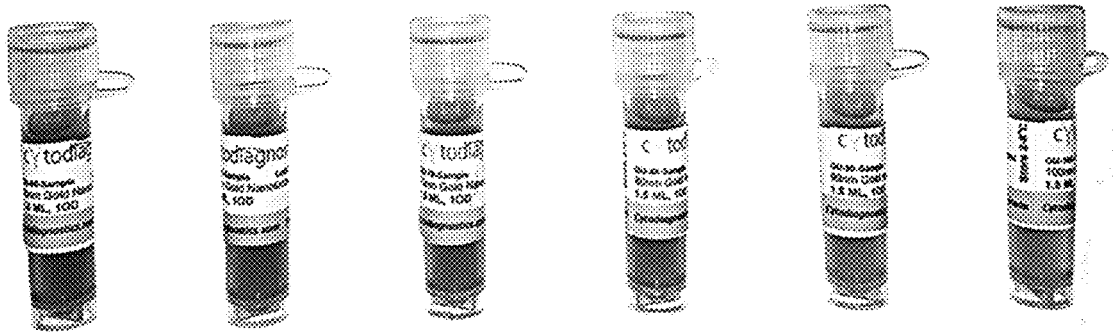

FIG. 8
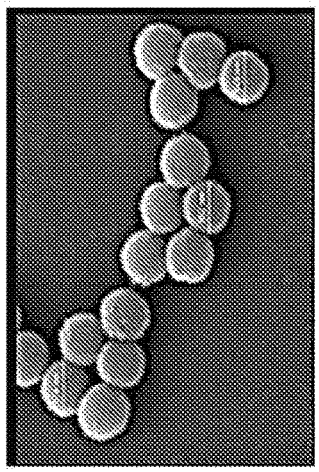 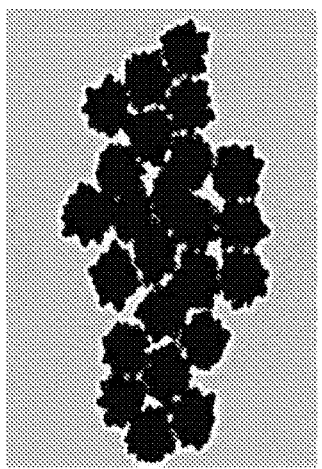 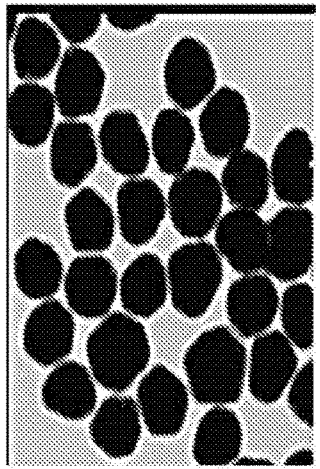
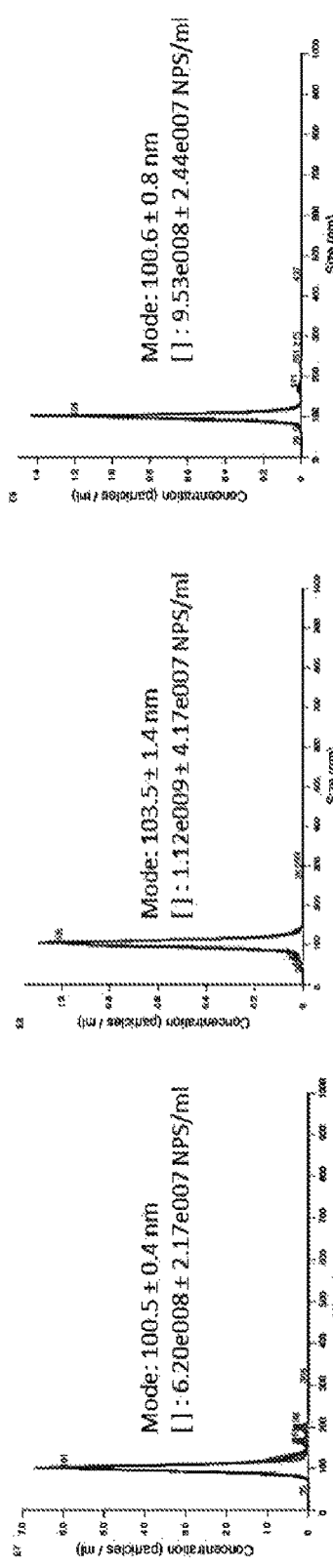
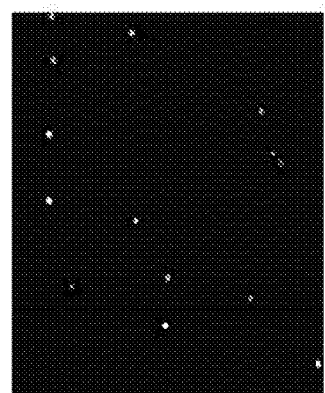 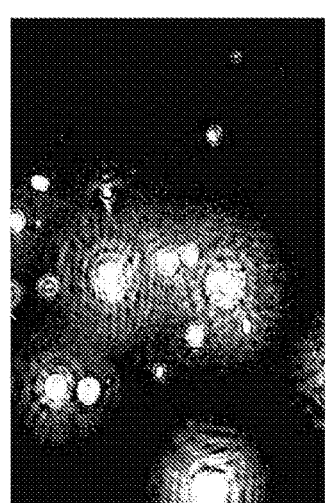

FIG. 9  Modular Components of Molecular NanoTag

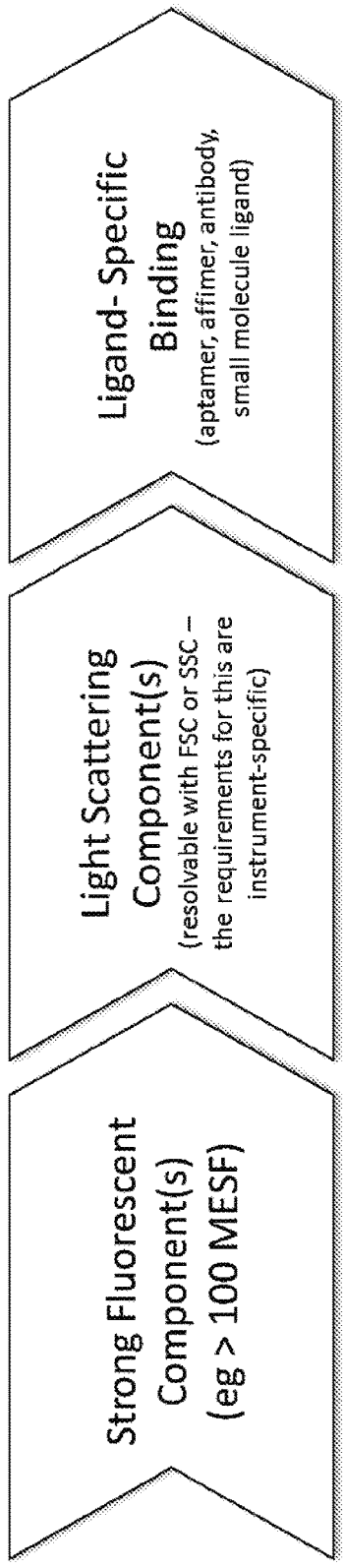

Strong Fluorescent Component(s) (eg > 100 MESF)

Light Scattering Component(s) (resolvable with FSC or SSC – the requirements for this are instrument-specific)

Ligand-Specific Binding (aptamer, affimer, antibody, small molecule ligand)

Synthetic Construction Considerations

➢ nanocrystal or metal core coatings: shell, passivation, additional coating(s), surface geometry (these can each impact fluorescence, scatter detection, solubility, and ligand-specificity)
➢ polyvalent: good for isolating ligand-associated EVs via pull-downs or nanoFACS sorting
➢ monovalent: enables single molecule counting, single EV labeling Molecular NanoTag – possible functional modifications (examples)

➢ FRET-enabled combinations of fluorophores and inorganic components
➢ Molecular Beacon-like quenchers that would silence fluorescence until ligand binding
➢ upconverting nanocrystal design to upconvert emission energy (reduce v)

Monovalent Qdot References WITHOUT scatter incorporation:

➢ Farlow et al (UCSF)
➢ Yan & Gao http://pubs.acs.org/doi/pdf/10.1021/bc200004z
➢ Uddayasakar et al http://pubs.acs.org/doi/pdf/10.1021/bc500203z

NCl IPDC Molecules
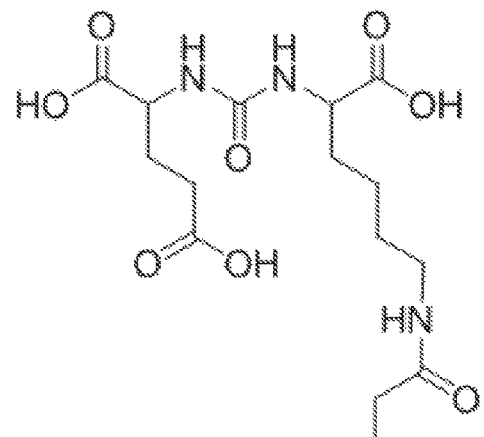
FIG. 10C
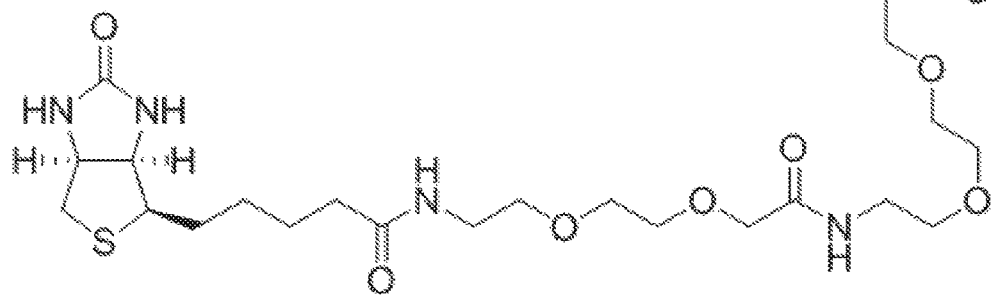
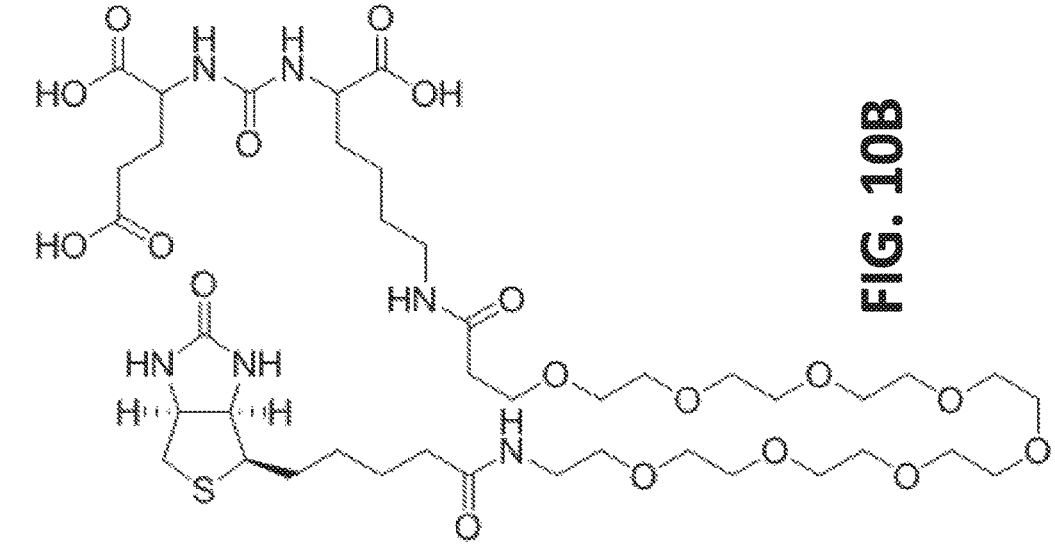
FIG. 10B

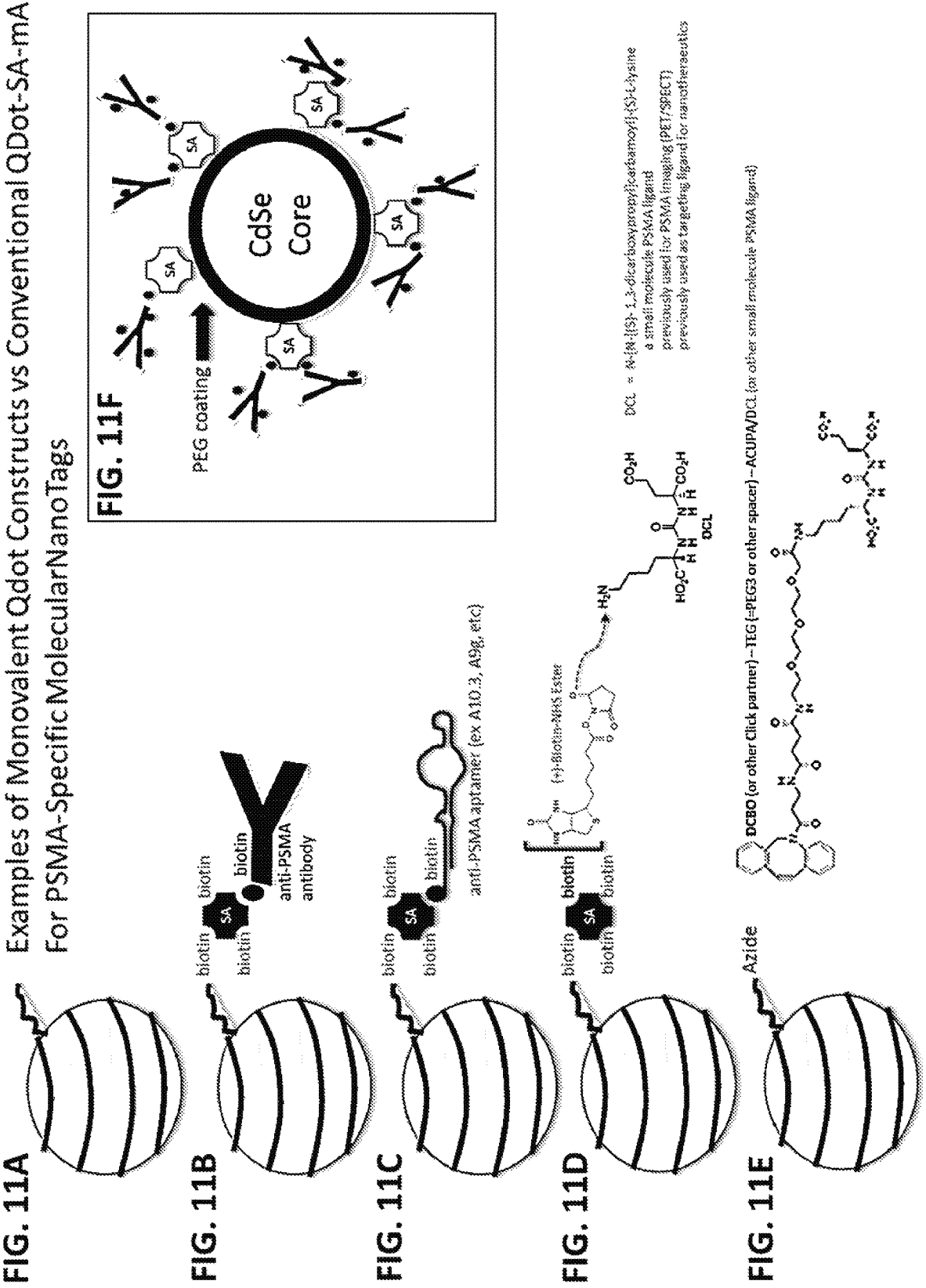

FIG. 12C 5' biotin-TEG spacer- (14) A9g

FIG. 12D Thiolated DNA Armor (12)  TEG spacer- (14) A9g

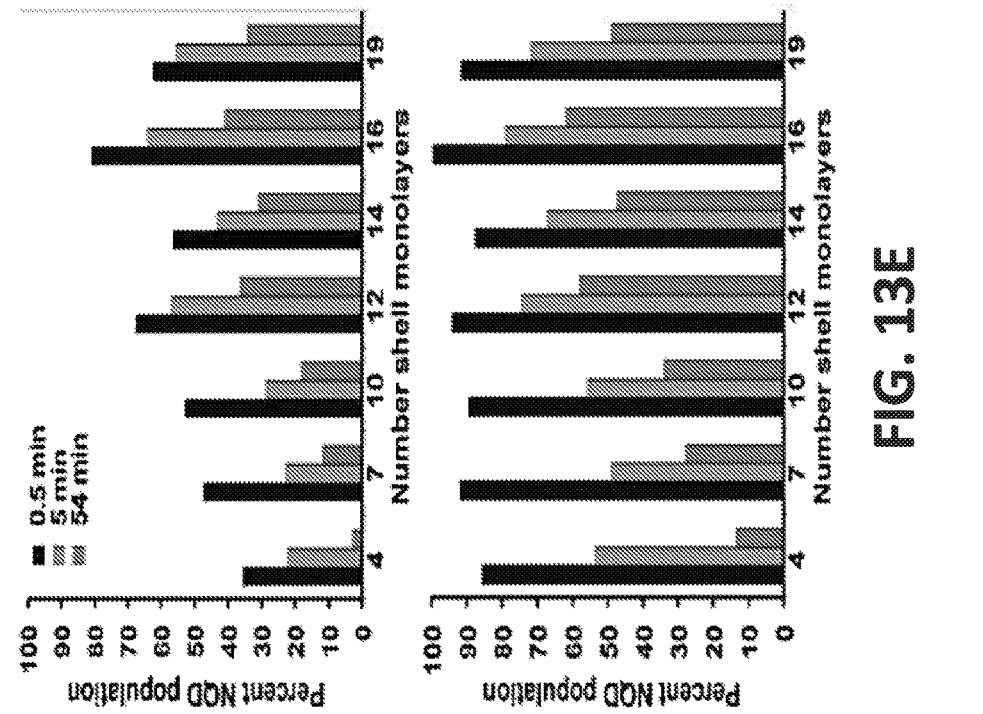
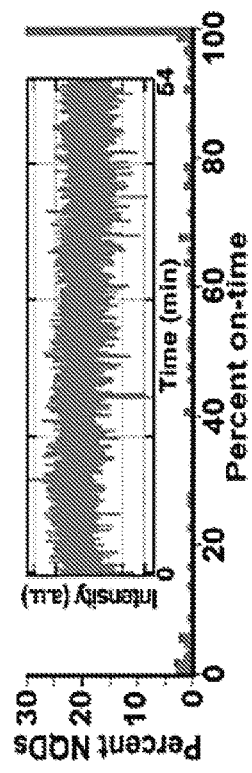
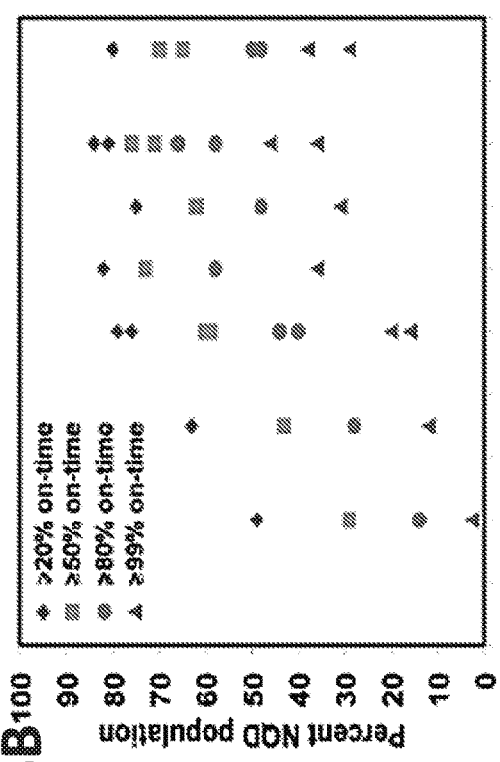
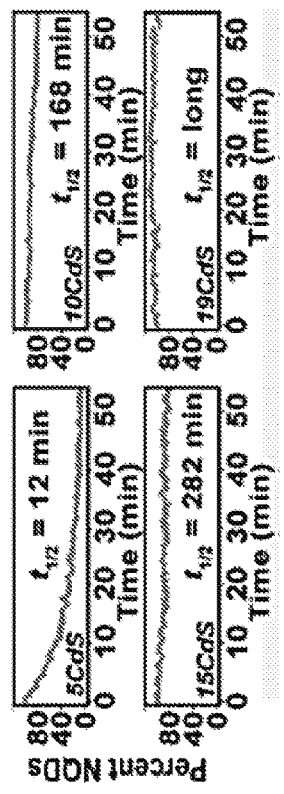
FIG. 13A  FIG. 13B  FIG. 13C  FIG. 13D  FIG. 13E

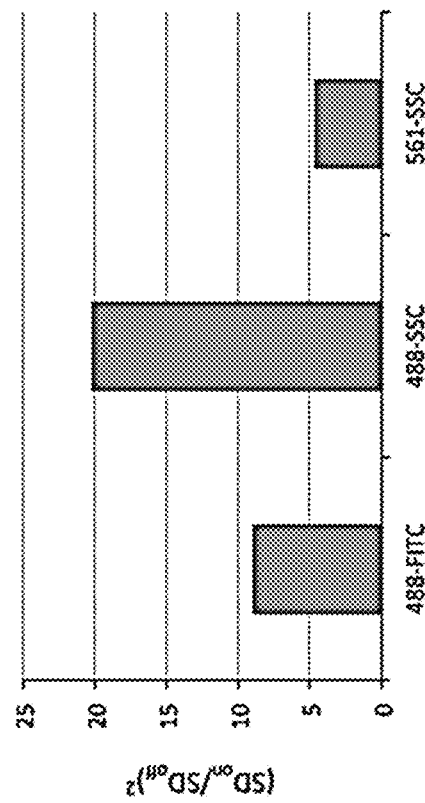
FIG. 14B
FIG. 14C
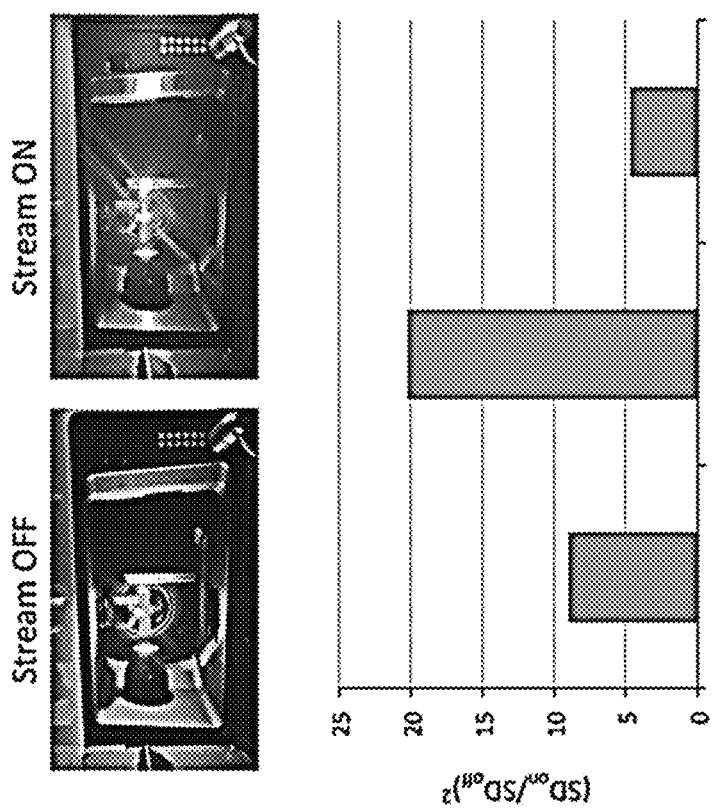
FIG. 14A

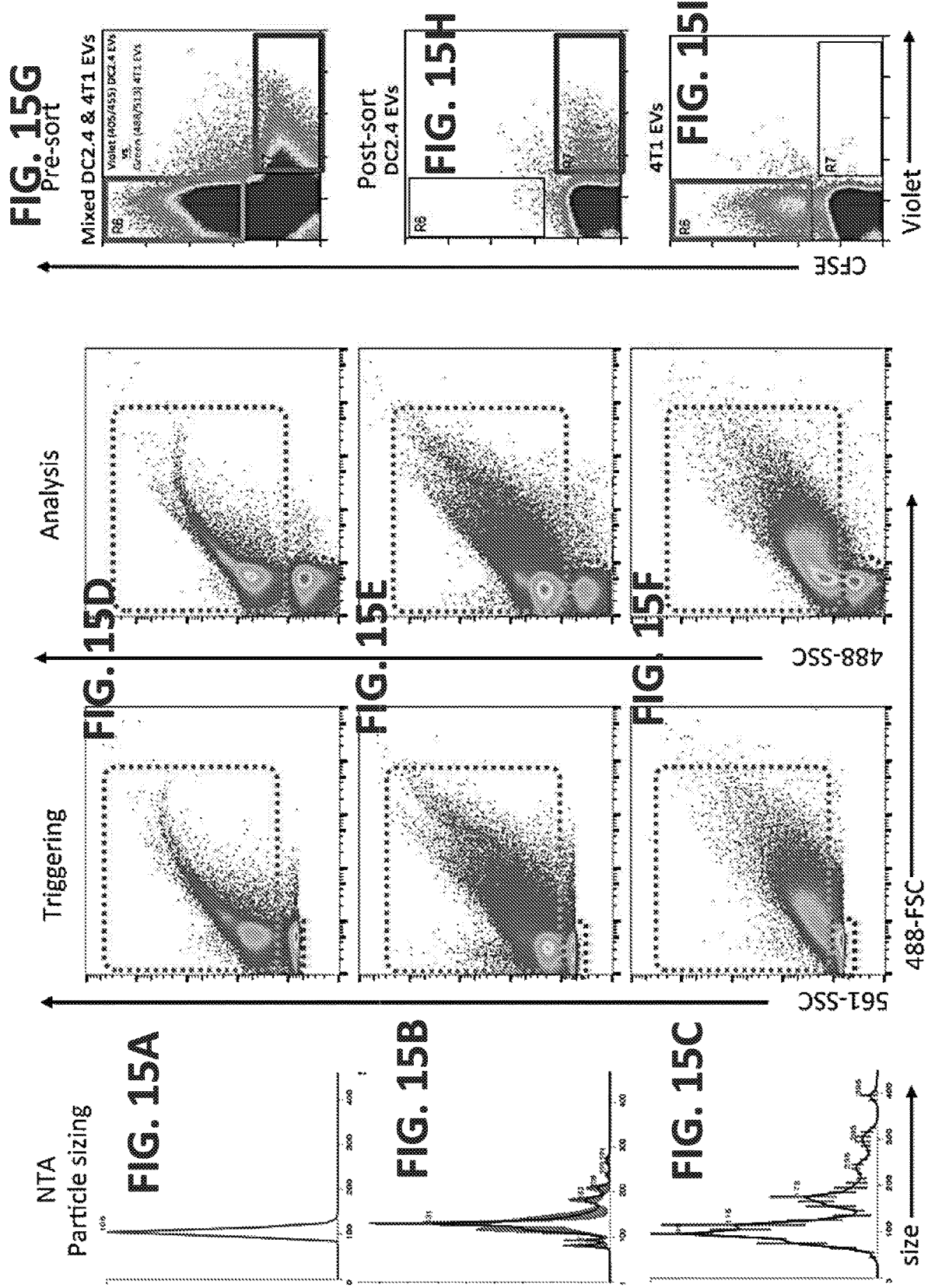

Spectral scattering characteristics of modelled and acquired gold and silver nanoparticles.

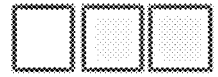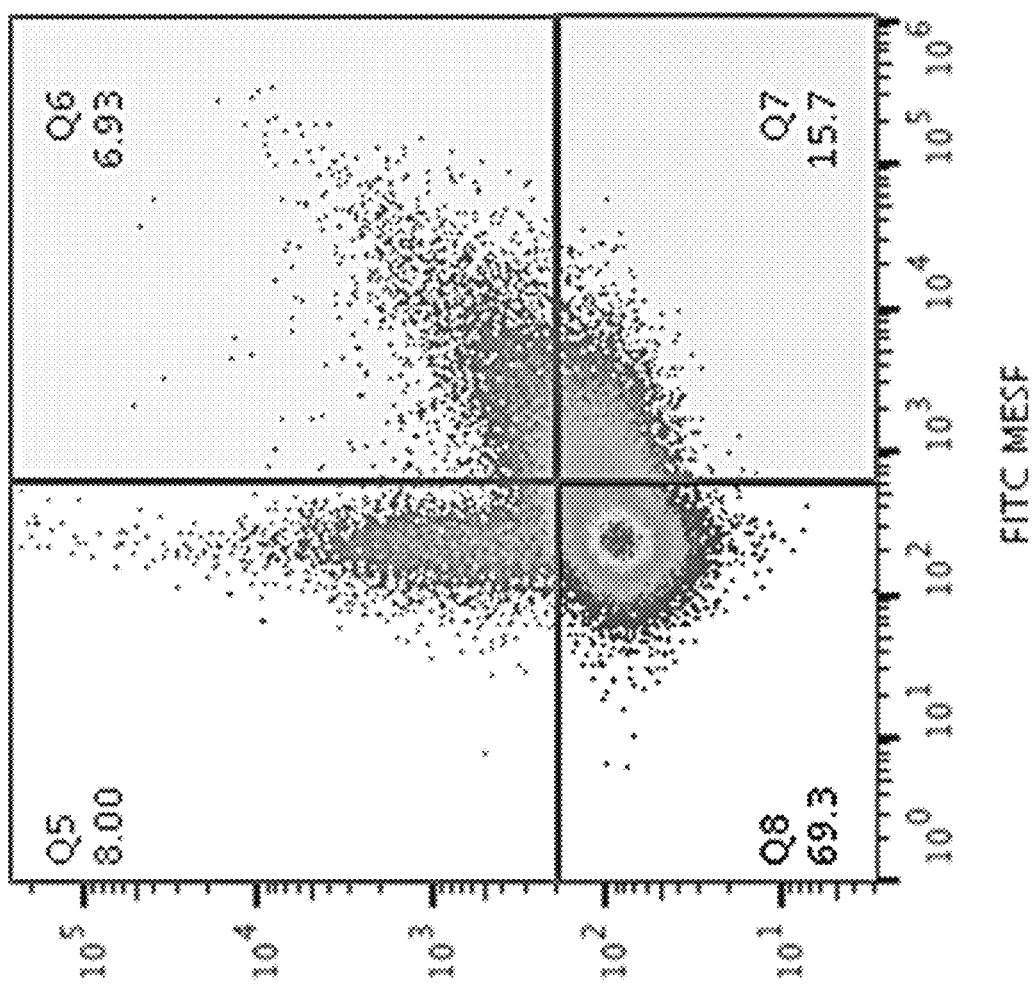
FIG. 18

FIG. 23A
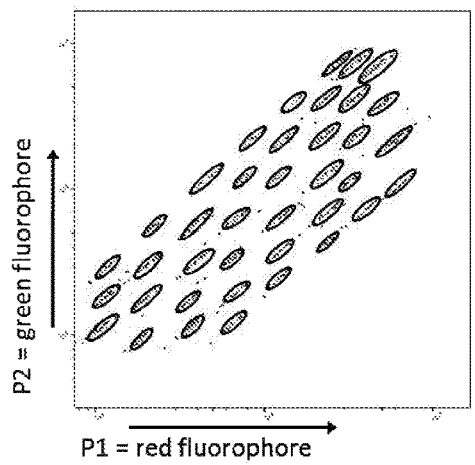
FIG. 23B
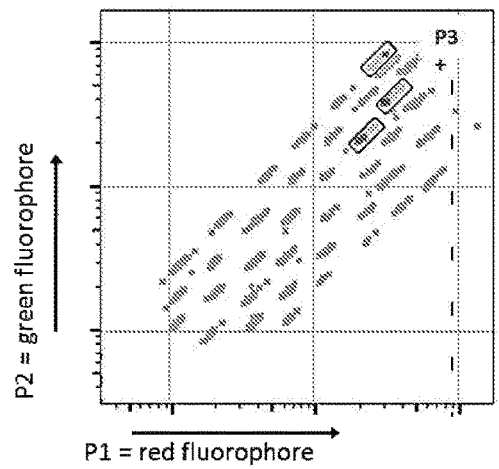
FIG. 23C
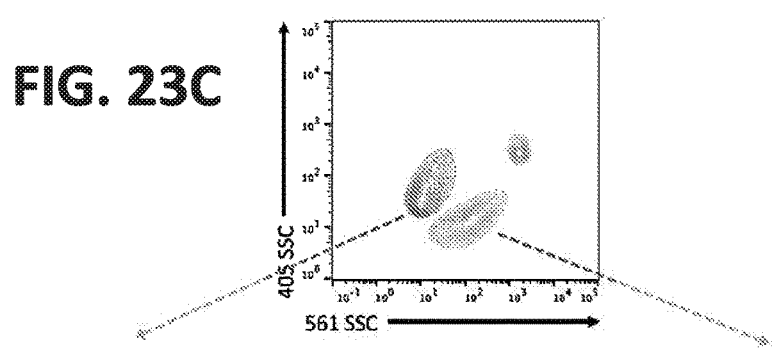
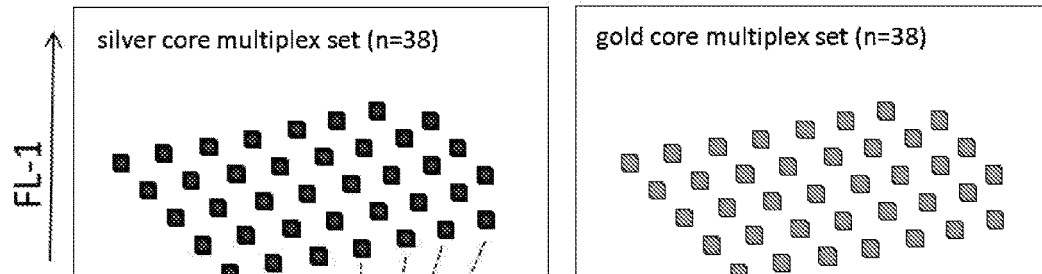
FIG. 23D
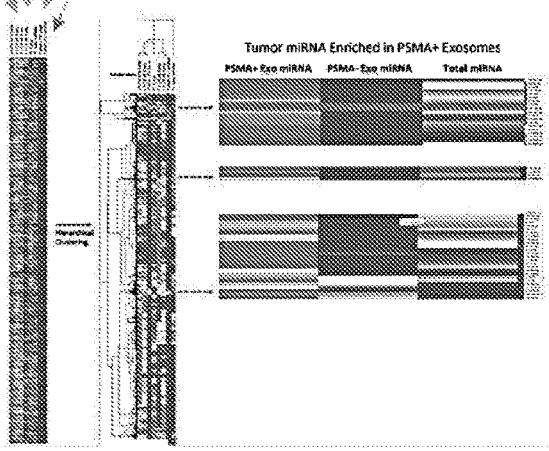

SEQUENCE LISTING

<160> NUMBER OF SEQ ID NOS: 13

<210> SEQ ID NO 1
<211> LENGTH: 39

```
<212> TYPE: RNA
<213> ORGANISM: Artificial Sequence
<220> FEATURE:
<223> OTHER INFORMATION: aptamer A10-3.2

<400> SEQUENCE: 1
gggaggacga ugcggaucag ccauguuuac gucacuccu                              39

<210> SEQ ID NO 2
<211> LENGTH: 43
<212> TYPE: RNA
<213> ORGANISM: Artificial Sequence
<220> FEATURE:
<223> OTHER INFORMATION: A9g aptamer

<400> SEQUENCE: 2
gggaccgaaa aagaccugac uucuauacua agucuacguu ccc                        43

<210> SEQ ID NO 3
<211> LENGTH: 43
<212> TYPE: RNA
<213> ORGANISM: Artificial Sequence
<220> FEATURE:
<223> OTHER INFORMATION: A9g.6 aptamer

<400> SEQUENCE: 3
gggaccgaaa aagaccuggc uucuauacua agucuacguu ccc                        43

<210> SEQ ID NO 4
<211> LENGTH: 113
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(50)
<223> OTHER INFORMATION: Phosphorothioated DNA
<220> FEATURE:
<221> NAME/KEY: misc_feature
<222> LOCATION: (71)..(113)
<223> OTHER INFORMATION: RNA
<220> FEATURE:
<221> NAME/KEY: modified_base
<222> LOCATION: (75)..(76)
<223> OTHER INFORMATION: 2'-Fluro
<220> FEATURE:
<221> NAME/KEY: modified_base
<222> LOCATION: (85)..(87)
<223> OTHER INFORMATION: 2'-Fluro
<220> FEATURE:
<221> NAME/KEY: modified_base
<222> LOCATION: (90)..(94)
<223> OTHER INFORMATION: 2'-Fluro
<220> FEATURE:
<221> NAME/KEY: modified_base
<222> LOCATION: (96)..(96)
<223> OTHER INFORMATION: 2'-Fluro
<220> FEATURE:
<221> NAME/KEY: modified_base
<222> LOCATION: (98)..(99)
<223> OTHER INFORMATION: 2'-Fluro
<220> FEATURE:
<221> NAME/KEY: modified_base
<222> LOCATION: (103)..(105)
<223> OTHER INFORMATION: 2'-Fluro
<220> FEATURE:
<221> NAME/KEY: modified_base
<222> LOCATION: (107)..(107)
<223> OTHER INFORMATION: 2'-Fluro
<220> FEATURE:
<221> NAME/KEY: modified_base
<222> LOCATION: (109)..(113)
```

<223> OTHER INFORMATION: 2'-Fluro

<400> SEQUENCE: 4
aaaaaaaaaa aaaaaaaaaa aaaaaaaaaa aaaaaaaaaa aaaaaaaaaa ctctctctct    60
ctctctctct gggaccgaaa aagaccugac uucuauacua agucuacguu ccc          113

<210> SEQ ID NO 5
<211> LENGTH: 109
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(50)
<223> OTHER INFORMATION: Phosphorothioated DNA
<220> FEATURE:
<221> NAME/KEY: misc_feature
<222> LOCATION: (71)..(77)
<223> OTHER INFORMATION: RNA
<220> FEATURE:
<221> NAME/KEY: modified_base
<222> LOCATION: (78)..(78)
<223> OTHER INFORMATION: 2'-Fluoro
<220> FEATURE:
<221> NAME/KEY: misc_feature
<222> LOCATION: (79)..(80)
<223> OTHER INFORMATION: RNA
<220> FEATURE:
<221> NAME/KEY: modified_base
<222> LOCATION: (81)..(81)
<223> OTHER INFORMATION: 2'-Fluoro
<220> FEATURE:
<221> NAME/KEY: misc_feature
<222> LOCATION: (82)..(82)
<223> OTHER INFORMATION: RNA
<220> FEATURE:
<221> NAME/KEY: modified_base
<222> LOCATION: (83)..(83)
<223> OTHER INFORMATION: 2'-Fluoro
<220> FEATURE:
<221> NAME/KEY: misc_feature
<222> LOCATION: (84)..(86)
<223> OTHER INFORMATION: RNA
<220> FEATURE:
<221> NAME/KEY: modified_base
<222> LOCATION: (87)..(88)
<223> OTHER INFORMATION: 2'-Fluoro
<220> FEATURE:
<221> NAME/KEY: misc_feature
<222> LOCATION: (89)..(90)
<223> OTHER INFORMATION: RNA
<220> FEATURE:
<221> NAME/KEY: modified_base
<222> LOCATION: (91)..(92)
<223> OTHER INFORMATION: 2'-Fluoro
<220> FEATURE:
<221> NAME/KEY: misc_feature
<222> LOCATION: (93)..(93)
<223> OTHER INFORMATION: RNA
<220> FEATURE:
<221> NAME/KEY: modified_base
<222> LOCATION: (94)..(94)
<223> OTHER INFORMATION: 2'-Fluoro
<220> FEATURE:
<221> NAME/KEY: misc_feature
<222> LOCATION: (95)..(95)
<223> OTHER INFORMATION: RNA
<220> FEATURE:
<221> NAME/KEY: modified_base
<222> LOCATION: (96)..(98)
<223> OTHER INFORMATION: 2'-Fluoro
<220> FEATURE:
<221> NAME/KEY: misc_feature
<222> LOCATION: (99)..(99)
<223> OTHER INFORMATION: RNA

```
<220> FEATURE:
<221> NAME/KEY: modified_base
<222> LOCATION: (100)..(100)
<223> OTHER INFORMATION: 2'-Fluoro
<220> FEATURE:
<221> NAME/KEY: misc_feature
<222> LOCATION: (101)..(101)
<223> OTHER INFORMATION: RNA
<220> FEATURE:
<221> NAME/KEY: modified_base
<222> LOCATION: (102)..(103)
<223> OTHER INFORMATION: 2'-Fluoro
<220> FEATURE:
<221> NAME/KEY: misc_feature
<222> LOCATION: (104)..(104)
<223> OTHER INFORMATION: RNA
<220> FEATURE:
<221> NAME/KEY: modified_base
<222> LOCATION: (105)..(108)
<223> OTHER INFORMATION: 2'-Fluoro
<220> FEATURE:
<221> NAME/KEY: modified_base
<222> LOCATION: (109)..(109)
<223> OTHER INFORMATION: 2-fluorouridine

<400> SEQUENCE: 5
aaaaaaaaaa aaaaaaaaaa aaaaaaaaaa aaaaaaaaaa aaaaaaaaaa ctctctctct      60
ctctctctct gggaggacga ugcggaucag ccauguuuac gucacuccu                  109

<210> SEQ ID NO 6
<211> LENGTH: 70
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(50)
<223> OTHER INFORMATION: Phosphorothioated DNA
<220> FEATURE:
<221> NAME/KEY: modified_base
<222> LOCATION: (70)..(70)
<223> OTHER INFORMATION: C6 dT, 3'-Biotin-tetraethylene glycol

<400> SEQUENCE: 6
aaaaaaaaaa aaaaaaaaaa aaaaaaaaaa aaaaaaaaaa aaaaaaaaaa ctctctctct      60
ctctctctct                                                             70

<210> SEQ ID NO 7
<211> LENGTH: 70
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(50)
<223> OTHER INFORMATION: Phosphorothioated DNA
<220> FEATURE:
<221> NAME/KEY: modified_base
<222> LOCATION: (70)..(70)
<223> OTHER INFORMATION: 3'-Azide

<400> SEQUENCE: 7
aaaaaaaaaa aaaaaaaaaa aaaaaaaaaa aaaaaaaaaa aaaaaaaaaa ctctctctct      60
ctctctctct                                                             70

<210> SEQ ID NO 8
<211> LENGTH: 44
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5' biotin with a single glycol linker
<220> FEATURE:
<221> NAME/KEY: modified_base
<222> LOCATION: (1)..(1)
<223> OTHER INFORMATION: 2'-Fluoro
<220> FEATURE:
<221> NAME/KEY: misc_feature
<222> LOCATION: (2)..(5)
<223> OTHER INFORMATION: RNA
<220> FEATURE:
<221> NAME/KEY: modified_base
<222> LOCATION: (6)..(7)
<223> OTHER INFORMATION: 2'-Fluoro
<220> FEATURE:
<221> NAME/KEY: misc_feature
<222> LOCATION: (8)..(15)
<223> OTHER INFORMATION: RNA
<220> FEATURE:
<221> NAME/KEY: modified_base
<222> LOCATION: (16)..(18)
<223> OTHER INFORMATION: 2'-Fluoro
<220> FEATURE:
<221> NAME/KEY: misc_feature
<222> LOCATION: (19)..(20)
<223> OTHER INFORMATION: RNA
<220> FEATURE:
<221> NAME/KEY: modified_base
<222> LOCATION: (21)..(25)
<223> OTHER INFORMATION: 2'-Fluoro
<220> FEATURE:
<221> NAME/KEY: misc_feature
<222> LOCATION: (26)..(26)
<223> OTHER INFORMATION: RNA
<220> FEATURE:
<221> NAME/KEY: modified_base
<222> LOCATION: (27)..(27)
<223> OTHER INFORMATION: 2'-Fluoro
<220> FEATURE:
<221> NAME/KEY: misc_feature
<222> LOCATION: (28)..(28)
<223> OTHER INFORMATION: RNA
<220> FEATURE:
<221> NAME/KEY: modified_base
<222> LOCATION: (29)..(30)
<223> OTHER INFORMATION: 2'-Fluoro
<220> FEATURE:
<221> NAME/KEY: misc_feature
<222> LOCATION: (31)..(33)
<223> OTHER INFORMATION: RNA
<220> FEATURE:
<221> NAME/KEY: modified_base
<222> LOCATION: (34)..(36)
<223> OTHER INFORMATION: 2'-Fluoro
<220> FEATURE:
<221> NAME/KEY: misc_feature
<222> LOCATION: (37)..(37)
<223> OTHER INFORMATION: RNA
<220> FEATURE:
<221> NAME/KEY: modified_base
<222> LOCATION: (38)..(38)
<223> OTHER INFORMATION: 2'-Fluoro
<220> FEATURE:
<221> NAME/KEY: misc_feature
<222> LOCATION: (39)..(39)
<223> OTHER INFORMATION: RNA
<220> FEATURE:
<221> NAME/KEY: modified_base
<222> LOCATION: (40)..(43)
<223> OTHER INFORMATION: 2'-Fluoro
<220> FEATURE:
<221> NAME/KEY: modified_base
<222> LOCATION: (44)..(44)
<223> OTHER INFORMATION: 3'-Fluoro C
```

-continued

<400> SEQUENCE: 8
ugggaccgaa aaagaccuga cuucuauacu aagucuacgu uccc     44

<210> SEQ ID NO 9
<211> LENGTH: 39
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5'-Biotin tetraethylene glycol
<220> FEATURE:
<221> NAME/KEY: misc_feature
<222> LOCATION: (1)..(7)
<223> OTHER INFORMATION: RNA
<220> FEATURE:
<221> NAME/KEY: modified_base
<222> LOCATION: (8)..(8)
<223> OTHER INFORMATION: 2'-Fluoro
<220> FEATURE:
<221> NAME/KEY: misc_feature
<222> LOCATION: (9)..(10)
<223> OTHER INFORMATION: RNA
<220> FEATURE:
<221> NAME/KEY: modified_base
<222> LOCATION: (11)..(11)
<223> OTHER INFORMATION: 2'-Fluoro
<220> FEATURE:
<221> NAME/KEY: misc_feature
<222> LOCATION: (12)..(16)
<223> OTHER INFORMATION: RNA
<220> FEATURE:
<221> NAME/KEY: modified_base
<222> LOCATION: (13)..(13)
<223> OTHER INFORMATION: 2'-Fluoro
<220> FEATURE:
<221> NAME/KEY: modified_base
<222> LOCATION: (17)..(18)
<223> OTHER INFORMATION: 2'-Fluoro
<220> FEATURE:
<221> NAME/KEY: misc_feature
<222> LOCATION: (19)..(20)
<223> OTHER INFORMATION: RNA
<220> FEATURE:
<221> NAME/KEY: modified_base
<222> LOCATION: (21)..(22)
<223> OTHER INFORMATION: 2'-Fluoro
<220> FEATURE:
<221> NAME/KEY: misc_feature
<222> LOCATION: (23)..(23)
<223> OTHER INFORMATION: RNA
<220> FEATURE:
<221> NAME/KEY: modified_base
<222> LOCATION: (24)..(24)
<223> OTHER INFORMATION: 2'-Fluoro
<220> FEATURE:
<221> NAME/KEY: misc_feature
<222> LOCATION: (25)..(25)
<223> OTHER INFORMATION: RNA
<220> FEATURE:
<221> NAME/KEY: modified_base
<222> LOCATION: (26)..(28)
<223> OTHER INFORMATION: 2'-Fluoro
<220> FEATURE:
<221> NAME/KEY: misc_feature
<222> LOCATION: (29)..(29)
<223> OTHER INFORMATION: RNA
<220> FEATURE:
<221> NAME/KEY: modified_base
<222> LOCATION: (30)..(30)
<223> OTHER INFORMATION: 2'-Fluoro
<220> FEATURE:
<221> NAME/KEY: misc_feature
<222> LOCATION: (31)..(31)

-continued

```
<223> OTHER INFORMATION: RNA
<220> FEATURE:
<221> NAME/KEY: modified_base
<222> LOCATION: (32)..(33)
<223> OTHER INFORMATION: 2'-Fluoro
<220> FEATURE:
<221> NAME/KEY: modified_base
<222> LOCATION: (35)..(38)
<223> OTHER INFORMATION: 2'-Fluoro
<220> FEATURE:
<221> NAME/KEY: modified_base
<222> LOCATION: (39)..(39)
<223> OTHER INFORMATION: 2-Fluorouridine

<400> SEQUENCE: 9
gggaggacga ugcggaucag ccauguuuac gucacuccu                        39

<210> SEQ ID NO 10
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5'-biotin with single glycol linker
<220> FEATURE:
<221> NAME/KEY: modified_base
<222> LOCATION: (1)..(1)
<223> OTHER INFORMATION: 2'-Fluoro
<220> FEATURE:
<221> NAME/KEY: misc_feature
<222> LOCATION: (1)..(5)
<223> OTHER INFORMATION: RNA
<220> FEATURE:
<221> NAME/KEY: modified_base
<222> LOCATION: (6)..(7)
<223> OTHER INFORMATION: 2'-Fluoro
<220> FEATURE:
<221> NAME/KEY: misc_feature
<222> LOCATION: (8)..(15)
<223> OTHER INFORMATION: RNA
<220> FEATURE:
<221> NAME/KEY: modified_base
<222> LOCATION: (16)..(18)
<223> OTHER INFORMATION: 2'-Fluoro
<220> FEATURE:
<221> NAME/KEY: misc_feature
<222> LOCATION: (19)..(20)
<223> OTHER INFORMATION: RNA
<220> FEATURE:
<221> NAME/KEY: modified_base
<222> LOCATION: (21)..(25)
<223> OTHER INFORMATION: 2'-Fluoro
<220> FEATURE:
<221> NAME/KEY: misc_feature
<222> LOCATION: (26)..(26)
<223> OTHER INFORMATION: RNA
<220> FEATURE:
<221> NAME/KEY: modified_base
<222> LOCATION: (27)..(27)
<223> OTHER INFORMATION: 2'-Fluoro
<220> FEATURE:
<221> NAME/KEY: misc_feature
<222> LOCATION: (28)..(28)
<223> OTHER INFORMATION: RNA
<220> FEATURE:
<221> NAME/KEY: modified_base
<222> LOCATION: (29)..(30)
<223> OTHER INFORMATION: 2'-Fluoro
<220> FEATURE:
<221> NAME/KEY: misc_feature
<222> LOCATION: (31)..(33)
<223> OTHER INFORMATION: RNA
<220> FEATURE:
<221> NAME/KEY: modified_base
```

```
<222> LOCATION: (34)..(36)
<223> OTHER INFORMATION: 2'-Fluoro
<220> FEATURE:
<221> NAME/KEY: misc_feature
<222> LOCATION: (37)..(37)
<223> OTHER INFORMATION: RNA
<220> FEATURE:
<221> NAME/KEY: modified_base
<222> LOCATION: (38)..(38)
<223> OTHER INFORMATION: 2'-Fluoro
<220> FEATURE:
<221> NAME/KEY: misc_feature
<222> LOCATION: (39)..(39)
<223> OTHER INFORMATION: RNA
<220> FEATURE:
<221> NAME/KEY: modified_base
<222> LOCATION: (40)..(43)
<223> OTHER INFORMATION: 2'-Fluoro
<220> FEATURE:
<221> NAME/KEY: modified_base
<222> LOCATION: (44)..(44)
<223> OTHER INFORMATION: 2-fluorouridine

<400> SEQUENCE: 10
ugggaccgaa aaagaccuga cuucuauacu aagucuacgu uccc                         44

<210> SEQ ID NO 11
<211> LENGTH: 39
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5'-biotin with single glycol linker
<220> FEATURE:
<221> NAME/KEY: misc_feature
<222> LOCATION: (1)..(7)
<223> OTHER INFORMATION: RNA
<220> FEATURE:
<221> NAME/KEY: modified_base
<222> LOCATION: (8)..(8)
<223> OTHER INFORMATION: 2'-Fluoro
<220> FEATURE:
<221> NAME/KEY: misc_feature
<222> LOCATION: (9)..(10)
<223> OTHER INFORMATION: RNA
<220> FEATURE:
<221> NAME/KEY: modified_base
<222> LOCATION: (11)..(11)
<223> OTHER INFORMATION: 2'-Fluoro
<220> FEATURE:
<221> NAME/KEY: misc_feature
<222> LOCATION: (12)..(12)
<223> OTHER INFORMATION: RNA
<220> FEATURE:
<221> NAME/KEY: modified_base
<222> LOCATION: (13)..(13)
<223> OTHER INFORMATION: 2'-Fluoro
<220> FEATURE:
<221> NAME/KEY: misc_feature
<222> LOCATION: (14)..(16)
<223> OTHER INFORMATION: RNA
<220> FEATURE:
<221> NAME/KEY: modified_base
<222> LOCATION: (17)..(18)
<223> OTHER INFORMATION: 2'-Fluoro
<220> FEATURE:
<221> NAME/KEY: misc_feature
<222> LOCATION: (19)..(20)
<223> OTHER INFORMATION: RNA
<220> FEATURE:
<221> NAME/KEY: modified_base
<222> LOCATION: (21)..(22)
<223> OTHER INFORMATION: 2'-Fluoro
<220> FEATURE:
```

```
<221> NAME/KEY: misc_feature
<222> LOCATION: (23)..(23)
<223> OTHER INFORMATION: RNA
<220> FEATURE:
<221> NAME/KEY: modified_base
<222> LOCATION: (24)..(24)
<223> OTHER INFORMATION: 2'-Fluoro
<220> FEATURE:
<221> NAME/KEY: misc_feature
<222> LOCATION: (25)..(25)
<223> OTHER INFORMATION: RNA
<220> FEATURE:
<221> NAME/KEY: modified_base
<222> LOCATION: (26)..(28)
<223> OTHER INFORMATION: 2'-Fluoro
<220> FEATURE:
<221> NAME/KEY: misc_feature
<222> LOCATION: (29)..(29)
<223> OTHER INFORMATION: RNA
<220> FEATURE:
<221> NAME/KEY: modified_base
<222> LOCATION: (30)..(30)
<223> OTHER INFORMATION: 2'-Fluoro
<220> FEATURE:
<221> NAME/KEY: misc_feature
<222> LOCATION: (31)..(31)
<223> OTHER INFORMATION: RNA
<220> FEATURE:
<221> NAME/KEY: modified_base
<222> LOCATION: (32)..(33)
<223> OTHER INFORMATION: 2'-Fluoro
<220> FEATURE:
<221> NAME/KEY: misc_feature
<222> LOCATION: (34)..(34)
<223> OTHER INFORMATION: RNA
<220> FEATURE:
<221> NAME/KEY: modified_base
<222> LOCATION: (35)..(38)
<223> OTHER INFORMATION: 2'-Fluoro
<220> FEATURE:
<221> NAME/KEY: modified_base
<222> LOCATION: (39)..(39)
<223> OTHER INFORMATION: 2-fluorouridine

<400> SEQUENCE: 11
gggaggacga ugcggaucag ccauguuuac gucacuccu                    39

<210> SEQ ID NO 12
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5'dibenzocylcloctyl, tetraethylene glycol
<220> FEATURE:
<221> NAME/KEY: modified_base
<222> LOCATION: (1)..(1)
<223> OTHER INFORMATION: 2'-Fluoro
<220> FEATURE:
<221> NAME/KEY: misc_feature
<222> LOCATION: (1)..(5)
<223> OTHER INFORMATION: RNA
<220> FEATURE:
<221> NAME/KEY: modified_base
<222> LOCATION: (6)..(7)
<223> OTHER INFORMATION: 2'-Fluoro
<220> FEATURE:
<221> NAME/KEY: misc_feature
<222> LOCATION: (8)..(15)
<223> OTHER INFORMATION: RNA
<220> FEATURE:
<221> NAME/KEY: modified_base
<222> LOCATION: (16)..(18)
<223> OTHER INFORMATION: 2'-Fluoro
```

```
<220> FEATURE:
<221> NAME/KEY: misc_feature
<222> LOCATION: (19)..(20)
<223> OTHER INFORMATION: RNA
<220> FEATURE:
<221> NAME/KEY: modified_base
<222> LOCATION: (21)..(25)
<223> OTHER INFORMATION: 2'-Fluoro
<220> FEATURE:
<221> NAME/KEY: misc_feature
<222> LOCATION: (26)..(28)
<223> OTHER INFORMATION: RNA
<220> FEATURE:
<221> NAME/KEY: modified_base
<222> LOCATION: (29)..(30)
<223> OTHER INFORMATION: 2'-Fluoro
<220> FEATURE:
<221> NAME/KEY: misc_feature
<222> LOCATION: (31)..(33)
<223> OTHER INFORMATION: RNA
<220> FEATURE:
<221> NAME/KEY: modified_base
<222> LOCATION: (34)..(36)
<223> OTHER INFORMATION: 2'-Fluoro
<220> FEATURE:
<221> NAME/KEY: misc_feature
<222> LOCATION: (37)..(37)
<223> OTHER INFORMATION: RNA
<220> FEATURE:
<221> NAME/KEY: modified_base
<222> LOCATION: (38)..(38)
<223> OTHER INFORMATION: 2'-Fluoro
<220> FEATURE:
<221> NAME/KEY: misc_feature
<222> LOCATION: (39)..(39)
<223> OTHER INFORMATION: RNA
<220> FEATURE:
<221> NAME/KEY: modified_base
<222> LOCATION: (40)..(43)
<223> OTHER INFORMATION: 2'-Fluoro
<220> FEATURE:
<221> NAME/KEY: modified_base
<222> LOCATION: (44)..(44)
<223> OTHER INFORMATION: 2-fluorouridine

<400> SEQUENCE: 12
ugggaccgaa aaagaccuga cuucuauacu aagucuacgu uccc                         44

<210> SEQ ID NO 13
<211> LENGTH: 39
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 5'dibenzocylcloctyl, tetraethylene glycol
<220> FEATURE:
<221> NAME/KEY: misc_feature
<222> LOCATION: (1)..(7)
<223> OTHER INFORMATION: RNA
<220> FEATURE:
<221> NAME/KEY: modified_base
<222> LOCATION: (8)..(8)
<223> OTHER INFORMATION: 2'-Fluoro
<220> FEATURE:
<221> NAME/KEY: misc_feature
<222> LOCATION: (9)..(10)
<223> OTHER INFORMATION: RNA
<220> FEATURE:
<221> NAME/KEY: modified_base
<222> LOCATION: (11)..(11)
<223> OTHER INFORMATION: 2'-Fluoro
<220> FEATURE:
<221> NAME/KEY: misc_feature
<222> LOCATION: (12)..(12)
```

```
<223> OTHER INFORMATION: RNA
<220> FEATURE:
<221> NAME/KEY: modified_base
<222> LOCATION: (13)..(13)
<223> OTHER INFORMATION: 2'-Fluoro
<220> FEATURE:
<221> NAME/KEY: misc_feature
<222> LOCATION: (14)..(16)
<223> OTHER INFORMATION: RNA
<220> FEATURE:
<221> NAME/KEY: modified_base
<222> LOCATION: (17)..(18)
<223> OTHER INFORMATION: 2'-Fluoro
<220> FEATURE:
<221> NAME/KEY: misc_feature
<222> LOCATION: (19)..(20)
<223> OTHER INFORMATION: RNA
<220> FEATURE:
<221> NAME/KEY: modified_base
<222> LOCATION: (21)..(22)
<223> OTHER INFORMATION: 2'-Fluoro
<220> FEATURE:
<221> NAME/KEY: misc_feature
<222> LOCATION: (23)..(23)
<223> OTHER INFORMATION: RNA
<220> FEATURE:
<221> NAME/KEY: modified_base
<222> LOCATION: (24)..(24)
<223> OTHER INFORMATION: 2'-Fluoro
<220> FEATURE:
<221> NAME/KEY: misc_feature
<222> LOCATION: (25)..(25)
<223> OTHER INFORMATION: RNA
<220> FEATURE:
<221> NAME/KEY: modified_base
<222> LOCATION: (26)..(28)
<223> OTHER INFORMATION: 2'-Fluoro
<220> FEATURE:
<221> NAME/KEY: misc_feature
<222> LOCATION: (29)..(29)
<223> OTHER INFORMATION: RNA
<220> FEATURE:
<221> NAME/KEY: modified_base
<222> LOCATION: (30)..(30)
<223> OTHER INFORMATION: 2'-Fluoro
<220> FEATURE:
<221> NAME/KEY: misc_feature
<222> LOCATION: (31)..(31)
<223> OTHER INFORMATION: RNA
<220> FEATURE:
<221> NAME/KEY: modified_base
<222> LOCATION: (32)..(33)
<223> OTHER INFORMATION: 2'-Fluoro
<220> FEATURE:
<221> NAME/KEY: misc_feature
<222> LOCATION: (34)..(34)
<223> OTHER INFORMATION: RNA
<220> FEATURE:
<221> NAME/KEY: modified_base
<222> LOCATION: (35)..(38)
<223> OTHER INFORMATION: 2'-Fluoro
<220> FEATURE:
<221> NAME/KEY: modified_base
<222> LOCATION: (39)..(39)
<223> OTHER INFORMATION: 2-fluorouridine

<400> SEQUENCE: 13
gggaggacga ugcggaucag ccauguuuac gucacuccu                    39
```

MOLECULAR NANOTAGS

CROSS REFERENCE TO RELATED APPLICATIONS

This application is the U.S. National Stage of International Application No. PCT/US2017/057928, filed Oct. 23, 2017, which claims the benefit of the earlier filing date of U.S. Provisional Application No. 62/411,324, filed Oct. 21, 2016, which are herein incorporated by reference in their entireties.

ACKNOWLEDGEMENT OF GOVERNMENT SUPPORT

This invention was made with Government support under project number Z01BC011502 by the National Institutes of Health, National Cancer Institute. The Government has certain rights in the invention."

FIELD

This disclosure concerns nanoscale molecular tags and their use for the detection of targets, for example in a flow cytometer.

BACKGROUND

Improved methods and devices for single nanoparticle detection, resolution and/or sorting would be advantageous for both clinical and research purposes. For example, they would be useful to identify and analyze extracellular vesicles (EVs) and other nanoscale particles released by cells that have important biological functions and significant biomedical potential for use as therapeutic agents, targets or biomarkers. It is generally accepted that the constituent components and biological function of EVs vary, based on the type of cell that produces them and the conditions under which they are produced (Raposo and Stoorvogel, *J Cell Biol* 200(4):373-383, 2013). However, it has not previously been possible to characterize subsets of these particles in the way that cellular lineages and subsets have been defined. Similarly, it has previously been difficult to detect, sort and count other nanoscale particles as well as individual molecular components of these nanoscale particles. An obstacle to this technology has been the lack of available tools and reagents to analyze, sort, and functionally study individual nanoscale particles, based on specific attributes.

Fluorescent activated cell sorting (FACS) has been used since its introduction by Herzenberg and colleagues in 1972 to identify and sort labeled subsets of cells (Julius et al., *Proc Natl Acacl Sci USA* 69(7):1934-1938, 1972; Bonner et al, *Rev Sci Instrum* 43:404-409, 1972), but sorting submicron subpopulations has not been considered feasible for particles smaller than approximately 500 nm. Conventional wisdom in flow cytometry holds that the signal from particles smaller than one micrometer would be lost in the signal from sample debris and electronic noise and thus remain undetectable. Certain modern high resolution instruments have extended the sensitivity range to be able to detect EVs to the about 200 nm EV size and about 10 fluorescent molecule detection limits, but there are no instruments currently capable of detecting, analyzing, and sorting sub-200 nm EVs based on the detection of a single epitope. Therefore, a need exists for enhancements in reagents and methods, such as flow cytometry, that would allow for the detection and quantification of single molecules, such as a single receptor on the surface of an EV.

SUMMARY

Although flow cytometers with sorting capabilities can be used to sort and study individual cells, no flow cytometer or similar instrument has been developed that can detect and sort nanomaterials smaller than 200 nanometers with single epitope sensitivity. To overcome this gap, the inventors developed multiparametric labels (referred to herein as molecular nanotags) that can be detected individually by modern high resolution flow cytometers and therefore enable the detection and sorting of small EVs or other nanobiological materials that would otherwise be too small or have too few epitopes for detection with standard methods, such as fluorescently labeled antibodies.

The compositions and methods disclosed herein overcome the prior barriers to functional sorting of nanoscale particles/vesicles and the detection of single molecules. Disclosed herein are nanoscale molecular tags that enable detection of single molecules by microscopy or a high resolution device that measures fluorescence and/or light scattering intensity (also referred to herein as light scattering power), such as a flow cytometer. The molecular tags can be used, for example, in a flow cytometer configured for high resolution detection. For example, see the nanoFACS method disclosed in U.S. Patent Application Publication No. 20130095575 and in Morales-Kastresana et al., *Scientific Reports*, 7:1878, 2017.

In some embodiments, the nanoscale molecular tag includes a core nanoparticle with a diameter of less than about 100 nm (such as less than 40 nm, or less than 20 nm, such as about 10 to 100 nm, 10 to 50 nm, or 40 to 80 nm, such as 10 nm, 20 nm, 30 nm, 40, nm, 50 nm, 60 nm, 70 nm, 80 nm, 90 nm, or 100 nm in diameter); an optional shell surrounding the core; and an armor having a first portion and a second portion, wherein the first portion is bound to the surface of the core nanoparticle, or if present, to the surface of the shell, and the second portion is not bound to the core nanoparticle or shell and includes a functionalized end with a fixed and/or quantifiable number of binding sites (for example, one). Any one of, or any combination of, the core, the shell, and the armor contribute to fluorescence, light scattering and/or target (e.g., ligand) binding properties of the molecular tag that are detectable by a high resolution device that measures light scattering intensity above the level of the reference noise of a particular instrument, as in a flow cytometer device. For example, elastic light scattering intensity of a disclosed molecular nanotag allows the assembled structure to be detectable above the level of the limits of detection for (elastic) light scattering (commonly referred to as side or forward scatter), and the fluorescence or Raman scattered light intensity permits the assembled structure to have sufficient brightness for detection above the limits of detection of inelastically scattered light for the instrument, and the target (e.g., ligand) specificity permits the identification and characterization of a broad spectrum of nanoscale biological targets. A disclosed molecular nanotag having at least one of those multiparametric features allows its detection as an individual molecular nanotag by the instrument, and thus the disclosed molecular nanotags can be used to detect EVs with a few as one epitope or ligand.

In other more specific examples, the nanoscale molecular tag includes a core nanoparticle with a diameter of less than 100 nm; an optional shell; and an armor (such as a polymer)

having a first portion and a second portion. The first portion of the armor includes covalent binding sites that attach the armor to the surface of the core nanoparticle, which reduces nanoparticle valency to a fixed number (for example, one) of functional binding sites; a second portion that provides a linker to connect armor binding site(s) to a functional ligand for a designated or preselected target; and a functional ligand (comprised of protein, nucleotide, or other ligand-binding element) for a designated target, and wherein any one of, or any combination of, the core, the shell and the armor contribute to fluorescence, light scattering and/or ligand binding properties of the molecular tag that are detectable by a microscopy or a high resolution device that measures fluorescence and light scattering intensity. In other more specific examples, the core comprises a quantum nanocrystal (with an optional shell) having a high refractive index, surface geometry or other attributes that contribute to light scattering properties that are detectable by a flow cytometer, and the armor is a polymer capable of specifically binding to a binding partner or target ligand.

The disclosed molecular tags provide the ability to detect single nanoparticles, such as quantum nanocrystals, and targets to which the molecular tags are bound. By combining different molecular tags, it is possible to detect and sort nanoscale particles, and also to detect and count individual molecular components of the nanoscale particles, such as surface receptors on cells or EVs. The molecular tags are capable of having a controlled valence (for example monovalence) that binds to individual corresponding targets of interest. Such valence-controlled binding enables counting numbers of bound molecules, for example in shifted peaks of detected signals, for example in a flow cytometer output or using other methods that detect concurrent light scatter and fluorescence detection. The capacity for single molecule detection has broad biomedical, biodefense, industrial, environmental and other applications. For example, the molecular tags can be used to detect and determine the number of specific molecules of biologically relevant subsets of extracellular microvesicles and viruses with good fidelity, and with the capability to isolate the relevant subsets. In other examples, biomarkers (including biosignatures) can be detected that are associated with radiation exposure, disease detection, clinical prognosis, or selection of a therapeutic treatment or protocol.

Also provided is a method for detecting a target in an instrument that enables concurrent light scatter and fluorescence detection (such as a flow cytometer). The target can, for example, be a single target molecule in a sample. In some examples, the method includes contacting the sample with a nanoscale molecular tag disclosed herein, wherein the functionalized end of the nanoscale molecular tag specifically binds the target molecule if present in the sample; and analyzing the sample using an instrument configured for resolution of small particles to detect individual nanoscale molecular tags bound to the target molecule by detection of side scatter or detection of fluorescence, or both.

Another aspect of the disclosure is a method of detecting extracellular vesicles (EVs) or other submicron particles bearing a tumor antigen using the molecular nanotags in which the functional ligand is specific for the tumor antigen, and then detecting the stained particles using microscopy or a high resolution device that measures fluorescence and/or light scattering and intensity. By way of example and not limitation, the tumor antigens may be PSMA, mesothelin, EpCam, HER2, EGRF, CD24, CD133, CD47, CD147, PD-L1, GPC-1 or Muc-1, or other markers described later in the detailed specification. Alternatively, the method detects EVs or other submicron particles bearing an infectious pathogen antigen, such as a viral antigen, using molecular nanotags in which the functional ligand is specific for the viral antigen. For example and without limitation, the viral antigens are derived from HIV, hepatitis C virus, hepatitis B virus, human papillomavirus (HPV), HTLV-I, Epstein-Barr virus, or those described later in this specification. In yet other embodiments, the method detects an immune system cell antigen or marker in which the functional ligand is specific for the immune system antigen or marker. For example and without limitation, the immune system antigens or markers are MHC class II antigens, PD-L1, CD80, CD86, CD83, CD11c, CD11b, CD3, CD4, CD8, CD19, CD20 or other markers described herein. In another embodiment, the method detects EVs or other submicron particles bearing a disease antigen or marker, for example and without limitation, markers for Alzheimer's disease, multiple sclerosis, rheumatoid arthritis, diabetes mellitus, inflammatory bowel disease, rheumatological diseases, inflammatory diseases, endocrine diseases, gastrointestinal diseases, neurological diseases, autoimmune diseases, cardiovascular diseases, or renal diseases, or other markers described later in this specification.

Because the disclosed molecular nanotags are modular in their design, a set of molecular nanotags with modular combinations of core, armor, and ligand-binding components can be assembled to produce a multiplex molecular nanotag array, where multiple types of molecular nanotags, each with distinctive attributes in terms of elastic and inelastic light scattering properties, and each type with a unique ligand specificity can be used detect a plurality of different targets simultaneously or contemporaneously. When used with a sorting flow cytometer, the molecular nanotags enable sorting and downstream analysis of specific subpopulations of EVs or other targets, based on the specific binding of each molecular nanotag to as few as one specific ligand/epitope, for use in additional downstream assays. Thus, in some examples, the disclosed methods are multiplexed, in that several different ligand-associated EVs are detected simultaneously or contemporaneously (for example EVs containing different target molecules on their surfaces can be detected simultaneously or contemporaneously with the disclosed molecular nanotags, such as with a plurality of different molecular nanotag populations, each specific for a particular target EV population). In some examples, the method is multiplexed, and at least 2, at least 3, at least 4, at least 5, at least 10, at least 20, at least 30, at least 40, or at least 40 different molecular nanotag populations are used with the disclosed methods, for example to detect a plurality of different targets (e.g., antigen, EV marker, and combinations thereof).

The foregoing and other objects and features of the disclosure will become more apparent from the following detailed description and examples that are provided for illustration only, and which proceeds with reference to the accompanying figures. The detailed examples satisfy the requirement to enable others to make and use the invention without limiting the scope of the invention.

BRIEF DESCRIPTION OF THE DRAWINGS

At least some of the following figures are submitted in color:

FIGS. 1A-1B: Schematic drawings of exemplary molecular nanotags. FIG. 1A illustrates molecular nanotags include a core particle 10 having a high complex refractive index (RI), such as a quantum nanocrystal or other high complex RI nanomaterial (such as silver or gold), and an "armor" 12, such as thiolated single-stranded DNA with a single functionalized DNA end. The functionalized DNA end 14 serves as a "Lock" (or a binding site for a "Lock") which can bind a specific "Key," such as a target ligand. Using the nanoFACS method, single particles can be resolved by side scattered (SSc) and/or fluorescent light and monovalent nanotags enable single molecule ligand enumeration. Alternatively, the single particles can be imaged by microscopy or other optical methods (e.g., nanoparticle tracking or SERS, see for example Stremersch et al., *Small* 12:3292-301, 2016). FIG. 1B shows an example of a monovalent armored quantum nanocrystal (such as a QDOT®) 20 with a thiolated single-stranded DNA armor 12 and single functionalized DNA end 14. The armored quantum nanocrystals can also be used in tandem using complementary DNA ends.

FIG. 1C schematically illustrates monovalent quantum nanocrystals of the type that were disclosed in Farlow et al., *Nat. Methods* 10(12): 1203-1205 (2013), which is incorporated by reference. The monovalent quantum nanocrystals of Fowler et al. are not detectable as single particles by high resolution flow cytometry such as NanoFACS. The particles are only detected if they are run in massive excess such that they are detected as "swarms" of multiple coincident particles in the laser intercept. The figure also illustrates variations of that prior approach to produce molecular composite structures that can selectively bind to targets.

FIG. 1D schematically illustrates in the top panel a molecular nanotag 30 in accordance with the present disclosure that includes a quantum nanocrystal 10 with an armor 12 (e.g., a monovalent thiolated DNA armor, a monovalent polyadenylated DNA armor (Yao et al., *NPG Asia Materials* 7:e159, 2015); or a stoiciometric ratio of armor molecules that includes 1 functional ligand per total bound surface molecules (e.g., see Leduc et al., *NanoLetters* 13:1489-94, 2013)) that is linked at one end 14 to a first binding partner 16 (e.g., label or tag) that specifically binds to a second binding partner (e.g., target, such as protein, such as a ligand) 18. Also depicted in the bottom panel is a variation of the concept in which a first armored quantum nanocrystal 40 is linked to a second quantum nanocrystal 50, which is linked to a first binding partner 16 (e.g., label or tag) that specifically binds the second binding partner (e.g., target, such as protein, such as a ligand) 18. In one example, a monovalent armor design ensures 1-to-1 ligand-to-label binding and correspondence of enumerated label number with measured target (EV epitope) number. However, for the purposes of detecting as few as one target epitope, polyvalent surface chemistries, such as streptavidin or thiol-PEG (Duchesne et al., *Langmuir* 24:13572-80, 2008) can be used for the armor.

FIG. 2: A plot of predicted scattered light intensity (lines, based on Mie Theory as modeled with MiePlot, philliplaven.com) versus detected scattered light intensity with AstriosEQ configured for nanoFACS, showing that materials. Curves and the left axis are a light scattering prediction model based on Mie theory with a 488 nm laser for EVs (RI=1.40), polystyrene beads (RI=1.61) and silica beads (RI=1.46), and with water as the medium (RI=1.33). Dots in the curves represent empirical median (with standard deviation) intensity measurements actual particles analyzed on the Astrios EQ instrument, to show how they fit compared to the scatter that was mathematically predicted by Mie models. Gold particles (20 nm-100 nm), for example, have higher predicted scattering intensity than materials such as polystyrene silia or EVs, due to quantum interaction of gold material with the incident laser light resulting in high complex refractive indices and plasmonic resonance.

FIG. 3: Detection of individual 29 nm PEGylated QDOTS® by side scatter at 561 nm SSC and 488 SSC and fluorescence using the nanoFACS method.

FIG. 4: The disclosed molecular nanotags are a new class of labels that in some examples contain modular components that include a nanoscale light scattering element (the core nanoparticle in one depicted embodiment, e.g., 10 in FIG. 1B), that scatters light in an elastic manner (at the same wavelength range as the incident light), a may include an element that also scatters light in a specific inelastic manner (a fluorophore or a raman scattering molecule) (which can also be a component that contributes scattering intensity if the core nanoparticle is a quantum nanocrystal or similar component that produces both elastic and inelastic scattering spectra) and a monovalent linker for target detection, as in Farlow et al., *Nat. Methods* 10(12): 1203-1205 (2013). The molecular nanotags allow detection of a single molecule on the surface of a single nanoscale sized vesicle. Detection of 29-nm PEGylated QDOTS®. QDOTS® are observed at and above the scattered light noise floor, in addition to being fully resolved as individual (single molecule) particles by fluorescence, when using the disclosed nanoFACS method on the AstriosEQ. PBS alone was used to delineate the instrument noise. Also shown are vendor-provided QDOT® specifications of the PEGylated QDOTS® tested with the nanoFACS system.

FIG. 5: Detection of prostate specific membrane antigen (PSMA) expression on extracellular vesicles (EVs) from prostate cell lines by bulk analysis (using bead-based flow cytometry) and by single EV analysis.

FIG. 6A is a series of four graphs showing the relationship between refractive index and wavelength for four representative different materials with distinctive light scattering properties.

FIG. 6B shows plotted data obtained from public database (refractiveindex.info). Gold is one specific example of a high complex refractive index material that can be used in a molecular nanotag to increase the reflectivity of the quantum nanocrystal to increase elastic light scattering and improve detection above the level of background noise. At 405 nm, the refractive index is 1.5236 and the extinction coefficient is 1.8409.

FIGS. 7A-7B: (A) Manufacturer absorption specifications for gold nanospheres and gold nanourchins. (B) Gold standard nanoparticles (top) and Gold NanoUrchins (bottom) are available in various sizes, such as from 15 nm to 100 nm. What distinguishes gold nanospheres from gold nanourchins is their surface geometry, and how this surface interacts with light. Gold nanoparticles and NanoUrchins can be used to achieve distinctive absorption and light scattering patterns, which lead to the visible appearance that these materials in solution are different colors, despite being composed of the same material (gold) and despite being the same mean diameter. Because these materials can be resolved as individual objects and because they have distinctive light scattering spectra, they can be distinguished not only by diameter, but also by their light absorbance and scattering profiles. Thus nanomaterials such as gold nanospheres or gold nanourchins can be used as the core particle (e.g., 10 in FIG. 1B) having a high RI in the disclosed molecular nanotags, they can be used in a multiplex fashion to identify different specific ligand-associated EVs. Moreover, since surface geometry and particle size differences lead to different light scattering properties, the use of these different materials as cores in molecular nanotags with different epitope specificity allows for the stratification of sets of labels based on the light scattering properties of the core material, in the same manner that stratification based on fluorescence is commonly used in multiplex label set assays (Krutzkik et al., Chapter 6, Unit 6.31, *Current Protocols in Cytometry*, 2011).

FIG. 8: Comparison of observed optical characteristics for gold nanospheres versus gold NanoUrchins. Comparison of gold nanoparticles (left), Gold NanoUrchins (middle) and polystyrene beads (right) (all 100 nm). Refractive index at different wavelengths of component materials are determined as described by methods described in Gardiner et al. (*J Extracell Vesicles* 3:25361, 2014, incorporated by reference). Both gold NanoUrchins and gold nanospheres in this example have a derived RI at this method of about 1.4 or above, but, as can be seen in the NanoSight video screen shot (bottom), the visible light seen with gold nanourchins is greater than the gold nanospheres of the same size, due to greater scattered light diffraction from the surface of the gold nanourchins. Differences in light diffraction lead to one visible difference in the scattered light characteristics between these nanomaterials, and the other is absorbance and plasmonic resonance as indicated in FIG. 7A.

FIG. 9: A schematic representation of modular components of the molecular nanotags disclosed herein, which in some examples include a strong fluorescent component, a light scattering component, and a ligand-specific binding component. The strongly fluorescent component has, for example, a fluorescence of greater than 100 MESF (Molecules of Equivalent Soluble Fluorochrome (MESF), a component with strong and distinctive light scattering characteristics, and is resolvable with FSC or SSC on a flow cytometer), and a ligand-specific binding component such as an aptamer, affimer, antibody, or small molecule ligand).

FIG. 10A provides small molecule prostate specific membrane antigen (PSMA) ligands that can be used with the disclosed molecular nanotags (e.g., 14 in FIG. 1B, see FIGS. 11A-11F).

FIG. 10B provides a second synthetic PSMA ligand, Biotin-PEG-amide-PSMA CCW-II-372 (e.g., 14 in FIG. 1B).

FIG. 10C provides a third synthetic PSMA ligand, biotin-PEGS-PSMA CCW-II-361, synthesized by the NCI Image Probe Development Core, for use with the disclosed molecular nanotags (e.g., 14 in FIG. 1B).

FIGS. 11A-11F contrast monovalent quantum nanocrystal constructs (left) to a prior quantum nanocrystal-SA-mAb (right) in the context of PSMA-specific molecular nanotags. Such polyvalent labels (FIG. 11F) constructed as molecular nanotags provide sensitivity to detect single epitopes on EVs but not afford 1-to-1 binding stoichiometries that are most useful for epitope counting or enumeration per EV. (A) is an example of a generic core and monovalent armor, (B-D) illustrate end terminal biotiylated armor that functions as a ligand for streptavidin, for coupling to a biotinylated target-binding molecule, such as biotinylated antibody (B), biotinylated aptamer (C), or biotinylated small molecule ligand (D). (E) depicts an azidated monovalent polymer on the surface of the nanoparticle, which is conjugated by click chemistry to PSMA ligand DCBO-TEG. (F) shows a representative conventional polyvalent streptavidin QDot, used to bind to biotinylated molecules, including anti-PSMA antibody bound to EVs, as shown in FIG. 18. The design of FIG. 11B can also be comprised of a synthetic oligonucleotide wherein the PSMA-binding aptamer sequence is contiguous with the "armor"-ing sequence that binds to either the core surface or shell.

FIG. 12A depicts the structure of three PSMA-binding aptamers for use with the molecular nanotags (SEQ ID NOS: 1-3). The PSMA-binding aptamer sequence was, in specific examples, included at the terminal end of the armor DNA.

FIG. 12B demonstrates use of the A9g, with the addition of a 5'-TEG spacer to detect surface expression of PSMA (right).

FIG. 12C provides a schematic diagram of modifications made to the A9g to facilitate use as a ligand for a label.

FIG. 12D provides a schematic diagram of the incorporation of this A9g aptamer as an end, ligand-binding element 14 into the molecular nanotag armor sequence 12.

FIGS. 13A-13E demonstrate that undercounting of molecular nanotags can be decreased by increasing the shell depth of the nanotag from a conventional depth of less than 6 nm to a shell depth of greater than 10 nm, for example 10-20 nm. Example from Single-NQD photoluminescence studies. (A) On-time histogram of a CdSe/19CdS g-NQD population constructed from analysis of typically >100 individual g-NQDs. An example fluorescence time trace (used to prepare a histogram) for an individual CdSe/19CdS g-NQD is shown in the inset to (A). (B) Plot of 'percent NQD population' versus the number of CdS shell monolayers for different on-times. Two preparations/analyses are plotted for the 10-, 16-,and 19-shell systems, providing an indication of experimental variability in (B). (C) Photobleaching behavior: plots of emitting NQD fractions over time are presented for CdSe/5CdS (top left), CdSe/10CdS (top right), CdSe/15CdS (bottom left), and CdSe/19CdS (bottom right) core/shell NQDs. Comparison of percent-NQD population versus shell thickness as a function of the total observation time (0.5, 5, and 54 minutes) for NQDs 'on' ≥99% of the observation time ('non-blinking' population) (D) and ≥80% of the observation time ('largely non-blinking' population) (E).

FIGS. 14A-14D illustrate the configuration of an AstriosEQ for performing nanoFACS. (A) Side scatter laser light trajectories (dashed lines), alongside their corresponding fluorescent detection paths solid lines in orthogonal, not forward, detection path). This schematic demonstrates the stream of sheath fluid, with core stream and sample particles (represented by dots in the center of the stream), intercepted by the four lasers used in these studies. Each laser generates not only a characteristic ring of diffraction but also dim, diffuse scattered light (shown here for the green laser only, to illustrate). (B) Images of the AstriosEQ interrogation chamber, with the laser intercepts the stream in an aligned position, demonstrate the presence of diffusely scattered light when the stream is off, which is brighter, along a ring of diffraction around the plane of the laser intercept (along the chamber walls and door), when the stream is turned on. Using an LED pulser (C), relative comparisons of the noise floor on candidate trigger channels, using the LED pulser as an optical trigger (fixed pulse rate), in an isolated and unused PMT detector slot. (D): For analysis of submicron particles (100, 200, and 500 nm polystyrene beads) and comparison of resolution capabilities of each laser, a trigger/threshold was set with the 561ex-SSC channel to allow detection of diffusely scattered light, at a rate of 10-15 k events per second (eps), ~10-15% of the maximum sample eps rate. Side scatter signal detection demonstrated maximal small particle resolution on the 488ex-SSC channel while the 561ex-SSC provided the best signal:noise separation on this instrument.

FIGS. 15A-15I illustrate extracellular vesicle (EV) analysis, sorting, and reanalysis with nanoFACS. Along with 100 nm Fluospheres (A), for comparison, EVs from a dendritic cell line (DC2.4) and breast carcinoma cell line (4T1) were characterized with NanoSight NTA (B and C) and nanoFACS (D, E and F, respectively). Reference noise (red-dashed box), was monitored alongside the data for the events/materials detected above the level of the noise (green-dashed box). Tumor and immune EV populations from 4T1 and DC2.4 cell lines were labeled with carboxyfluorescein succinimidyl ester (CFSE; Invitrogen) and CellTracker Violet (Invitrogen), respectively. Unbound labels were removed with NAP-5 (GE Healthcare) size exclusion chromatography; the EV populations were mixed, then analyzed and sorted, with sort gates shown (G). Sorted EV samples were concentrated with centrifugal concentration (Amicon Ultra-15, 10 k NMWL), and re-analyzed (H and I). Reanalyzes demonstrate >95% purity (calculated with the number of reanalysis events in the positively selected gate, divided by the sum of reanalysis events in the negatively selected gate and double positive gate), with only the sorted EVs, not the negatively selected EVs, observed above the reference noise.

FIGS. 16A-16E illustrate the spectral scatter properties of (A) 20 nm, (B) 40 nm, (C) 60, nm (D) 80, and (E) 100 nm particles in the UV-visible spectrum from 300-800 nm of a variety of compositions including gold, silver, polystyrene, platinum, titanium dioxide, iron oxide, and copper.

FIG. 17A-17B illustrate (A) the cross-sectional scatter characteristics of 40 nm gold and silver nanoparticles, modelled using Mie theory with published refractive indices and extinction coefficients. Vertical lines depict the illumination wavelengths of the AstriosEQ flow cytometer. (B) raw data of acquired 40 nm gold (blue) and 40 nm silver (red) on 405, 488, 561 and 640 nm scattering channels.

FIG. 18 illustrates detection of extracellular vesicles (EVs) labelled with quantum dots (Qdots) using flow cytometry.

Figure 22A:
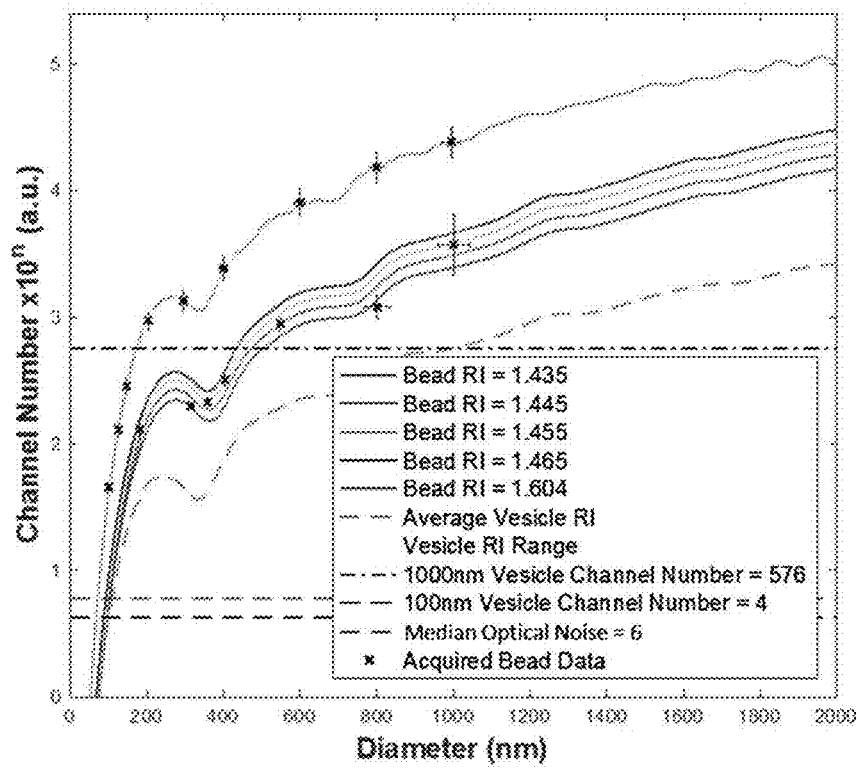
Figure 22B:
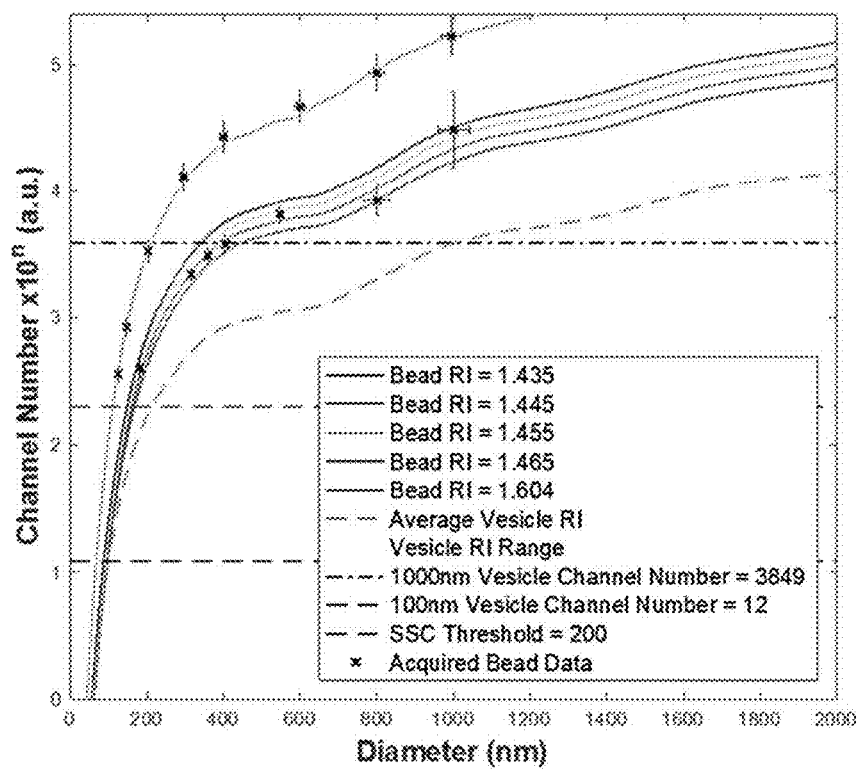

FIGS. 22A-22B illustrate the modeling of spherical particles using mie theory with refractive indices representing polystyrene (Bead RI=1.604), silica (Bead RI=1.435-1.465) and extracellular vesicle range (green) using the collection optics of the (A) Astrios EQ (24A) and (B) FACS Symphony flow cytometers. Overlaid on each figure at the acquire polystyrene and silica bead data relating to the modelled spherical particles. Y-axis represents the arbitrary unit scales of a flow cytometer, with predicted data in absolute units being normalized to arbitrary units. The channel number for 100 nm and 1000 nm average RI extracellular vesicles are shown with black dashed lines. Threshold and system noise highlighting limit of instrument detection is depicted with red dashed line.

FIGS. 23A-23D illustrate detection by flow cytometry analysis of (A) 38 different bead populations, each population having different amounts of red and green label (P1 and P2 parameters as shown). (B) capture and detection of EVs from plasma with the 38 bead set and a labeled antibody specific for a different EV epitope to identify three bead populations bound to EVs with that epitope. (C) Illustrates the use of molecular nanotags to generate a multiplex EV analytical array that allows for single epitope and single EV sensitivity. (D) Comparison of miRNA profiles of EVs sorted based on detection of PSMA on the EVs, versus the bulk EV population miRNA or miRNA of PSMA-negative EVs.

SEQUENCE LISTING

The nucleic sequences are shown using standard letter abbreviations for nucleotide bases, as defined in 37 C.F.R. 1.822. Only one strand of each nucleic acid sequence is shown, but the complementary strand is understood as included by any reference to the displayed strand. The sequence listing generated on Mar. 29, 2019 13 Kb, and submitted herewith, is herein incorporated by reference.

SEQ ID NO: 1 is a A10-3.2 PSMA aptamer sequence.

SEQ ID NO: 2 is a A9g PSMA aptamer sequence.

SEQ ID NO: 3 is a A9g.6 PSMA aptamer sequence.

For SEQ ID NOS: 4-13 below, Phosphorothioated DNA=A*, G*, T*; RNA=rA, rCi, rC, rU; Phosphorothioated RNA=rA*, rG*, rC*, rU*; 2' O-Methyl RNA=mA, mG, mC, mU; Phosphorothioated 2' O-Methyl RNA=mA*, mG*, inC*, mU; Locked Nucleic Acid (LNA)=+A, +G, +C, +T (available on dual labeled probes only); 3' Biotin-TEG (tetraethylene glycol)=/3BioTEG/; Internal 2'-Fluorodinated Uridine=i2FU/; 32FU=a 3' 2-fluorouridine; 5Biosg—a biotin with single glycol linker in the 5' position; DBCO dibenzocylcloctyl=click attachment; Mixed Bases=bases in UPPERCASE (Also see www.idtdna.com/pages/support/technical-vault/reading-room/quick-reference/all-modifications)

| Name | Oligo Sequences for mQDots |
|------|---------------------------|
| Standard sequence with A9g ending (SEQ ID NO: 4) | A*A*A*A*A*A*A*A*A*A*A*A*A*A*A*A* A*A*A*A*A*A*A*A*A*A*A*A*A*A*A*A* A*A*A*A*A*A*A*A*A*A*A*A*A*A*A*A* A*A*CTCTCTCTCTCTCTCTCTCTrGrGrG rAr/I2FC/r/I2FC/rGrArArArArArGr Ar/I2FC/r/I2FC/r/I2FU/rGrAr/I2 FC/r/I2FU/r/I2FU/r/I2FC/r/I2FU/ rAr/I2FU/rAr/I2FC/r/I2FU/rArAr Gr/I2FU/r/I2FC/r/I2FU/rAr/I2FC/ rGr/I2FU/r/I2FU/r/I2FC/r/I2FC/ r/I2FC/ |
| Standard sequence with A10-3-2 ending (SEQ ID NO: 5) | A*A*A*A*A*A*A*A*A*A*A*A*A*A*A*A* A*A*A*A*A*A*A*A*A*A*A*A*A*A*A*A* A*A*A*A*A*A*A*A*A*A*A*A*A*A*A*A* A*A*CTCTCTCTCTCTCTCTCTCTrGrGrG rArGrGrA/i2FC/rGrA/i2FU/rG/i2FC /rGrGrA/i2FU//i2FC/rArG/i2FC// i2FC/rA/i2FU/rG/i2FU//i2FU// i2FU/rA/i2FU/rG/i2FU//i2FC/rA/ i2FC//i2FU//i2FC//i2FC//32FU/ |
| Standard sequence with Biotin ending (SEQ ID NO: 6) | A*A*A*A*A*A*A*A*A*A*A*A*A*A*A*A* A*A*A*A*A*A*A*A*A*A*A*A*A*A*A*A* A*A*A*A*A*A*A*A*A*A*A*A*A*A*A*A* A*A*CTCTCTCTCTCTCTCTCTCT/iAmM C6T//3BioTEG/ |

-continued

| Name | Oligo Sequences for mQDots |
|---|---|
| Standard sequence with Azide ending (SEQ ID NO: 7) | A*A*A*A*A*A*A*A*A*A*A*A*A*A*A*A* A*A*A*A*A*A*A*A*A*A*A*A*A*A*A*A* A*A*A*A*A*A*A*A*A*A*A*A*A*A*A*A* A*A*CTCTCTCTCTCTCTCTCT/ 3AzideN/ |
| A9g Aptamer with 5' Biotin-TEG (SEQ ID NO: 8) | /5Biosg//i2FU/rGrGrGrA/i2FC//i2 FC/rGrArArArArArGrA/i2FC//i2FC //i2FU/rGrA/i2FC//i2FU//i2FU// i2FC//i2FU/rA/i2FU/rA/i2FC//i2 FU/ArArG/i2FU/ /i2FC//i2FU/ /rA/i2FC/rG/i2FU//i2FU//i2 FC//i2FC//32FC/ |
| A10-3-2 Aptamer with 5' Biotin-TEG (SEQ ID NO: 9) | /5BiotinTEG/rGrGrGrArGrGrA/i2 FC/rGrA/i2FU/rG/i2FC/rGrGrA/ i2FU//i2FC/rArG/i2FC//i2FC/ rA/i2FU/rG/i2FU//i2FU//i2FU/ rA/i2FC/rG/i2FU//i2FC/r A/i2 FC//i2FU//i2FC//i2FC//32FU/ |
| A9g Aptamer with 5' Biotin (SEQ ID NO: 10) | /5Biosg/r/I2FU/rGrGrGrA/i2 FC//i2FC/rGrArArArArArGrA/ i2FC//i2FC//i2FU/rGrA/i2FC// i2FU//i2FU/i2FC//i2FU/rA/ i2FU/rA/i2FC/ /i2FU/rArArG/ i2FU//i2FC//i2FU/rA/i2FC/rG/ i2FU//i2FU//i2FC//i2FC//32FC/ |
| A10-3-2 Aptamer with 5' Biotin (SEQ ID NO: 11) | /5Biosg/rGrGrGrArGrGrA/i2FC/ rGrA/i2FU/rG/i2FC/rGrGrA/i2F U//i2FC/rArG/i2FC//i2FC/rA/ i2FU/rG/i2FU//i2FU//i2FU/rA/ i2FC/rG/i2FU//i2FC/rA/i2F C//i2FU//i2FC//i2FC//32FU/ |
| A9g Aptamer with 5' Cu-Free Click (SEQ ID NO: 12) | /5DBCOTEG/r/I2FU/rGrGrGrA/ i2FC//i2FC/rGrArArArArArAr GrA/i2FC//i2FC//i2FU/rGrA/ i2FC//i2U//i2FU//i2FC// Fi2FU/rA/i2FU/rA/i2FC//i2 FU/rArArG/i2FU/ /i2FC//i2FU/ rA/i2FC/rG/i2FU//i2FU//i2 FC//i2FC//32FC/ |
| A10-3-2 Aptamer with 5' Cu-Free Click (SEQ ID NO: 13) | /5DBCOTEG/rGrGrGrArGrGrA/i2 FC/rGrA/i2FU/rG/i2FC/rGrGrA/ i2FU//i2FC/rArG/i2FC//i2FC /rA/i2FU/rG/i2FU//i2FU//i2 FU/rA/i2FC/rG/i2FU//i2FC/r A/i2FC//i2FU//i2FC//i2FC //32FU/ |

DETAILED DESCRIPTION

I. Abbreviations

EV extracellular vesicle
FSc forward scatter
nanoFACS nanoscale fluorescence activated cell sorting
PMT photomultiplier tube
PS polystyrene
PSMA prostate specific membrane antigen
QDOT® a commercially available quantum nanocrystal
SPD small particle detector
SPO small particle option
SSc or ss side scatter II. Terms and Methods Unless otherwise noted, technical terms are used according to conventional usage. Definitions of common terms (such as nucleotide, DNA, RNA, aptamer, probes, extracellular vesicles and many more may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references incorporated herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Aptamer: Nucleic acid aptamers are single-stranded DNA or RNA (ssDNA or ssRNA) molecules that can bind to pre-selected targets such as proteins and peptides with high affinity and specificity. Peptide aptamers are artificial proteins selected or engineered to bind specific target molecules.

Armor: With reference to the molecular nanotags disclosed herein, the armor refers to a polymer on the surface of the core nanoparticle that substantially covers the surface of the nanoparticle and protects it from binding to other polymers to which binding is not desired by excluding them from binding. In some instances the exclusion is steric exclusion. The armor therefore helps assure a controlled valence of the armored nanoparticle, for example monovalence.

Avidin/Streptavidin: The extraordinary affinity of avidin for biotin allows biotin-containing molecules in a complex mixture to be discretely bound with avidin. Avidin is a glycoprotein found in the egg white and tissues of birds, reptiles and amphibia. It contains four identical subunits having a combined mass of 67,000-68,000 daltons. Each subunit consists of 128 amino acids and binds one molecule of biotin. Extensive chemical modification has little effect on the activity of avidin, making it especially useful for protein purification.

Another biotin-binding protein is streptavidin, which is isolated from *Streptomyces avidinii* and has a mass of 60,000 daltons. In contrast to avidin, streptavidin has no carbohydrate and has a mildly acidic pI of 5.5. Another version of avidin is NEUTRAVIDIN™ Biotin Binding Protein (available from Pierce Biotechnology) with a mass of approximately 60,000 daltons.

The avidin-biotin complex is the strongest known non-covalent interaction ($Ka=10^{15}$ $M^{-1}$) between a protein and ligand. The bond formation between biotin and avidin is very rapid, and once formed, is unaffected by extremes of pH, temperature, organic solvents and other denaturing agents.

Streptavidin can be substituted with other types of avidin. The term "avidin" is meant to refer to avidin, streptavidin and other forms of avidin (such as derivatives or analogs thereof) that have similar biotin binding characteristics. Analogs or derivatives of avidin/streptavidin include, but are not limited to, nitro-streptavidin, non-glycosylated avidin, N-acyl avidins (such as N-acetyl, N-phthalyl and N-succinyl avidin), and the commercial products EXTRAVIDIN™ (Sigma-Aldrich), Neutralite Avidin (SouthernBiotech) and CaptAvidin (Invitrogen). Additional avidin/streptavidin analogs and derivatives are known in the art (see, for example, U.S. Pat. No. 5,973,124 and U.S. Patent Application Publication Nos. 2004/0191832; 2007/0105162; and 2008/0255004).

Binding partner: A member of a pair of molecules that interact by means of specific, non-covalent interactions that depend on the three-dimensional structures of the molecules involved. Exemplary pairs of specific binding partners include antigen/antibody, hapten/antibody, ligand/receptor, nucleic acid strand/complementary nucleic acid strand, substrate/enzyme, inhibitor/enzyme, carbohydrate/lectin, biotin/avidin (such as biotin/streptavidin), and virus/cellular receptor.

Biomarker: A measurable substance in an organism, the presence of which is indicative of observable characteristics (phenotype) of an organism. Biomarkers can be used to measure the presence of disease, the progress of disease and/or the effects of treatment. A variety of biomarkers are known in the field, and include circulating biomarkers such as a vesicle, micro dA or protein present in a biological sample. Characterizing a phenotype for a subject or individual may include, but is not limited to, the diagnosis of a disease or condition, the prognosis of a disease or condition, the determination of a disease stage or a condition stage, a drug efficacy, a physiological condition, organ distress or organ rejection, disease or condition progression, therapy-related association to a disease or condition, or a specific physiological or biological state.

Biotin: A molecule (also known as vitamin H or vitamin $B_7$) that binds with high affinity to avidin and streptavidin. Biotin is often used to label nucleic acids and proteins for subsequent detection by avidin or streptavidin linked to a detectable label, such as a fluorescent or enzymatic reporter molecule. Biotinylation of a molecule (such as an antibody or other protein sample) is routinely achieved in the art by reacting a free carboxyl group on biotin with an amine group on a protein, such as an amine group found in an antibody or protein analyte/analog. Unless indicated otherwise, the term "biotin" includes derivatives or analogs that participate in a binding reaction with avidin. Biotin analogs and derivatives include, but are not limited to, N-hydroxysuccinimide-iminobiotin (NHS-iminobiotin), amino or sulfhydryl derivatives of 2-iminobiotin, amidobiotin, desthiobiotin, biotin sulfone, caproylamidobiotin and biocytin, biotinyl-ε-aminocaproic acid-N-hydroxysuccinimide ester, sulfo-succinimide-iminobiotin, biotinbromoacetylhydrazide, p-diazobenzoyl biocytin, 3-(N-maleimidopropionyl) biocytin, 6-(6-biotinamidohexanamido)hexanoate and 2-biotinamidoethanethiol. Biotin derivatives are also commercially available, such as DSB-X™ Biotin (Invitrogen). Additional biotin analogs and derivatives are known (see, for example, U.S. Pat. No. 5,168,049; U.S. Patent Application Publication Nos. 2004/0024197, 2001/0016343, and 2005/0048012; and PCT Publication No. WO 1995/007466).

Biotin binding protein: A protein that binds biotin with sufficiently great affinity for an intended purpose. Examples of biotin binding proteins are well known in the art, and include avidin, streptavidin, NEUTRAVIDIN™, and monoclonal antibodies or receptor molecules that specifically bind biotin. In the context of this disclosure, streptavidin could be replaced with any other biotin-binding proteins, or a combination of biotin binding proteins.

Click conjugation: Conjugation using "click" chemistry, which is a term that describes chemical reactions that are modular, wide in scope, give very high yields, and generate only inoffensive byproducts. One example of a "click" reaction is the Huisgen copper(I)-catalyzed azide-alkyne 1,3-dipolar cycloaddition (CUAAC) which yields a 1,4-disubstituted five-membered 1,2,3-triazole ring. This reaction between azides and alkynes offers high yields and involves functionalities that can be introduced relatively easily in a variety of molecules such as: synthetic polymers, fluorophores, small molecules or into specific locations in biomolecules. A positive aspect of this reaction for biological purposes is that the azide and alkyne functional groups are largely inert towards biological molecules and aqueous environments. More recently copper-free click conjugation has become available, using DCBO-TEG and azidated linkers.

Conjugated: Refers to two molecules that are bonded together, for example by covalent bonds. An example of a conjugate is a molecule (such as avidin/streptavidin) conjugated to a detectable label, such as a fluorophore, to form a detection substrate.

Contacting: Placement in direct physical association; includes both in solid and liquid form. As used herein, "contacting" is used interchangeably with "exposed."

Control: A reference standard, for example a positive control or negative control. A positive control is known to provide a positive test result. A negative control is known to provide a negative test result. However, the reference standard can be a theoretical or computed result, for example a result obtained in a population.

Extracellular vesicles and Exosomes: Extracellular vesicle (EV), as used herein, is a membrane vesicle that is shed from cells. Such vesicles or membrane vesicles include without limitation: circulating microvesicles (cMVs), microvesicle, exosome, nanovesicle, dexosome, bleb, blebby, prostasome, microparticle, intralumenal vesicle, membrane fragment, intralumenal endosomal vesicle, endosomal-like vesicle, exocytosis vehicle, endosome vesicle. endosomal vesicle, apoptotic body, multivesicular body, secretory vesicle, phospholipid vesicle, liposomal vesicle, argosome, texasome, secresome, tolerosome, melanosome, oncosome, or exocytosed vehicle. Vesicles include spherical structures with a lipid bilayer similar to cell membranes which surrounds an inner compartment which can contain soluble components, sometimes referred to as the payload. Circulating EVs are particularly useful for diagnostic purposes.

In some embodiments, the methods disclosed herein make use of exosomes, which are small secreted vesicles of about 40-150 nm in diameter that are secreted by a wide range of mammalian cell types. Most exosomes studied to date have an evolutionary-conserved set of protein molecules and a set of tissue/cell type-specific proteins that distinguishes exosomes secreted by different cell types. The RNA molecules in exosomes include mRNA and miRNA, which can be shuttled from one cell to another, affecting the recipient cell's protein production. Exosomes are characterized in their biogenesis by formation of intraluminal vesicles (ILVs) through the inward budding of endosomes to form multivesicular bodies (MVBs). These MVBs then fuse with the outer cell membrane to release their cargo of ILVs (now exosomes) to the extracellular environment. The endosome is first formed by inward budding of the cell membrane by endocytosis and leads to inversion of the lipid membrane, trapping some of the extracellular environment on the intraluminal side. Similarly, the second inward budding of the endosome membrane traps a volume of the cell's cytoplasm and results in a positive orientation of the ILVs lipid membrane. When the ILVs (now exosomes) are released to the extracellular environment, they have the same orientation as the cell membrane and have been shown to display many of the surface markers from their cell of origin. However, the sorting process of membrane proteins during ILV formation is an active process, hence exosomal surface proteins are not a simple one-to-one representation of the surface markers from the cell of origin. Vesicles are membrane encapsulated structures that are shed from cells and have been found in a number of bodily fluids, including blood, plasma, serum, breast milk, ascites, bronchoalveolar lavage fluid and urine.

Vesicles can take part in the communication between cells as transport vehicles for proteins, RNAs, DNAs, viruses, and prions. Vesicles present in a biological sample provide a source of biomarkers, such as the markers present within a vesicle (vesicle payload), or that are present on the surface of a vesicle. Characteristics of vesicles (e.g., size, surface antigens, determination of cell-of-origin, payload) can also provide a diagnostic, prognostic or therapeutic indication. The use of vesicle biomarkers in disclosed, for example, in U.S. Patent Publication No. 20140228233, which discloses the detection of isolated vesicles comprising one or more mRNA such as A2ML1, BAX, C10orf47, C10orf162, CSDA, EIFC3, ETFB, GABARAPL2, GUK1, GZMH, HIST1H$_3$B, HLA-A, HSP90AA1, NRGN, PRDX5, PTMA, RABAC1, RABAGAP1L, RPL22, SAP18, SEPW1, SOX1, or any combination thereof. Other vesicle-associated markers include CA-125, CA 19-9, C-reactive protein (CRP), CD95, FAP-1, EGFR, E GFRvIII, EpCAM, apolipoprotein AI, apolipoprotein CIII, myoglobin, tenascin C, MSH6, claudin-3, claudin-4, caveolin-1, coagulation factor III, CD9, CD36, CD37, CD53, CD63, CD81, CD136, CD147, Hsp70, Hsp90, Rab13, Desmocollin-1, EMP-2, CK7, CK20, GCDF15, CD82, Rab-5b, Annexin V, MFG-E8, TIM-4, HLA-DR, miR200 microRNAs, or any combination thereof.

In some examples, the vesicle may be isolated from a biological sample from a subject who is being tested for, or is known to have, a condition such as cancer, for example a prostate cancer. Alternately, the vesicle may be isolated from a biological sample comprising a cell culture, for example a culture containing prostate cells. The disclosure of biomarkers in U.S. Patent Publication No. 20140228233 (see particularly Tables 1 and 2) is incorporated by reference herein, as is the disclosure of US 20140162888 which discloses additional biomarkers and biosignatures for diseases such as breast cancer, ovarian cancer, lung cancer, colon cancer, adenomalhyperplastic polyps, inflammatory bowel disease, colorectal cancer, prostate cancer, melanoma, brain cancer, cardiovascular disease, hematologic malignancies, hepatocellular carcinoma, cervical cancer, endometrial cancer, diabetes, Barrett's Esophagus, fibromyalgia, multiple sclerosis, Parkinson's Disease, Alzheimer's Disease, Prion diseases, sepsis, chronic neuropathic pain, schizophrenia, bipolar disorder, depression, gastrointestinal stroma tumor (GIST), renal cell carcinoma, cirrhosis, esophageal cancer, gastric cancer, autism, organ rejection, methicillin-resistant staphylococcus aureus, vunlerable plaque, and others. That incorporated disclosure also describes methods of identifying biosignatures to characterize a phenotype, screening proteins on vesicles which can be used as a biomarker on the vesicles, and methods of characterizing phenotypes by assessing vesicle biosignatures. Any of these methods can be used in association with the molecular nanotags disclosed in the, present specification.

For a review of membrane vesicles, including types and characterizations, see also Thery et al., *Nat Rev Immunol.* 2009 August; 9(8): 581-93;

Flow cytometry instrument: Includes any instrument that analyzes individual particles in a fluid mixture based on the particle's characteristics, such as size or fluorescence as the particle passes through a beam of coherent light, such as a laser beam for detection by an electronic detection device. It allows simultaneous multiparameter analysis of the physical and chemical properties of up to thousands of particles per second. The flow cytometer may be configured to detect fluorescence and the light scattering power of particles, and may also be configures for high resolution of particles, for example particles having a spherical equivalent diameter less than about 120 or 140 nm, or detection of nanoparticles having a spherical equivalent diameter less than 100 nm in diameter.

Fluorescence: Emission of light by a substance that has absorbed light or other electromagnetic radiation. Fluorescence intensity refers to a quantification of the intensity, which can be measured by any means known in the art, for example using ImageJ software available from the National Institutes of Health.

Fluorophore: A chemical compound, which when excited by exposure to a particular wavelength of light, emits light (i.e., fluoresces), for example at a different wavelength.

Examples of fluorophores that may be used in the methods disclosed herein are provided in U.S. Pat. No. 5,866,366 to Nazarenko et al.: 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; R-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N', N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999).

Other suitable fluorophores include GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof.

Fluorescent proteins include, but are not limited to, green fluorescent proteins (such as GFP, EGFP, AcGFP1, Emerald, Superfolder GFP, Azami Green, mWasabi, TagGFP, TurboGFP and ZsGreen), blue fluorescent proteins (such as EBFP, EBFP2, Sapphire, T-Sapphire, Azurite and mTagBFP), cyan fluorescent proteins (such as ECFP, mECFP, Cerulean, CyPet, AmCyanl, Midori-Ishi Cyan, mTurquoise and mTFP1), yellow fluorescent proteins (EYFP, Topaz, Venus, mCitrine, YPet, TagYFP, PhiYFP, ZsYellowl and mBanana), orange fluorescent proteins (Kusabira Orange, Kusabira Orange2, mOrange, mOrange2 and mTangerine), red fluorescent proteins (mRuby, mApple, mStrawberry, AsRed2, mRFP1, JRed, mCherry, HcRed1, mRaspberry, dKeima-Tandem, HcRed-Tandem, mPlum, AQ143, tdTomato and E2-Crimson), orange/red fluorescence proteins (dTomato, dTomato-Tandem, TagRFP, TagRFP-T, DsRed, DsRed2, DsRed-Express (T1) and DsRed-Monomer) and modified versions thereof.

Other fluorophores known to those skilled in the art may also be used, such as those that are commercially available from a variety of sources. Any of these fluorophores can provide fluorescence of the fluorescent component of the molecular nanotag.

NanoFACS: Configuration of a high resolution flow cytometer for analysis of nanomaterials, such that both light scattering measurements and fluorescence can be interrogated, using multiple lasers and parallel paths of detection, corresponding with those various lasers. Most flow cytometers only interrogate one side scatter channel, but with the Beckman Coulter AstriosEQ, for example, it is possible to trigger with one SSc detector and collect and use signal events from all other pinholes, including SSc parameters. In the example with the AstriosEQ, maximal SSc signal:noise separation was achieved by triggering with the SSc detector for the 561 nm laser at the center (fourth of seven) pinhole, followed by SSc analysis with the 488 nm detector at the second pinhole, which is the standard configuration for the AstriosEQ. This approach achieved a "partial transmission window" on the 488 nm SSc detector (FIGS. 14A-14D) and on the other "parallel" channels, to permit one to recognize and interrogate events, to evaluate a proportion of the particulate population that scatters with very low intensities, below the level that would have been set as the threshold on the parallel scatter channels, had the parallel channel been used as the trigger channel. The term "parallel subthreshold" events is used to describe these events (whether noise events or particle-associated events), which are detected on a parallel channel, but in a range that would have been below the threshold if that channel had been used as the trigger channel, with the same rate of reference noise as the determinant of parallel threshold levels. Because the reference noise rate was set on the channel with the primary (trigger) threshold when setting up the instrument, and this rate is set with sheath fluid only, the light:stream interactions that produce the scattered light that constitutes the majority of the background noise events in the reference noise. In this manner, it is possible to interrogate parallel subthreshold events from sheath fluid. When only sheath fluid was running, the parallel subthreshold rate roughly equaled the reference rate, or the rate of reflections off of the stream that were detected in the threshold channel. When running samples, the rate of the parallel subthreshold events increased as the rate of particle-associated light scattering events that was at or above the level of the threshold on the trigger channel increases. This is illustrated with the representative EV sample in FIG. 15A-15I. Lowering the threshold value to increase the reference noise rate increased the proportion of parallel subthreshold particles visualized (if present in the sample), since this maneuver increased the interrogation frequency for events that otherwise would not have been detected, based on their individual scatter properties.

Although there is the expected "blind" area below the level of the trigger on the 561 nm SSc channel, an informative (albeit only representative) population of parallel subthreshold events was detected on the 488 nm SSc channel. These events fell under the detection level that would have been excluded by a 488 nm threshold, had the 488 nm SSc channel been used as the trigger channel, but they were detected based on the correspondence of a 488 nm SSc signal, associated with the occurrence of an event at or above the 561 nm SSc threshold. Because the 561 nm trigger event may either be a noise event or a particle scattering event, observed sample events in the 488 nm SSc parallel subthreshold region overlapped with the reference noise detection region, and included not only signal events attributable to particles scattering light above the trigger threshold, but also parallel subthreshold signals that were recorded due to the coincidence of a light reflection from the fluid stream. The rate of the reference noise events (i.e., the rate of the events that arise due scattered laser light from the sheath fluid stream in the interrogation chamber that was intrinsic to the specific instrument and configuration for a particular experiment) remained constant when no particles were running and only sheath fluid was crossing the laser interrogation points. When a heterogeneous sample, such as plasma was analyzed, the rate is often not constant, and it was found that it was informative to interrogate the parallel subthreshold events and discern some attributes of the subthreshold population, such as rate and distribution, even though current software tools are unable to discriminate individual events arising due to light reflected from the fluid stream from individual particle detection events. Each of the 405 nm, 488 nm, 561 nm and 640 nm SSc detectors were compared and it was found that, for the purposes of setting a SSc trigger, the 561 nm channel provided the greatest sensitivity, whereas the 488 nm SSc channel provided the best signal:noise separation as a parallel SSc detector, in conjunction with the 561 nm SSc trigger on the AstriosEQ. We use the term Reference Noise to refer to both noise events at the threshold/trigger level (the threshold noise) and the parallel subthreshold noise events, collectively. Although these specific SSc channels are used for illustration, other forward or side scatter channels can be selected as the trigger and detector using the methods disclosed in this illustration.

Nanoparticle: A particle about 10 to about 100 nanometers (nm) in diameter. The disclosed nanotags can include a nanoparticle (e.g., 10 in FIG. 1A) composed of noble metal, such as gold or silver (or both), or materials other than a noble metal, such as $TiO_2$, silica, carbon, CdSe, ZnS or graphite, or any combination thereof.

Nanoscale: Having a diameter of about 100 nm or less, for example 10-100, such as 50-100 nm.

Noble metal: A metal that is resistant to corrosion and oxidation in air. They include ruthenium, rhodium, palladium, silver, osmium, iridium, platinum, and gold. Any reference herein to a noble metal can also include subsets or combinations of these metals, such as silver and gold. These are examples of materials that can provide a high refractive index material for use in the molecular nanotag, for example as a shell to a quantum nanocrystal.

Phenotype: The composite of an organism's observable characteristics.

Polymer: A natural or synthetic substance made up of repeating units, such as a macromolecule comprising repeating monomers. Polymeric molecules include, but are not limited to nucleic acid molecules, such as DNA, RNA, peptide nucleic acid (PNA), xeno-nucleic acid (XNA) and combinations thereof, protein polymers (such as microtubules or collagen), or synthetic linear polymers. A nucleic acid polymer can be either single-stranded or double-stranded. The disclosed nanotags can include an armor composed of a polymer (e.g., 12 in FIG. 1A).

QDOT®: A trademark designation for tiny particles or nanocrystals comprised of a semiconducting material, generally having a diameter of about 2-10 nm. A QDOT® emits fluorescence, the color of which is dependent upon the size of the particle. A QDOT® is a specific example of a type of quantum nanocrystal. A "quantum dot" is another non-registered term that is often used synonymously to refer to quantum nanocrystals.

Refractive index: A dimensionless number that describes how light propagates through a medium. The refractive index determines how much light is bent, or refracted when encountering a material or a change in a medium. In some instances, the refractive index describes how light interacts with a material. The refractive index of a material varies according to the composition of the material and the incident wavelength (see FIGS. 6-8). The refractive index of many materials is available in the art, and can be found for example on the internet at websites such as RefractiveIndex.Info. However, these refractive index values are generally less known for nano-scale materials, and are not known across the full range of relevant wavelengths for detection by flow cytometry. In the present disclosure, nanoparticles having a high refractive index are used. A "high" refractive index means that the molecular tag is made of a material that, at an incident wavelength of illumination, can be resolved above the noise of an instrument, for example in a flow cytometer.

Sample: Refers to any biological sample (taken from a biological organism) or environmental sample (taken from an environment). A biological sample is a sample obtained from a subject (such as a human or veterinary subject) that is a biological organism. In particular examples known in the art, the biological sample is a biological fluid sample from any bodily fluid, such as peripheral blood, sera, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen (including prostatic fluid), Cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates or other lavage fluids. A biological sample may also include the blastocyl cavity, umbilical cord blood, or maternal circulation which may be of fetal or maternal origin. The biological sample may also be a tissue sample or biopsy (including a fine needle aspirate) from which vesicles and other circulating biomarkers may be obtained. For example, cells from the sample can be cultured and vesicles isolated from the culture. In various embodiments, biomarkers or more particularly biosignatures disclosed herein can be assessed directly from such biological samples. Biosignatures are the presence or levels of a plurality or multiplicity of biomarkers or functional fragments thereof, utilizing various methods, such as extraction of nucleic acid molecules from blood, plasma, serum or any of the foregoing biological samples, use of protein or antibody arrays to identify polypeptide (or functional fragment) biomarker(s), as well as other array, sequencing, PCR and proteomic techniques known in the art for identification and assessment of nucleic acid and polypeptide molecules. Additional information about biological samples, biomarkers, and the detection of vesicles can be found in U.S. Patent Publication 20140228233 which is incorporated by reference herein.

Scattering: Deviation of a trajectory (for example, of light) from a straight trajectory by one or more paths due to localized non-uniformities in the medium through which is passes. Some types of scattering of electromagnetic radiation (including light) are scattered by a small spherical volume of variant refractive index. Mie theory describes the scattering of an electromagnetic plane wave by a homogeneous sphere. Light scattering is incident wavelength dependent, and has a material-specific intensity profile across a range of wavelengths. Light interacts differently with nanoparticles of different materials and/or with different surface geometries (FIG. 8). Many different devices are known for measuring light scattering intensity, and include flow cytometers and devices such as those shown in U.S. Patent Publication No.20090251696.

Shell: A surrounding layer of a particle, such as a layer of gold or other noble metal that has a sufficiently high index of refraction or light scattering capacity to allow the assembled particle to be detectable above the reference noise of a device, such as a flow cytometer, for detecting light scattering intensity. Alternatively, the surface geometry or topography or the shell can increase scattered light attributes such as diffraction and can modify surface plasmons resonance properties of the material, for example the spiky surface of a nanourchin. Thus, for example, the disclosed nanotags can include a shell (which is not shown in any of FIGS. 1A, 1B, or 1D, but it will be appreciated that the shown nanotags can include such a shell).

SNAP- and CLIP-tag protein labeling systems: Constructs that enable the specific, covalent attachment of a selected molecule to a protein of interest. There are two steps to using the system: cloning and expression of the protein of interest as a SNAP-tag® fusion, and labeling of the fusion with the SNAP-tag substrate of choice. The SNAP-tag is a small protein based on human $O^6$-alkylguanine-DNA-alkyltransferase (hAGT), a DNA repair protein. SNAP-tag substrates are dyes, fluorophores, biotin, or beads conjugated to guanine or chloropyrimidine leaving groups via a benzyl linker. In the labeling reaction, the substituted benzyl group of the substrate is covalently attached to the SNAP-tag. CLIP-tag™ is a modified version of SNAP-tag, engineered to react with benzylcytosine rather than benzylguanine derivatives. When used in conjunction with SNAP-tag, CLIP-tag enables the orthogonal and complementary labeling of two proteins simultaneously in the same cells. Reagents for performing these methods are available from New England BioLabs.

Subject: Living multi-cellular vertebrate organisms, a category that includes human and non-human mammals In particular example, the subject is a human or veterinary subject.

Tumor antigen: An antigen produced in tumor cells that can stimulate tumor-specific immune responses. Exemplary tumor antigens include, but are not limited to, alphafetoprotein (AFP), carcinoembryonic antigen (CEA), cancer antigen 125 (CA-125), MUC-1, epithelial tumor antigen (ETA), TAG-72, immature laminin receptor, HPV E6/E7, BING-4, calcium-activated chloride channel 2, RAGE-1, MAGE-1, MAGE-2, tyrosinase, Cyclin-B1, 9D7, Ep-CAM, EphA3, Her2/Neu, telomerase, mesothelin, SAP-1, survivin, NY-ESO-1, Melan-A/MART-1, glycoprotein (gp) 75, gp100/pme117, beta-catenin, POTE, PRAME, MUM-1, WT-1, PR-1 BAGE family, CAGE family, GAGE family, MAGE family, SAGE family, XAGE family, TRP-1, TRP-2, MC1R, PSA, CDK4, BRCA1/2, CML66, fibronectin, MART-2, p53, Ras, TGF-betaRII and MUC1.

Tumor or cancer: The product of neoplasia is a neoplasm (a tumor or cancer), which is an abnormal growth of tissue that results from excessive cell division. A tumor that does not metastasize is referred to as "benign." A tumor that invades the surrounding tissue and/or can metastasize is referred to as "malignant." Neoplasia is one example of a proliferative disorder. A solid tumor is an abnormal mass of tissue that usually does not contain cysts or liquid areas.

Examples of solid cancers, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (such as adenocarcinoma), lung cancers, gynecological cancers (such as, cancers of the uterus (e.g., endometrial carcinoma), cervix (e.g., cervical carcinoma, pre-tumor cervical dysplasia), ovaries (e.g., ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma), embryonal rhabdomyosarcoma, and fallopian tubes (e.g., carcinoma), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, liver cancer, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma), and skin cancer (such as melanoma and non-melonoma).

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

III. Overview of Several Embodiments

The nanoscale molecular tags disclosed herein overcome the prior barriers to functional sorting of nanoscale particles. The nanoscale molecular tags disclosed herein enable detection of single molecules, for example using microscopy or a device for detecting fluorescence and light scattering intensity, such as a flow cytometer device. The molecular tags allow for sorting of submicron particles in a functional form, based on light scattering properties and/or fluorescent properties. The disclosed molecular nanotags also allow for multiplexing, for example to detect a plurality of different targets, for example by using distinct populations of molecular nanotags, each specific for a particular target.

The disclosed molecular nanotags are unique, as they can be detected and quantified individually. That is, the molecular nanotags can be resolved and quantified in incremental units to directly ascertain the number of targets detected. In contrast, other detection reagents used with flow cytometry are only capable of bulk detection (e.g., when multiple labels are on the surface of, or inside of, one cell). Many flow cytometers, including CytTOF mass spectrometry-based systems, are incapable of detecting summed "signals" from fewer than 1,000 labels. One flow cytometer described as having single label detection capabilities is the ultra-high sensitivity nanoFCM instrument (Anal. Chem., 2009, 81 (7), pp 2555-2563). However, the disclosed molecular nanotags are not limited to being detected individually.

Detection of individual molecular nanotags enables the enumeration (or determination) of the number of nanotags attached per particle (e.g., cell, exosome, extracellular vesicle, etc.). Thus, the disclosed nanotags and methods can be used to detect particles (e.g., cells, exosomes, extracellular vesicles, etc.) having so few epitopes that they would otherwise be undetectable with modern flow cytometric instruments that can only detect epitopes when many epitopes are present (Nolan et al., Platelets. 28:256-62). The molecular nanotags can have one binding site specific to a target particle (e.g., cell exosome, extracellular vesicle, etc.). However, in some examples, more than one molecular nanotag binds to the particle, because the particle may have more than one binding site. If more than two or more different molecular nanotags are used, such that each has a distinct label (e.g., distinct core, such as gold vs silver, has distinct first binding partners, such as one specific for target A, and another specific to target B, or combinations thereof), the two or more different molecular nanotags can bind to the particle of interest and be detected and in some examples quantified, for example using spectral scatter deconvulsion.

Similarly, multiple molecular nanotags, distinguished from each other by different core scattering and/or fluorescence spectra and distinct ligand-binding properties can be used to label distinct types of EVs (e.g., PSMA-positive EVs, arising from prostate or other PSMA-expres sing cells, can be recognized by a gold molecular nanotag that binds to PSMA, and distinguished from and sorted from CD45-positive EVs, arising from cells of hematopoetic origin, can be recognized by a silver molecular nanotag). In some examples, at least two different populations of molecular nanotags are used simultaneously, wherein population 1 is specific for target 1, and population 2 is specific for target 2, and so forth.

In some embodiments, the nanoscale molecular tag includes a core nanoparticle with a diameter of less than about 100 nm; and an armor having a first portion and a second portion, wherein the first portion is bound to the surface of the core nanoparticle, and the second portion is not bound to the core nanoparticle and comprises a functionalized end with a fixed number of binding sites. For example, referring to FIGS. 1A, 1B, and 1D the nanoscale molecular tag 20, 40, 50 includes a core nanoparticle 10 with a diameter of less than about 100 nm; and an armor having a first portion and a second portion, wherein the first portion 12 is bound to the surface of the core nanoparticle, and the second portion 14 is not bound to the core nanoparticle and comprises a functionalized end 16 with a fixed number of binding sites (such as 1, 2, 3 or 5 binding sites).

In some examples, the nanoscale molecular tag further includes a shell surrounding the core. In these embodiments, the first portion of the armor is bound to the shell instead of the core, and the second portion of the armor is not bound to the shell. In some examples, the shell is a layer of gold, silver, both, or other noble metal. In some examples, the shell includes nucleic acid molecules (such as DNA) or PEG.

Any one of, or any combination of, the core, the shell and the armor contribute to fluorescence, light scattering and/or ligand binding properties of the molecular tag that are detectable by a flow cytometer.

In some examples, the diameter of the core nanoparticle is about 20 to about 100 nm, about 30 to about 80 nm, or about 40 to about 60 nm. In specific non-limiting examples, the core nanoparticle is less than about 95 nm, less than about 90 nm, less than about 85 nm, less than about 80 nm, less than about 75 nm, less than about 70 nm, less than about 65 nm, less than about 60 nm, less than about 55 nm or less than about 50 nm. In these examples, the core nanoparticle is at least 20 nm in diameter. In those instances, in which the nanoparticle includes the optional shell, the diameter of the core and shell together is about 20 to about 100 nm, or any of the other dimensions mentioned with respect to the core itself earlier in this paragraph.

In some examples, the fixed number of binding sites is one. In other examples, the fixed number of binding sites is two, three, four or five. In some examples, the armor includes a polymer that has an affinity for the core and/or shell and wraps around the core and/or shell to substantially completely exclude binding of any other molecule or polymer to the nanoparticle. In some instances, the exclusion is a steric exclusion of other polymers, or exclusion of more than one of the selected polymers of which the armor consists.

In some embodiments, the core nanoparticle is comprised of a nanomaterial having a high refractive index that contributes to light scattering properties of the nanoscale molecular tag that are detectable by a device that measures fluorescence and/or light scattering intensity, such as flow cytometer. In some examples, the core nanoparticle comprises a quantum nanocrystal, such as a quantum nanocrystal or quantum dot (e.g. QDOT®). In some examples, the core nanoparticle or its shell comprises a noble metal, such as gold or silver (or both), or materials other than a noble metal, such as $TiO_2$, silica, carbon, CdSe, ZnS or graphite, or any combination thereof.

In some embodiments, the core and optional shell have a parameter $N_{RAQD} = N_{Refractive\ index, Angular\ and\ Quantum\ properties,\ and\ Diameter}$, where $N_{RAD}$ is greater than the limit of detection ($Y_{limit}$) for flow cytometry. The scattering and fluorescent properties of the components of the molecular nanotag or the light scattering and fluorescent properties of the assembled molecular nanotag may demonstrate component-specific quantum effects, such that $N_{RAD}$ may depend on quantum properties of the material, interacting with specific wavelengths of light to produce increased or decreased signals (scatter or fluorescence) that can be detected with multiparametric flow cytometry. Proximity of the molecular nanotag material to material components intrinsic to or otherwise bound to the molecular nanotag-target (an exosome with a targeted epitope, for example, where there is a quantum interaction between the target and the molecular nanotag that modifies the detected scatter or fluorescence intensity of the molecular nanotag). Such quantum-modifying effects would be expected to be dependent on and detectable based on shifts in detection for certain wavelengths, which can be defined spectrally with spectral or other multiparametric cytometric approaches.

In some examples, the core and optional shell used in the molecular nanotag are selective, depending on the detection equipment. For example, if a flow cytometer with 405 nm scattering illumination configuration is used, the use of silver in the core and optional shell of the molecular nanotag provides better scatter-based detection of a small molecular nanotag with core diameter of 10 nm to 40 nm, than does the use of gold in the core and optional shell. However, if a flow cytometer or other device used to detect the nanotag has a 532 nm scattering illumination configuration, molecular nanotags comprised of gold core and optional shell would provide better scatter-based detection than would a silver molecular nanotag. If the detection equipment has both a 405 nm and 532 nm scattering illumination configuration, the core and optional shell used in the molecular nanotag could be gold and silver (e.g., one nanotag containing both gold and silver, or separate nanotags, one with gold, the other with silver) can be used simultaneously.

In some embodiments, the armor comprises a polymer. In some examples, the polymer contributes to the fluorescence, light scattering and/or ligand binding properties of the molecular tag. In some examples, the polymer comprises a nucleic acid, such as deoxyribonucleic acid (DNA), for example single-stranded DNA, RNA, or PNA. In specific non-limiting examples, the DNA is single-stranded phosphorothioate DNA (ptDNA).

In particular examples in which the armor comprises single-stranded DNA, the first portion of the armor is about 30 to about 100 nucleotides in length, such as about 40 to about 90, about 50 to about 80, or about 60 to about 70 nucleotides in length. In some examples, the first portion of the armor is comprised of all phosphorothioate adenosine nucleotides.

In particular examples in which the armor comprises single-stranded DNA, the second portion of the armor is about 10 to about 30 nucleotides in length, such as about 15 to about 25, about 18 to about 22, or about 20 nucleotides in length.

In other examples in which the armor includes a polymer, the polymer comprises polyethylene, such as polyethylene glycol (PEG) or a derivative thereof.

In some embodiments, the functionalized end of the armor comprises a first binding partner that is capable of specifically binding to a second binding partner, such as a target (e.g., protein, such as a ligand). In specific non-limiting examples, the first and second binding partners are respectively selected from benzylguanine and a SNAP-Tag; benzylguanine and a CLIP-Tag; biotin and streptavidin; a single-stranded oligonucleotide and a complementary single-stranded oligonucleotide; a single-stranded oligonucleotide and an aptamer; DCFPyL and prostate specific membrane antigen (PMSA); a receptor and a ligand; a ligand and a receptor; an antigen and an antibody (such as an antibody associated with a disease or infection, such as a bacterial or viral infection); or an antibody and an antigen, such as a tumor antigen or peptide tag (such as a His tag or a FLAG tag). In some instances, the tumor antigen comprises PMSA, epidermal growth factor receptor (EGFR), vascular endothelial growth factor (VEGF), HER1, Her-2/neu, epithelial cell adhesion molecule (EpCAM), CD20, CD24, CD25, CD33, CD52, CA125, Lewis Y, TAG72, CD133, CD47, CD147, PD-L1, GPC-1, CEA, alpha-fetoprotein (AFP), or Muc-1. Thus, in some examples, the nanoscale molecular tag includes as the first binding partner a binding agent (such as an antibody, ligand, or aptamer) specific for PMSA, EGFR, VEGF, HER1, Her-2/neu, EpCAM, CD20, CD24, CD25, CD33, CD52, CA125, Lewis Y, TAG72, CD133, CD47, CD147, PD-L1, GPC-1, CEA, AFP, or Muc-1. In one example, the tumor antigen is PMSA, and the nanoscale molecular tag includes an anti-PSMA antibody, or PSMA ligand such as DCFBC (see FIGS. 10A-10C and 11E).

In some examples, the nanoscale molecular tag includes a binding agent (such as a receptor) specific for a target ligand, such as a ligand on an extracellular vesicle, such as a TIM-4 receptor to detect phosphatidyl-serine (PS). For example, such a nanoscale molecular tag can be used to monitor cell death (such as general cell death, apoptosis, chemical-induced cell death (e.g., due to chemotherapy) or radiation-induced cell death). Although high levels of PS are expected after irradiation, all EVs include low or moderate PS in the phospholipid surface. TIM-4 is a receptor that reversibly binds to PS in a calcium dependent manner, which allows for label elution after binding. Other vesicle-associated markers that can be targeted to bind to a disclosed nanoscale molecular tag include (e.g., the nanotag can include a binding reagent specific for) CA-125, CA 19-9, C-reactive protein (CRP), CD95, FAP-1, EGFR, EGFRvIII, EpCAM, apolipoprotein AI, apolipoprotein CIII, myoglobin, tenascin C, MSH6, claudin-3, claudin-4, caveolin-1, coagulation factor III, CD9, CD36, CD3'7, CD53, CD63, CD81, CD136, CD14'7, Hsp70, Hsp90, Rab13, Desmocollin-1, EMP-2, CK7, CK20, GCDF15, CD82, Rab-5b, Annexin V, MFG-E8, FILA-DR, miR200 microRNAs In some embodiments, the nanoscale molecular tag comprises a fluorophore, such as one or more of the fluorophores listed herein.

In some embodiments, the nanoscale molecular tag includes a core nanoparticle with a diameter of less than 100 nm; an optional shell; an armor, such as a single-stranded nucleic acid molecule having a first portion and a second portion, wherein the first portion comprises phosphorothioate DNA that is bound to the surface of the core nanoparticle, which reduces nanoparticle valency to a fixed number of functional binding sites (for example, one, two, three, four or five functional binding sites); a linker to connect armor binding site(s) to a functional ligand for a designated target; and a functional ligand (comprised of protein, nucleotide, or other ligand-binding element) for a designated target, and wherein any one of, or any combination of, the core, the shell and the armor contribute to fluorescence, light scattering and/or ligand binding properties of the molecular tag that are detectable by an instrument for detecting them.

In other examples, the core is a quantum nanocrystal having a fluorescent core surrounded by a shell that modulates the fluorescence and can also modify the binding surface. In yet other examples, the armor can further modify fluorescence and/or binding properties of the molecular tag.

Also provided herein are methods for detecting in a flow cytometer a single target molecule in a sample. In some embodiments, the method includes contacting the sample with a nanoscale molecular tag disclosed herein, wherein the functionalized end of the nanoscale molecular tag specifically binds the target molecule if present in the sample; and analyzing the sample using a flow cytometry instrument configured for resolution of small particles to detect individual nanoscale molecular tags bound to the target molecule by detection of side scatter or detection of fluorescence, or both.

In some embodiments, the sample is analyzed in a flow cytometer using at least two side scatter channels. In some examples, a first side scatter channel is used as a trigger and a second side scatter channel is used as a detector. In some examples, the method includes detecting parallel subthreshold events. In some examples, at least two side scatter channels are used as detectors, such as two or more of 405 nm, 445 nm, 488 nm, 532 nm, 561 nm, 592 nm, and 640 nm. In some examples, at least two side scatter channels are used as detectors, such as two or more of 405 nm, 488 nm, 561 nm, and 640 nm. In some examples, at least two side scatter channels are used as detectors, such as at least 405 nm and 561 nm, or at least 488 nm and 561 nm. In some embodiments, the sample is a biological sample, such as a biological membrane, for example a sample comprising extracellular vesicles (EVs). In other examples, the biological sample comprises a virus. In other embodiments, the sample is an environmental sample, such as a water, soil, or air sample.

In some examples of the method, the target molecule includes a tumor antigen. In specific non-limiting examples, the tumor antigen includes PMSA, vascular endothelial growth factor (VEGF), HER1, Her-2/neu, epithelial cell adhesion molecule (EpCAM), CD20, CD24, CD25, CD33, CD52, CA125, Lewis Y, TAG72, CD133, CD47, CD147, PD-L1, GPC-1, CEA, alpha-fetoprotein (AFP), or Muc-1. However, any of the markers disclosed herein or in the incorporated references can be used in the methods disclosed in the present specification.

IV. Flow Cytometry

Flow cytometry is a laser-based, biophysical technology employed in cell counting, cell sorting, biomarker detection and protein engineering, by suspending cells in a stream of fluid and passing them by an electronic detection apparatus. It allows simultaneous multiparametric analysis of the physical and chemical characteristics of up to thousands of particles per second. Flow cytometry is routinely used in the diagnosis of health disorders, especially blood cancers, but has many other applications in basic research, clinical practice and clinical trials. A common variation is to physically sort particles based on their properties, so as to purify populations of interest.

Flow cytometry instruments are able to analyze several thousand particles every second, in "real time," and can actively separate and isolate particles having specified properties. A flow cytometer is similar to a microscope, except that, instead of producing an image of the cell, flow cytometry offers "high-throughput" (for a large number of cells) automated quantification of set parameters. To analyze solid tissues, a single-cell suspension is first prepared.

Basic flow cytometers have five main components:

(1) A flow cell; a liquid stream (sheath fluid) that carries and aligns objects from the sample (cells, EVs, or other detectable objects) so that they pass single file through the light beam for sensing;

(2) A measuring system; commonly used are measurements of impedance (or conductivity) and optical systems such as lamps (mercury, xenon); high-power water-cooled lasers (argon, krypton, dye laser); low-power air-cooled lasers (argon (488 nm), red-HeNe (633 nm), green-HeNe, HeCd (UV)); diode lasers (blue, green, red, violet) resulting in light signals;

(3) A detector and Analogue-to-Digital Conversion (ADC) system, which generates forward-scattered light (FSC) and side-scattered light (SSC) as well as fluorescence signals from light into electrical signals that can be processed by a computer;

(4) An amplification system (linear or logarithmic); and (5) A computer for analysis of the signals.

The process of collecting data from samples using the flow cytometer is termed "acquisition." Acquisition is mediated by a computer physically connected to the flow cytometer, and the software which handles the digital interface with the cytometer. The software is capable of adjusting parameters (such as voltage and compensation) for the sample being tested, and also assists in displaying initial sample information while acquiring sample data to ensure that parameters are set correctly.

Currently available instruments generally have multiple lasers and fluorescence detectors. Increasing the number of lasers and detectors allows for multiple antibody labeling, and can more. precisely identify a target population by their phenotypic markers. Some instruments are capable of taking digital images of individual cells, allowing for the analysis of fluorescent signal location within or on the surface of cells.

Additional information about flow cytometry as it applies to nanomaterial analysis can be found in U.S. Patent Publication No. 21300095575, which is incorporated herein by reference.

The following examples are provided to illustrate certain particular features and/or embodiments. These examples should not be construed to limit the disclosure to the particular features or embodiments described.

EXAMPLES

Example 1

Molecular Nanotags

This example describes molecular nanotags that enable detection of single molecules, such as molecules on the surface of EVs or viruses, using microscopy or an instrument that measures fluorescence and/or light scatter intensity, such as a flow cytometer, for example using the NanoFACS method described in the incorporated U.S. Patent Publication No. 20130095575 and Morales-Kastresana et al., *Scientific Reports*, 7:1878, 2017.

Molecular nanotags are composed of modular elements that confer target specificity, fluorescence, and light scattering attributes to the composite molecular nanotags, so that individual molecular nanotags (and individual molecular nanotag targets) can be detected by both fluorescence and light scatter on high resolution flow cytometers, such as the AstriosEQ. Molecular nanotags can be used as diagnostic and prognostic reagents for the identification of disease-associated biomarkers, such as tumor-associated proteins carried by tumor-derived extracellular vesicles.

In particular examples, a molecular nanotag comprises an "armored" core nanoparticle, which is monovalent and attaches individually via a Lock:Key (or "Target:Bait") mechanism to a target ligand, such as on the surface of an extracellular vesicle. As long as one component contributes an elastic or inelastic scattering property that can be detected with single label resolution, then adding additional components with complimentary attributes (e.g., adding fluorescent labels to a gold or silver particle that can be detected individually, without the addition of a fluorophore), allow for mutidimentsional Molecular NanoTag design and multiplex applications, but only one resolvable component is required for the use of the molecular nanotag to detect one epitope/ligand.

Molecular nanotags include a nanoscale light scattering element (such as the core nanoparticle 10, a fluorophore (e.g., the nanocrystal if the core nanoparticle is a QDOT®)), and a monovalent linker 14 for target detection (FIGS. 1A-1B). The molecular nanotags is designed to provide a method for detection of a single molecule on the surface of a single nano-sized vesicle. The inventors have demonstrated that 29 nm PEGylated QDOTS® can be observed at and above the scattered light noise floor, in addition to being fully resolved as individual (single molecule) particles by fluorescence, for example, when using the nanoFACS method on the AstriosEQ.

The previously disclosed monovalent quantum nanocrystals of the incorporated Farlow et al. publication are shown in FIG. 1C. As described in that reference, steric exclusion using 70-90 mer DNA sequences, such as ttDNA and ptDNA. The DNA sequences efficiently generated monovalent nanoparticles of distinct sizes, shapes, and hence spectral properties. Dynamic light scattering analysis reveals that ptDNA-wrapped monovalent nanocrystals are 12 nm in diameter, similar in size to an IgG (dotted line) and about half the size of conventional streptavidin quantum nanocrystals (22 nm). DNA-wrapped quantum nanocrystals can be selectively targeted by 3'-modification of the oligonucleotide. Complementary strands bearing a 5' targeting modification such as benzylguanine (BG), benzylcytosine (BC) or lipid allow modular targeting of mQDs to streptavidin, SNAP-, CLIP-tags, or cell surfaces. These targeting techniques can also be used in association with the molecular nanotags of the present disclosure.

The use of this targeting approach with the present molecular nanotags is illustrated in FIG. 1D in which an armored nanoparticle 40, 50 (such as a quantum nanocrystal having a diameter of 1-30) is armored with a nucleic acid polymer (or another molecule, such as PEG) 12 with an affinity for the quantum nanocrystal semiconductor surface, and that sterically excludes other molecules (including polymers) from the surface of the nanoparticle. A linker 14 can link the armor (e.g., nucleic acid polymer, polyethylene glycol (PEG) or a PEG derivative) to another armored nanoparticle (bottom of FIG. 1D), or to a label 16 that specifically binds a target ligand (top of FIG. 1D), such as a target ligand on an extracellular vesicle (EV).

FIG. 4 illustrates that molecular nanotags are a new class of labels that contain modular components, including a nanoscale light scattering element (the core nanoparticle in one depicted example), a fluorophore (which can also be the component that contributes scattering intensity if the core nanoparticle is a quantum nanocrystal or similar component) and a monovalent linker for target detection. In an example shown in FIG. 4, a quantum nanocrystal is PEGylated with a polyethylene glycol (PEG) polymer steric exclusion armor that increases the size of the assembled nanotag, for example by 5-25 nm. In particular examples, the armored quantum nanocrystal has a diameter of less than 50 nm, for example no more than 20-40 nm, for example no more than 30 nm. In the example illustrated in FIG. 4, a 29-nm PEGylated quantum nanocrystal can be observed at and above the scattered light noise floor, in addition to being fully resolvable as individual (single molecule) particles by fluorescence when using a nanoFACS high resolution flow cytometry method on an AstriorEQ sorter that is available from Beckman Coulter Life Sciences. PBS alone was used to demonstrate the instrument noise. The Qtracker® 655 quantum nanocrystal used in this example was obtained from Molecular Probes, and the specifications of the quantum nanocrystal, which are shown in FIG. 4, were an absorbance of 2.1 µM, a fluorescence emission maximum at 656 nm, with a quantum yield of 74%.

Example 2

Small Molecule PSMA Targeting Ligands

The molecular nanotags disclosed herein are a class of labels with a broad number of potential applications. As one example, they can be used for the identification of labels for tumor-associated extracellular vesicle (EV) components. Prostate cancer is one example of a type of tumor that produces EVs that carry relevant tumor biomarkers that are highly correlated with prognosis and treatment response patterns. Prostate cancer is a common malignancy that is diagnosed in 1 of 7 men in the United States. Prognosis depends on the stage (extent of dissemination) of the tumor at diagnosis, grade (or aggressiveness of the tumor cells), and sensitivity of the tumor to available treatments, such as androgen deprivation. Surface expression of prostate specific membrane antigen (PSMA) on prostate tumor cells is associated with loss of responsiveness to androgen deprivation therapy, and there are ongoing trials investigating the use of PSMA ligands (such as DCFPyL) in molecular imaging studies for the purpose of diagnostic evaluation, improving up-front selection of patient-specific treatment choices, and providing adaptive treatment guidance. These imaging modalities can resolve only collections of tumor cells that exceed at least 0.5 cm. Because PSMA-expressing tumor cells secrete PSMA-expressing EVs, and many tumor cells produce many orders of magnitude of EVs per single tumor cell, typically in concentrations in excess of healthy tissues, tumor-associated EVs are being investigated as tumor biomarkers, identifiable in samples of plasma, urine, and other biological fluids. The present disclosure contemplates, for example, the use of a high resolution flow cytometer and molecular nanotas specific for PMSA for the analysis and quantification of PSMA-bearing EVs noninvasively. FIG. 5 demonstrates that single EVs expressing PSMA can be detected by nanoFACS (for details on method see Morales-Kastresana et al., *Scientific Reports,* 7:1878, 2017).

Figure 10A:
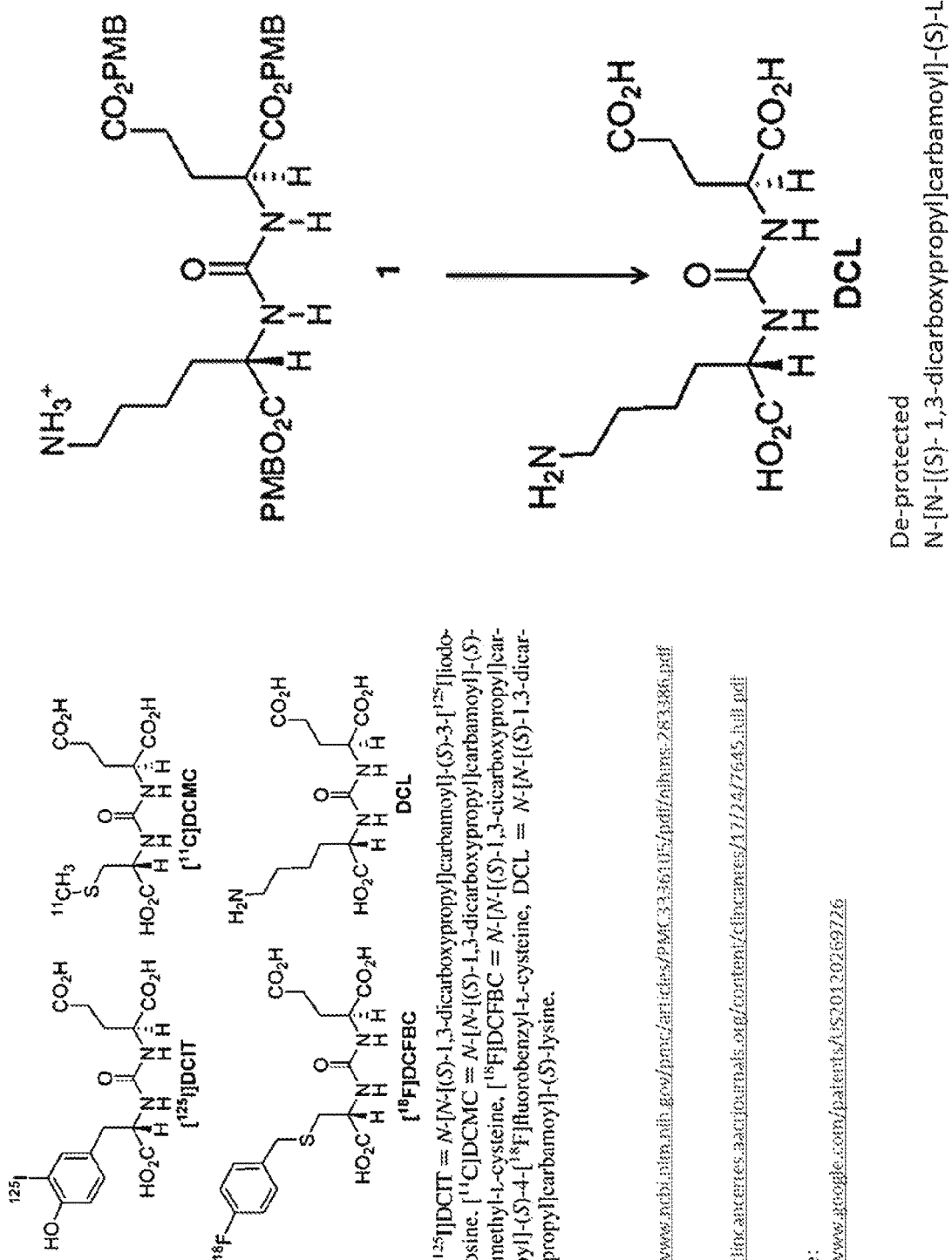

FIGS. 10A-10C illustrate examples of small molecule PSMA ligands that can be used as labels on the molecular nanotags of the present disclosure to target prostate specific ligands on targets, such as EVs. For example, the PSMA ligand can be attached to the armored quantum nanocrystal, for example by linkage to the free end of the armoring polymer, such as a nucleic acid or PEG polymer that sterically excludes other linkages and provides the capacity for monovalent labeling of the molecular nanotag. Thus, referring to FIG. 1B, molecular nanoprobe used to detect EVs expressing PSMA can include a PSMA ligand (such as those in FIGS. 10A-10C) attached to the armored quantum nanocrystal 20 by linkage to the free end 14 of the armoring polymer 12, such as a nucleic acid or PEG polymer (see, for example, FIGS. 11A-11F).

Example 3

Attachment of Targeting Ligands to the Molecular Nanotag

FIGS. 11A-11F further illustrates the concept of labeling the molecular nanotags and contrasts it to the prior design of Farlow et al. (*Nat. Methods* 10(12): 1203-1205, 2013) which disclosed a quantum nanocrystal with an armor of phosphorothioate DNA (ptDNA) that sterically excluded the quantum nanocrystal surface from additional reactions. The ptDNA has an affinity for semiconductor surfaces, such as the surface of the quantum nanocrystal. As described by Farlow et al., after transfer of commercial CdSe:ZnS QDs from the organic to the aqueous phase, the quantum nanocrystals are treated with ptDNA of various sequences and lengths. DNA-functionalization produces quantum nanocrystals with an ionic character that are easily distinguishable from unfunctionalized QDs by agarose gel electrophoresis. The 605 nm emitting quantum nanocrystals are titrated with increasing concentrations of an oligonucleotide comprising a 50 adenosine ptDNA domain ($A^S_{50}$) and a 20 nucleotide ssDNA targeting tail (to produce an oligonucleotide that is about 70 nucleotides in length). At stoichiometric or higher ratios of ptDNA and quantum nanocrystals, no sign of unfunctionalized or multiply functionalized products are observed, consistent with the quantitative formation of a monovalent product. Farlow et al. also demonstrated that these monovalent quantum nanocrystals are modularly and efficiently targeted to protein or lipid tags used frequently for live cell imaging. The targeting functionality is introduced by 3'-modification of the ptDNA or by hybridization of the monovalent quantum nanocrystals with complementary DNA bearing a 5'-modifcation. These strategies can be used to conjugate them with biotin, benzylguanine (BG), benzylcytosine (BC), and lipids, thereby targeting them to streptavidin, SNAP, CLIP, and cell membranes, respectively.

The molecular nanotags of the present disclosure have been modified from the Farlow et al. disclosure. In one example illustrated in FIG. 11B, a free end of the monovalent polymer is biotinylated and linked to a streptavidin (SA)/biotin, anti-PSMA antibody. In another example, the free end of the monovalent polymer is biotinylated and linked to a streptavidin (SA)/biotin, anti-PSMA aptamer (FIG. 11C). In another example, the free end of the monovalent polymer is biotinylated and linked to a SA/biotin small molecule PSMA ligand. (FIG. 11D) Alternatively, the free end of the monovalent polymer is azidated and linked to a Click partner such as DCBO-TEG-ACUPA/DCL (or other small molecule PSMA ligand) (FIG. 11E). The new molecular nanotags are particularly adapted for targeting, sorting and counting EVs and other nanoparticle targets of biological significance.

In another illustrated embodiment in FIG. 11F, the molecular nanotag includes a core of a CdSe quantum nanocrystal, armored with a PEG coating that sterically excludes attachment of other molecules to the surface of the nanotag core. Streptavidin (SA) is bound to the PEG coating, and the SA binding partner biotin conjugates anti-PSMA specific monoclonal antibodies to the biotin. For example, streptavidin Qdots can be used to detect biotinylated antibodies bound to EVs containing the ligand of the antibody. Size exclusion chromatography can be used to separate EVs with bound/attached molecular nanotag labels from unbound molecular nanotags. In yet other embodiments, the biotin conjugates an anti-PSMA aptamer such as A9g, or an anti-PSMA ligand such as DCL (although not specifically illustrated in the CdSe Core-PEG-SA-Biotin-mAb embodiment). Commercially available streptavidin Qdots were used to detect biotinylated antibodies bound to EVs with the ligand of the antibody. Size exclusion chromatography was used to separate EVs with labels from unbound labels.

Example 4

Anti-PSMA Aptamers and Ligands

PSMA aptamers can be designed, using some of the reagents of Dassie et al., *Mol. Ther.* 22(11): 1910-1922 (2014), 10.1038/mt.2014.117, which is incorporated by reference. Briefly, in vitro assays were performed using in vitro transcribed RNA. All in vivo assays were performed using chemically synthesized RNA (Integrated DNA Technologies, Coralville, Iowa or TriLink Biotechnologies, San Diego, Calif.) modified with 2'-fluoro pyrimidines, 2'-hydroxyl purines and a Cl2-NH$_2$ 5' terminal modification.

Figure 12B:
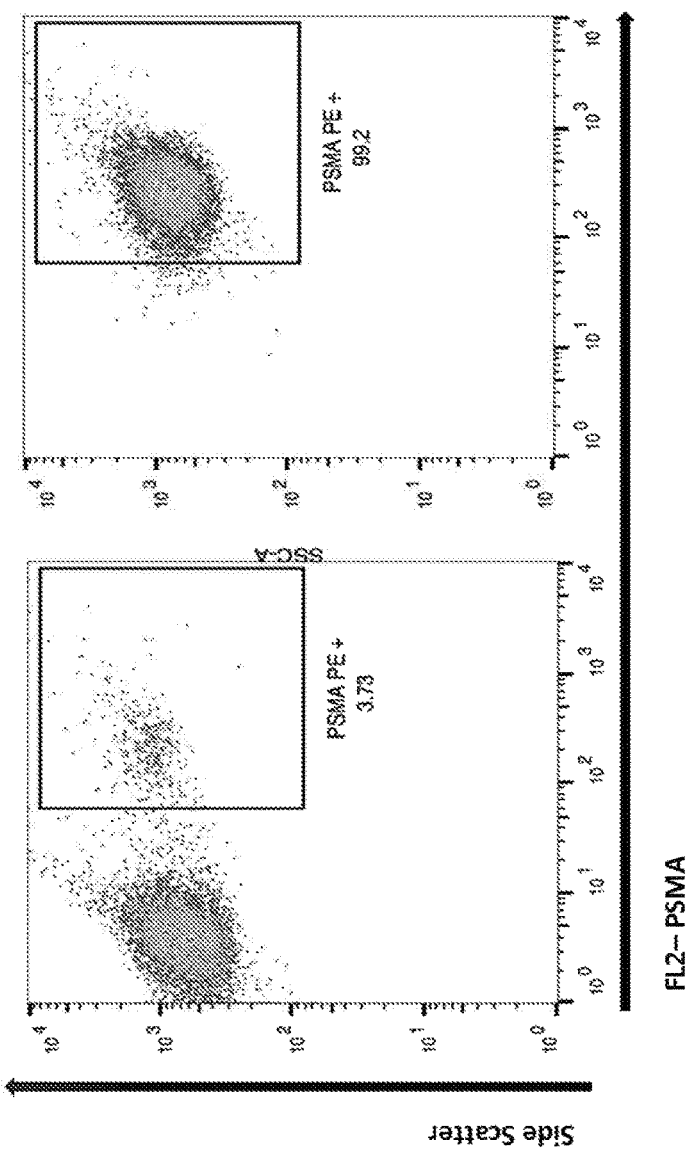
Figure 12A:
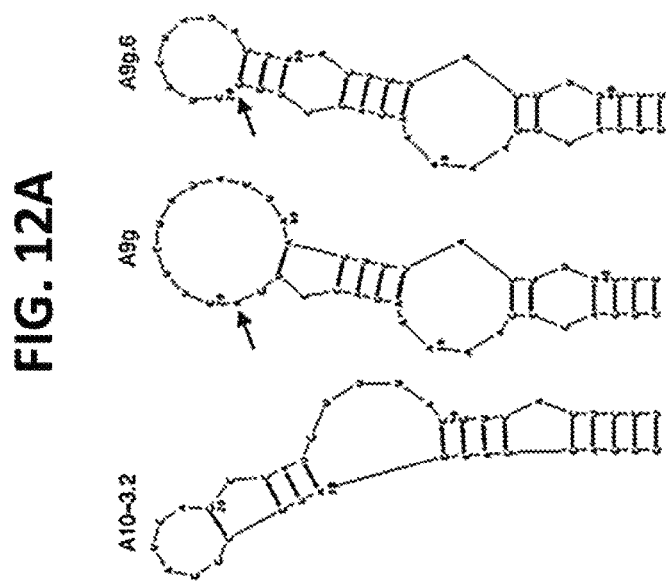
Figure 14D:
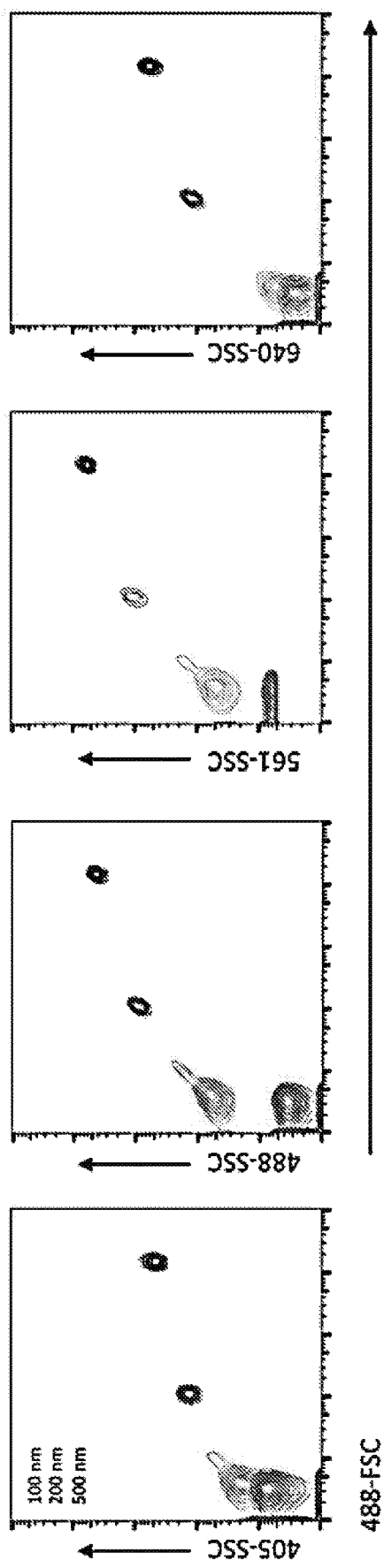
Figure 16A:
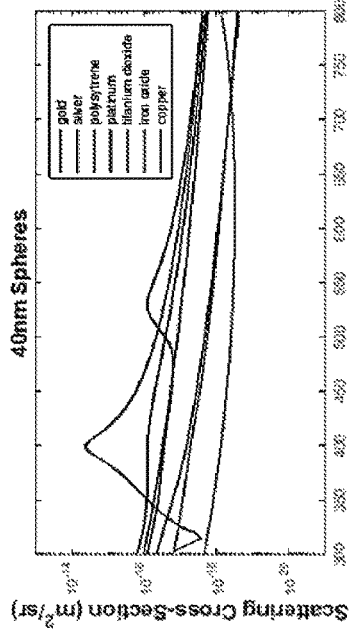
Figure 16B:
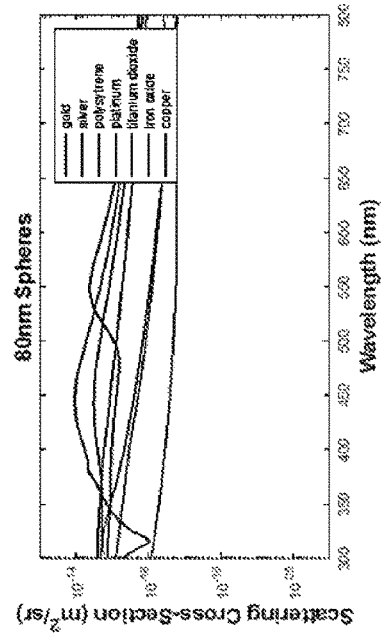
Figure 16C:
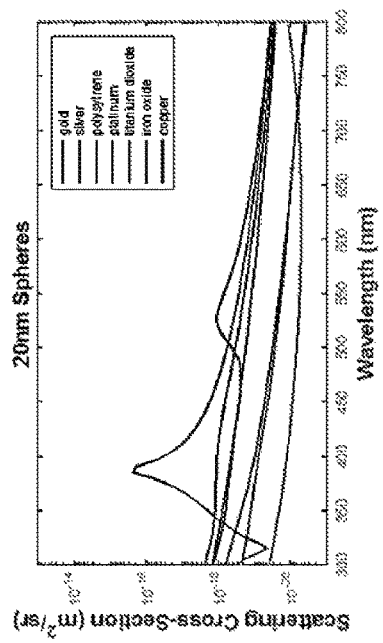
Figure 16D:
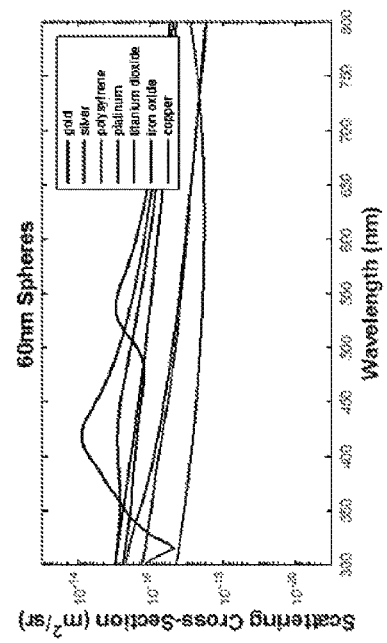
Figure 16E:
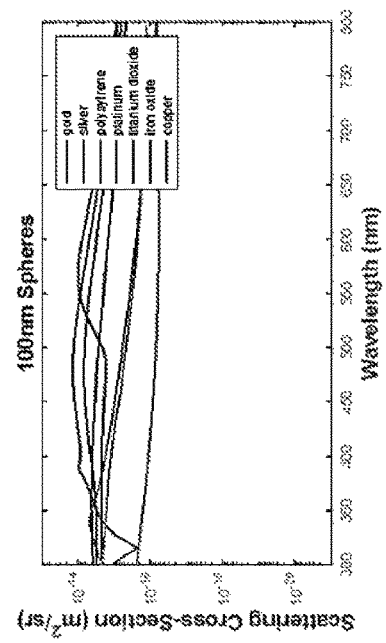

RNA aptamers were transcribed as previously described in Dassie et al. The structure of the three aptamers is shown in FIG. 12A. As shown in FIG. 12B, the resulting A10-3.2 aptamer binds PSMA but does not inhibit cell growth, the A9g aptamer binds PSMA and inhibits cell growth, and the A9g.6 aptamer did not bind PSMA and did not inhibit cell growth. A9g and A10.3 aptamers could therefore be used as a RNA aptamer to PSMA in association with the molecular nanotags of the present disclosure. Thus, referring to FIG. 1B, molecular nanoprobe used to detect PSMA (such as PSMBA on an EV) can include a PSMA aptamer (such as A9g or A10.3) attached to the armored quantum nanocrystal 20 by linkage to the free end 14 of the armoring polymer 12, such as a nucleic acid or PEG polymer.

In one example, an azidated monovalent polymer on the surface of the nanoparticle, which is conjugated by click chemistry to a PSMA ligand, such as DCBO-TEG (see FIG. 11E). Other PSMA ligands that could be conjugated to the nanoparticle include PSMA ligands from Futurechem Co., Ltd, such as DKFZ-PSMA-11 (Glu-CO-Lys(Ahx)-HBED-CC, Glu-NH-CO-NH-Lys(Ahx)-HBED-CC); tert-butyl-DCL-hexyl-NHS ester ((S)-di-tert-butyl 2-(3-((S)-1-(tert-butoxy)-6-(8-((2,5-dioxopyrrolidin-1-yl)oxy)-8-oxooctanamido)-1-oxohexan-2-yl)ureido)pentanedioate); DCL (N-[N-[(S)-1,3-dicarboxypropyl]carbamoyl]-(S)-L-lysine,2-[3-[5-amino-1-carboxypentyl]-ureido]-pentanedioic acid); and tert-butyl-DCL (2-{3-[1-tert-butyl-carboxylate-(5-aminopentyl)]-ureido}-di-tert-butyl pentanedioate). Thus, referring to FIG. 1B, molecular nanoprobe used to detect PSMA (such as PSMBA on an EV) can include a PSMA ligand (such as those listed above) attached to the armored quantum nanocrystal 20 by linkage to the free end having an azide 14 of the armoring polymer 12, such as a nucleic acid or PEG polymer.

Example 5

Detection of Single Exosome-Sized Particles and Individual Molecules

The disclosed nanoscale molecular tags can be used, for example, to detect and determine the number of specific molecules associated with biologically relevant subsets of extracellular vesicles, such as exosomes.

Figure 2:
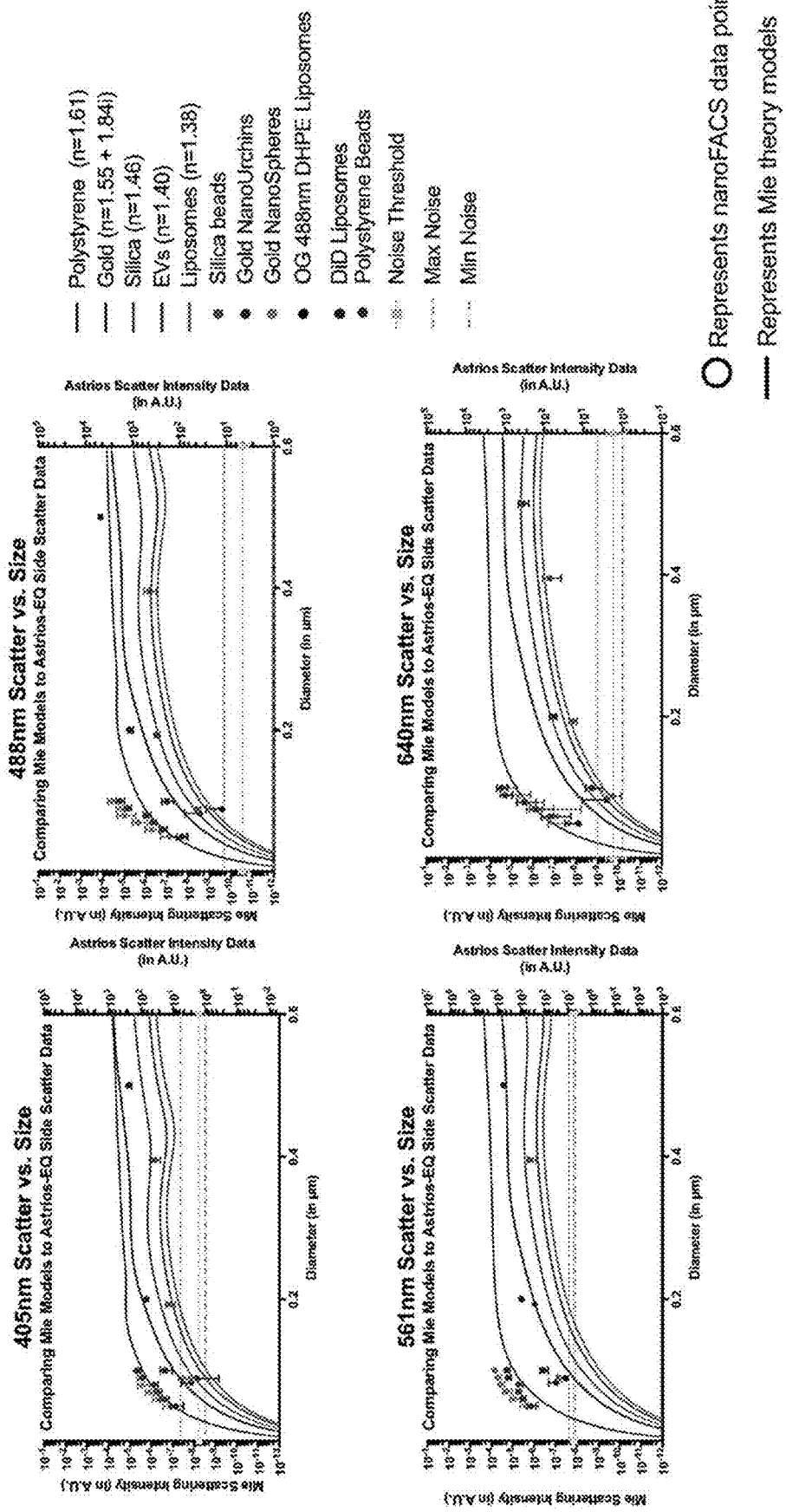
Figure 3:
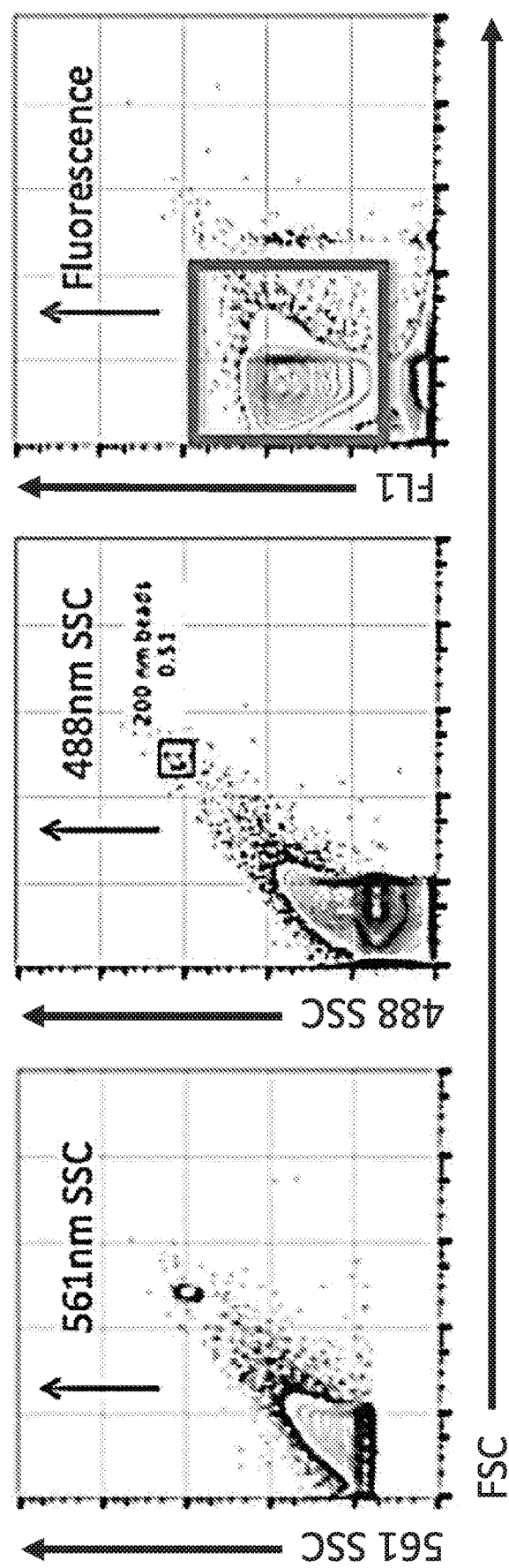

In some instances, tumor-specific and/or immune-specific biomarkers in exosome subsets are identified. The methods disclosed herein permit the identification of specific biomarkers on or in a single exosome (or other nanoparticle). Single quantum nanocrystal (e.g. QDOT®) detection has been demonstrated (FIG. 3). Monovalent quantum nanocrystals enable single molecule detection, counting and tracking, and can be made for any desired biomarker.

Exemplary quantum nanocrystals are commercially available, such as from Life Technologies (Carlsbad, Calif.). For example, a QDOT® (or other quantum nanocrystal) is maximally excited in the UV wavelengths and has fluorescence emission maximums of 525 nm, 545 nm, 565 nm, 585 nm, 605 nm, 625 nm, 655 nm, 705 nm, or 800 nm depending on the particle. Functionalized quantum nanocrystals may have an overall size, in a spherical approximation, of about 10-30 nm, for example about 20 nm. The quantum nanocrystal can, for example, have a core/shell composition of cadmium selenide (CdSe)/zinc sulfide (ZnS), or cadmium seleno-telluride (CdSeTe)/ZnS. The shell can modify the fluorescence properties of the core.

Example 6

Methods of Using Nanotags in Flow Cytometry

The disclosed molecular nanotags can be used in a flow cytometer that is configured to detect submicron particles, such as nanoparticles, in biological samples. Such methods are disclosed, for example, in U.S. Patent Publication 20130095575 which is incorporated herein by reference. See particularly examples 1 and 2 of that patent publication which disclose a NanoFACS method. See also Danielson et al., *PLoS One* 2016, 11(1): e0144678, incorporated herein by reference.

NanoFACS has a variety of features that make it useful in combination with the molecular nanotags.

(1) Although fluorescence parameters are integral to the use of nanoFACS, nanoFACS does not require the use of a fluorescent trigger. The use of a high resolution scatter parameter allows a more complete representation of the population to be seen, analyzed, and managed with respect to choices of sort parameters and gates.

(2) NanoFACS does not require the aggregation of several EVs to a single bead, as is used in other flow cytometry approaches for studying EVs and other nanoparticles. When nanoFACS is performed with appropriate sample dilutions and instrument configurations, particles are visualized as truly single particles. The rate of particle singlets (>99%) is also superior to the rates of singles observed with published bead-bound assays for single particle analysis, with which 90% of the particles represent singlets. By detecting the particles alone, without binding them to beads, the nano- FACS method better preserves particle scatter attributes, biological function, and the ability to phenotype subsets.

(3) NanoFACS provides a high-speed method that can be used for preparative sorting for a wide range of biological or inorganic nanoparticles, with preservation of functional activity. As compared to nanoscale viral sorting with a (slow) flow-cell based platform, the use of the nanoFACS approach with high speed jet-in-air systems described herein allows preparation 100-1000× more particles per hour, at rates that are required for preparative sorting of EVs and viral studies for functional assays.

(4) The nanoFACS method uses flow cytometers at the limits of their intended detection range. As such, the threshold is set at a level that allows a well delineated population of reference noise at and just above the threshold, due to the detection of laser light scattered off of the fluid stream, and there may be relevant particles of interest that are excluded by the threshold that is set. The use of a parallel subthreshold population to provide a partial representation of the particles that are detected in association with the stray light reflections that produce reference noise at that threshold, can provide helpful information as to the nature of what is being "missed" in terms of detection. When sorting, this information informs the operator as to what types of subthreshold events would be collected along with the selected sort populations, and determine whether alternate staining or separation strategies should be tested.

With the nanoFACS approach, it is possible to analyze and sort nanoscale EV and other subpopulations, with good fidelity, and in preparative quantities sufficient for selected functional studies. The methods disclosed herein allow for the use of flow instruments to separate biological submicron particles, for example to sort EVs in the 40-200 nm range and sort HIV and other small particles in the 100 nm range, as single particles in preparative quantities, with preservation of biological activity. The molecular tags are effective and useful for labeling individuals particles for sorting and counting them.

Example 7

Modifications to Diminish Undercounting

Semiconductor nanocrystals (sometimes referred to as quantum dots) are excellent light emitters for applications as fluorescent molecular probes. Their optically excited emission is efficient (quantum efficiencies can approach unity), narrow-band, and tunable, i.e., light-output colors are precisely tunable from the ultraviolet through the visible and into the infrared depending on quantum nanocrystal composition and size. Absorption is quasi-broadband, facilitating excitation and allowing for the possibility of using a single excitation source to excite multiple quantum nanocrystals for a range of emission colors that permit "optical barcoding." However, optical properties of the quantum nanocrystal are sensitive to surface thickness and they can be in the "off" state which can result in them being "undercounted" when they are being used for molecular counting (such as in flow cytometry) (FIGS. 13A-13E). The present method overcomes that drawback by increasing the shell of the quantum nanocrystal from its conventional thickness of about 6 nm up to a thickness of at least 10 nm, for example a thickness of 10-20 nm ("giant" quantum nanocrystals).

Methods for making "giant" quantum nanocrystals are disclosed for example, in Vela et al., *J. Biophotonics* 3(10-11): 706-717 (2010), and Hollingsworth et al., *Proc. SPIE* 7189:718904 (Mar. 3, 2009). The disclosed methods of making these "giant" quantum nanocrystals is incorporated by reference herein. Briefly, growth of a very thick, defect-free inorganic shell with an ability to suppress blinking was achieved starting with 3-4 nm CdSe quantum nanocrystal cores. Particles are grown to a size of ~10-20 nm by sequentially applying monolayers of inorganic shells. The shell monolayers—typically CdS, but alternatively $Cd_xZn_yS$ alloys followed by ZnS, are grown onto CdSe cores using modified procedures based on a successive ion layer absorption and reaction (SILAR) method. Effectively, the wave function of the quantum nanocrystal core is separated from its surface, creating a colloidal giant quantum nanocrystal. The giant quantum nanocrystals have been found not to photobleach over long observation times and are characterized by significantly suppressed blinking.

Example 8

Methods for Profiling Microvesicles

Methods of profiling microvesicles, including exosomes, are disclosed in publications such as US Patent Publication 20130095575 as well as 20140228233 and 20140162888 that are incorporated by reference. In some examples, profiling includes flow cytometry profiling of microvesicles such as EVs, and the use of the profiling in a variety of clinical and research applications. Antigen presenting cells and tumor cells, among others, produce large quantities of submicron particles, i.e., exosomes arid microparticles, which modulate tumor immune responses and the tumor microenvironment. The use of flow cytometers at the limits of their resolution permits the analysis, sorting and studying of submicron particles in functional form, without using electron microscopy or aggregation to beads, which change the biological properties of the particles. in the already disclosed nanoFACS method, the cytometer is configured for maximal resolution of small particles. Non-specific background noise can be reduced by adding both a filter and a small particle detector, as well as tuning the nozzle height to eliminate drop drive noise. Use of the molecular nanoprobes disclosed herein greatly enhances the profiling ability of the methods.

The microvesicles are obtained from any convenient biological sample. Serum samples from an individual are an exemplary sample, which may be treated in various ways, including binding to affinity reagents for identification and sorting. For example, samples may be stained with antibodies that selectively bind to markers of immune cells, tumor markers, markers of radiation exposure, and the like. The microvesicles may also be sorted and analyzed for the presence of nucleic acids of interest, such as RNA, including microRNAs. The quantity and/or quality (for example the presence of protein or nucleic acid markers or other markers of interest) of microvesicles may be used for monitoring of tumor responses to cytotoxic therapies (for example in chemotherapy and radiation therapy), immune responses to tumor vaccines, monitoring immune cells following transplantation, including the development of graft v host disease, biodosimetry (for assessing the level of radiation exposure as from a nuclear accident, dirty bomb, etc.). Such analysis may include detecting the number of microvesicles relative to total serum protein levels, and may include determining the presence of annexin V on the microvesicles. In another embodiment, the method further comprises assessing a clinical factor in a mammalian subject; which may be a human subject, and combining the assessment with the analysis of microvesicles.

In some embodiments, a patient sample, such as a serum sample, is analyzed for the presence of microvesicles, which may be exosomes or EVs that contain markers of interest. In particular embodiments, the analysis is flow cytometry with the methods of the invention. Markers of interest include radiation specific markers, tumor specific markers, pathogen specific markers, and immune cell markers, including antigen presenting cells such as dendritic cell markers, and the like. Assessment in a patient allows improved care, where patients classified according to responsiveness can be treated with an appropriate agent. Patients can be classified upon initial presentation of symptoms, and can be further monitored for status over the course of the disease to maintain appropriate therapy, or can be classified at any appropriate stage of disease progression. A therapeutic regimen (such as surgery, pharmaceutical treatments or radiation therapy) may be selected and/or administered based on the analysis. In an embodiment, the method further comprises determining a treatment course for the subject based on the analysis.

More broadly, the molecular nanotags can be used to characterize a phenotype of an individual by analyzing a vesicle such as a membrane vesicle or EV. The phenotype can be any observable characteristic or trait of a subject, such as a disease or condition, a disease stage or condition stage, susceptibility to a disease or condition, prognosis of a disease stage or condition, a physiological state, or response to therapeutics. A phenotype of disease can result from a subject's gene expression as well as the influence of environmental factors and the interactions between the two, as well as from epigenetic modifications to nucleic acid sequences. The phenotype in the subject can be characterized by obtaining a biological sample from the subject and analyzing one or more vesicles from the sample. For example, characterizing a phenotype for a subject or individual may include detecting a disease or condition (including pre-symptomatic early stage detecting), determining the prognosis, diagnosis, or theranosis of a disease or condition, or determining the stage or progression of a disease or condition. Characterizing a phenotype can also include identifying appropriate treatments or treatment efficacy for specific diseases, conditions, disease stages and condition stages, predictions and likelihood analysis of disease progression, particularly disease recurrence, metastatic spread or disease relapse. A phenotype can also be a clinically distinct type or subtype of a condition or disease, such as a cancer or tumor. Phenotype determination can also be a determination of a physiological condition, or an assessment of organ distress or organ rejection, such as post-transplantation.

The analysis of vesicles can also extend to determination of a biosignature to predict whether a subject is likely to respond to a treatment for a disease or disorder. Characterizing a phenotype includes predicting the responder/non-responder status of the subject, wherein a responder responds to a treatment for a disease and a non-responder does not respond to the treatment. Vesicles can be analyzed in the subject and compared to vesicle analysis of previous subjects that were known to respond or not to a treatment. If the vesicle biosignature in a subject more closely aligns with that of previous subjects that were known to respond to the treatment, the subject can be characterized as a responder to the treatment. Similarly, if the vesicle biosignature in the subject more closely aligns with that of previous subjects that did not respond to the treatment, the subject can be characterized as a non-responder to the treatment. The treatment can be for any appropriate disease, disorder or other condition. The method can be used in any disease setting where a vesicle biosignature that correlates with responder/non-responder status is known. When a biosignature indicates the subject is a responder to a particular eatment, that treatment can be administered to that subject.

In some examples, a flow cytometry device method disclosed in U.S. Pat. No. 9,739,700 or Yang et al., *Anal. Chem.*, 81:2555-63, 2009) (both incorporated by reference) is used.

Example 9

Examples of Disease Targets for Characterizing Disease

Cell-derived vesicles, in particular extracellular vesicles (EVs) such as microparticles (MPs) and microvesicles and exosomes, are useful to detect disease. Additional information about extracellular vesicle profiling and their use as potential disease-specific markers can be found, for example, in Julich et al., *Front. Immunol.* 5:413, 2014, which is incorporated by reference. Known MP/MV profiles of indicated diseases and MP/MV markers include the following taken from Julich et al.:

| Disease | MP/MV parental cell | MP/MV surface markers | Sample kind | Reference |
| --- | --- | --- | --- | --- |
| Meningococcal sepsis | CD4 T-Lymphocytes | Annexin V + CD4 | Plasma | (28) |
| | CD8 T-Lymphocytes | Annexin V + CD8 | | |
| | Monocytes | Annexin V + CD14 | | |
| | B-Lymphocytes | Annexin V + CD20 | | |
| | Platelets | Annexin V + CD61 | | |
| | Endothelial cells | Annexin V + CD62e | | |
| | Granulocytes | Annexin V + CD66b | | |
| | Erythrocytes | Annexin V + Glycophorin A | | |
| Atherosclerosis | CD4 T-Lymphocytes | Annexin V + CD4 | Atherosclerotic plaques | (29) |
| | Monocytes | Annexin V + CD14 | | |
| | Granulocytes | Annexin V + CD66b | | |
| | Endothelial cells | Annexin V + CD144 | | |
| | Red blood cells | Annexin V + CD235a | | |
| Dermatomyositis | T-Lymphocytes | Annexin V + CD3 | Plasma | (21) |
| | Monocytes/Macrophages | Annexin V + CD14 | | |
| | B-Lymphocytes | Annexin V + CD19 | | |
| Arthritis | T-Lymphocytes | Annexin V + CD3 | Synovial fluid | (17) |
| | Monocytes/Macrophages | Annexin V + CD14 | | |
| | Neutrophils | Annexin V + CD15 | | |
| | Platelets | Annexin V + CD41 | | |

-continued

| Disease | MP/MV parental cell | MP/MV surface markers | Sample kind | Reference |
|---|---|---|---|---|
| Malaria | T-Lymphocytes | Annexin V + CD3 | Plasma | (19) |
| | Monocytes | Annexin V + CD11b | | |
| | Platelets | Annexin V + CD41 | | |
| | Endothelial cells | Annexin V + CD105 + CD51 | | |
| | Red blood cells | Annexin V + CD235a | | |
| Chronic hepatitis C | CD4 T-Lymphocytes | Annexin V + CD3 | Serum | (6) |
| | CD4 T-Lymphocytes | Annexin V + CD4 | | |
| | CD8 T-Lymphocytes | Annexin V + CD8 | | |
| | Monocytes | Annexin V + CD14 | | |
| | Neutrophils | Annexin V + CD15 | | |
| | Platelets | Annexin V + CD41 | | |
| Chronic hepatitis C vs. non-alcoholic steatohepatitis | CD4 T-Lymphocytes | Annexin V + CD4 | Serum | (12) |
| | CD8 T-Lymphocytes | Annexin V + CD8 | | |
| | Monocytes | Annexin V + CD14 | | |
| | Neutrophils | Annexin V + CD15 | | |
| | Platelets | Annexin V + CD41 | | |
| | iNKT cells | Annexin V + Valpha24/Vbeta11 | | |

Additional information about the role of extracellular vesicles in inflammatory diseases is provided in Buzas et al., *Nature Reviews Rheumatology* 10:356-364 (2014), which is incorporated by reference.

Tumor cell derived EVs transmit oncogenic signals to other tumor cells in an autocrine/paracrine manner These EVs carry molecules that can promote tumor cell proliferation, migration, invasion, and metastasis. Of note, EVs can enable the noncanonical secretion of molecules that are otherwise not secreted, such as membrane proteins. Moreover, recent studies have revealed that EV miRNAs secreted by tumor cells also contribute to cancer progression and/or promote host protection. Specific EVs in body fluids that can serve as molecular nanotag targets have been summarized in Katsuda et al., *Proteomics* 14: 412-425 (2014), doi 10.1002/pmic.201300389, which is incorporated by reference herein.

In particular examples, the targets can be biomarkers or biosignatures of prostate cancer, as described in the incorporated U.S. Patent Publication No. 20140162888. For example, microRNAs (miRs) may be used to study or differentiate between BPH and prostate cancer. The miRs can be isolated directly from a patient sample, and/or vesicles derived from patient samples can be analyzed for miR payload contained within the vesicles. The sample can be a bodily fluid, including semen, urine, blood, serum or plasma, or a tissue or biopsy sample. A number of different methodologies are available for detecting miRs as described herein. in some embodiments, one or a combination of the following biomarker targets can he used for such purposes. miRs that distinguish BPH and PCa can be overexpressed in BPH samples as compared to PCa samples, including without limitation one or more of: hsa-miR-329, hsa-miR-30a, hsa-miR-335, hsa-miR-152, hsa-miR-151-5p, hsa-miR-200a and hsa-miR-145. Alternately, miRs that distinguish BPH and PCa can be overexpressed in PCa samples versus BPH samples, including without limitation one or more of: hsa-miR-29a, hsa-miR-106b, hsa-miR-595, hsa-miR-142-5p, hsa-miR-99a, hsa-miR-20b, hsa-miR-373, hsa-miR-502-5p, hsa-miR-29b, hsa-miR-142-3p, hsa-miR-663, hsa-miR-423-5p, hsa-miR-15a, hsa-miR-888, hsa-miR-361-3p, hsa-miR-365, hsa-miR-199a-3p, hsa-miR-181a, hsa-miR-19a, hsa-miR-125b. hsa-miR-760, hsa-miR-7a, hsa-miR-671-5p, hsa-miR-7c, hsa-miR-1979, and hsa-miR-103.

In particular examples, one or more of the following circulating biomarkers from U.S. Patent Publication No. 2014016288 may be targeted in microvesicles for assessing a prostate. disorder, and identifying biomarkers that can be usefully distinguished on microvesicles: BCMA, CEACAM-1, HVEM, IL-1 R4, IL-10 Rh, Trappin-2, p53, hsa-miR-103, hsa-miR-106b, hsa-miR-10b, hsa-miR425b, hsa-miR-142-3p, hsa-miR-142-5p, hsa-miR445, hsa-miR-151-5p, hsa-miR-152, hsa-miR-15a, hsa-miR-18 hsa-miR-1979, hsa-miR-199a-3p, hsa-miR-19a, hsa-miR-200a, hsa-miR-20b, hsa-miR-29a, hsa-miR-29b, hsa-miR-30a, hsa-miR-329, hsa-miR-335, hsa-miR-361-3p, hsa-miR-365, hsa-miR-373, hsa-miR-423-5p, hsa-miR-502-5p, hsa-miR-595, hsa-miR-663, hsa-miR-671-5p, hsa-miR-760, hsa-miR-7a, hsa-miR-7c, hsa-miR-888, hsa-miR-99a, and a combination thereof. The one or more circulating biomarkers can be selected from the following: hsa-miR-100, hsa-miR-1236, hsa-miR-1296, hsa-miR-141, hsa-miR-146b-5p, hsa-miR-17*, hsa-miR-181a, hsa-miR-200b, hsa-miR-20a*, hsa-miR-23a*, hsa-miR-331-3p, hsa-miR-375, hsa-miR-452, hsa-miR-572, hsa-miR-574-3p, hsa-miR-577, hsa-miR-582-3p, hsa-miR-937, miR-10a, miR-134, miR-141, miR-200b, miR-30a, miR-32, miR-375, miR-495, miR-564, miR-570, miR-574-3p, miR-885-3p, and a combination thereof. Further still, the one or more circulating biomarkers can be selected from the following: hsa-let-7b, hsa-miR-107, hsa miR 1205, hsa-miR-1270, hsa-miR-130b, hsa-miR-141, hsa-miR-143, hsa-miR-148b*, hsa-miR-150, hsa-miR-154*, hsa-miR-181a*, hsa-miR-181a-2*, hsa-miR-18a*, hsa-miR-19b-1*, hsa-miR-204, hsa-miR-2110, hsa-niiR-215, hsa-miR-217, hsa-miR-219-2-3p, hsa-miR-23b*, hsa-miR-299-5p, hsa-miR-301a, hsa-miR-301a, hsa-miR-326, hsa-miR--331-3p, hsa-miR-365*, hsa-miR-373*, hsa-miR-424, hsa-miR-424*, hsa-miR-432, hsa-miR-450a, hsa-miR-451, hsa-miR-484, hsa-miR-497, hsa-miR-517*, hsa-miR-517a, hsa-miR-518f, hsa-miR-574-3p, hsa-miR-595, hsa-miR-617, hsa-miR-625*, hsa-miR-628-5p, hsa-miR-629, hsa-miR-634, hsa-miR-769-5p, hsa-miR-93, hsa-miR-96. The circulating biomarkers can be one or more of hsa-miR-1974, hsa-miR-27b, hsa-miR-1.03, hsa-miR-146a, hsa-miR-22, hsa-miR-382, hsa-miR-23a, hsa-miR-376c, hsa-miR-335, hsa-miR-142-5p, hsa-m1R-221, hsa-miR-142-3p, hsa-miR-151-3p, hsa-miR-21 and hsa-miR-16. In an embodiment, the circulating biomarkers comprise one or more of CD9, PSMA, PCSA, CD63, CD81, B7H3, IL 6, OPG-13, IL6R, PA2G4, EZH2, RUNX2, SERPINB3, and EpCam. The biomarkers can comprise one or more of FOX01A, SOX9, CLNS1A, PTGDS, XPOI, LETMDL RAD23B, ABCC3, APC, CHES1, EDNRA, FRZB. HSPG2, and TMPRSS2_ETV1 fusion. See WO2010056993, which application is incorporated by reference herein in its entirety.

In another embodiment, the circulating biomarkers comprise one or more of A33, a33 n15, AFP, ALA, ALIX, ALP, AnnexinV, APC, ASCA, ASPH (246-260), ASPH (666-680), ASPH (A-10), ASPH (D01P), ASPH (D03), ASPH (G-20), ASPH(H-300), AURKA, AURKB, B7H3, B7H4, BCA-225, BCNP1, BDNF, BRCA, CA125 (MUC16), CA-19-9, C-Bir, CD1.1, CD10, CD174 (Lewis y), CD24, CD44, CD46, CD59 (MEM-43), CD63, CD66e CEA, CD73, CD81, CD9, CDA, CDAC1 1a2, CEA, C-Erb2, C-erbB2, CRMP-2, CRP, CXCL12, CYFRA21-1, DLL4, DR3, EGFR, Epcam, EphA2, EphA2 (H-77), ER, ErbB4, EZH2, FASL, FRT, FRT c.f23, GDF15, GPCR, GPR30, Gro-alpha, HAP, HBD 1, HBD2, HER 3 (ErbB3), HSP, HSP70, hVEGFR2, iC3b, IL6 Unc, IL-1B, IL6 Unc, IL6R, IL8, IL-8, INSIG-2, KLK2, L1CAM, LAMN, LDH, MACC-1, MAPK4, MART-1, MCP-1, M-CSF, MEG-E8, MIC1, MIF, MIS RII, MMG, MMP 26, MMP7, MMP9, MS4A1, MUC1, MUC1 seq1, MUC1 seq11A, MUC17, MUC2, Ncam, NGAL, NPG-PINPFF2, OPG, OPN, p53, p53, PA2G4, PBP, PCSA, PDGFRB, PGP9.5, PIM1PR (B), PRL, PSA, PSMA, PSME3, PTEN, R5-CD9 Tube 1, Reg IV, RUNX2, SCRN1, seprase, SERPINB3, SPARC, SPB, SPDEF, SRVN, STAT 3, STEAP1, TF (FL-295), TFF3, TGM2, TIMP-1, TIMP1, TIMP2, TMEM211, TMPRSS2, TNF-alpha, Trail-R2, Trail-R4, TrKB, TROP2, Tsg 101, TWEAK, UNC93A, VEGF A, and YPSMA-1. Any combination of these markers can be used in a biosignature to assess a prostate cancer. The circulating biomarkers can be associated with vesicles, e.g., vesicle surface markers or vesicle payload.

Example 10

Detection of EVs Labeled with Quantum Dots

The disclosed molecular nanotags can be used to detect extracellular vesicles (EVs). Molecular nanotags composed of a Qdot with a streptavidin linker and anti-PSMA were used to detect EVs from prostate cancer cells. Molecular nanotags composed of a Qdot with a streptavidin linker (SA-Qdot) and no PSMA biotin were used as a negative control. Prostate cancer cell line EVs were concentrated using a 100 kDa MW Pall Jumbosep filtration device, with $1\times10^{11}$ EVs then being labelled with 10 mM fluorophore CFSE before being purified from residual CFSE using size exclusion chromatography. EVs were incubated with the anti-PSMA-IgG1-Biotin antibody, before residual antibody was removed using size exclusion chromatography. The EV-bound anti-PSMA-IgG1-Biotin antibody was then labelled with either QDot 625-streptavidin, 40 nm gold streptavidin, 40 nm silver-streptavidin, or PE-streptavidin . The resulting labeled EVs were then detected using flow cytometry with thresholds set on either 488 nm or 561 nm scatter channels, a low flow rate, and the following detectors: 405 nm SSC, 488 nm, 561 nm SSC, 640 nm SSC, PE, FITC, and BV605.

As shown in FIG. 18, molecular nanotags composed of a Qdot with a streptavidin linker (SA-Qdot) and PSMA (CFSE+PSMA-SA-QD+EVs) could to detect EVs from prostate cancer cells, see upper right quadrant. Unbound QDots can be seen in the upper left quadrant, and CFSE EVs can be seen in the lower right quadrant. While not all of the CFSE EVs have shifted from the lower right to the upper right quadrant, it is most likely due to a combination of the instrument's fluorescent resolution, and not having the optimal filter for QDot 625.

Example 11

Detection of EVs Labeled with Metal Nanotags

The disclosed molecular nanotags can be used to can be used to detect EVs. Molecular nanotags composed of streptavidin coated silver or gold, with an anti-PSMA-IgG-biotin ligand (or other PSMA-binding ligands, such as A9g-TEG-biotin) were used to detect EVs derived from PSMA-expressing prostate cancer cells. Prostate cancer cell derived EVs were labelled with the fluorophore CFSE, with residual CFSE being removed with size exclusion chromatography. The resulting EVs were incubated with the nanotags. The resulting labeled EVs were then detected using flow cytometry, using 488 nm and 561 nm ss detectors. For details on method see Morales-Kastresana et al., *Scientific Reports*, 7:1878, 2017, herein incorporated by reference. Size exclusion chromatography was used to separate small molecules and/or antibodies from macromolecular structures, such as molecular nanotags or EVs with or without bound labels. Specifically, NAP5 or sephadex G25-type columns were used to separate unbound small molecules, such as nucleic acids and PSMA-binding molecules, as shown in FIG. 10B or 10C, from macromolecular structures, including molecular nanotags with core structures larger than 15 nm. Imtermediate resolution size exclusion chromatography was performed with Sepharose-2B or Seppharose-4B-based resins, and high resolution size exclusion chromatography was performed with FPLC, using high resolution resins, such as but not limited to Sepharose 6 Increase. nanoFACS high resolution flow cytometry was performed as described in Morales-Kastresana et al., *Scientific Reports*, 7:1878, 2017.

Figure 19A:
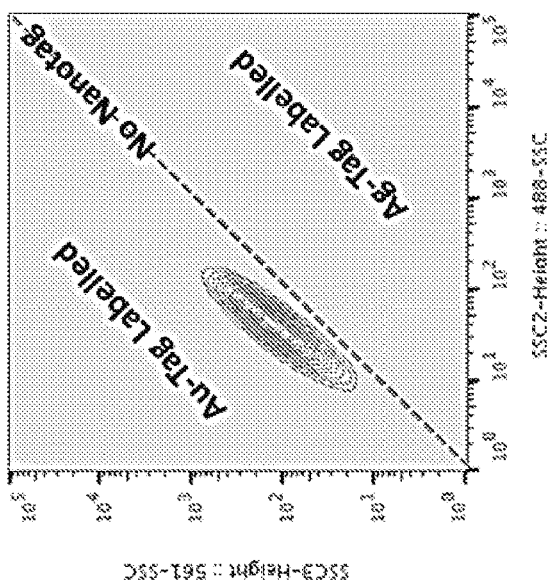
FIGS. 19A-19C illustrate detection of (A) fluorescently positive (CFSE+) extracellular vesicles (EVs), (B) CFSE+ EVs attached to an Au nanotag, causing a shift in 488 nm scatter intensity of the CFSE+ EV events. (C) shows CFSE+ EVs stained with an Ag nanotag, causing a shift in the 561 nm scattering intensity of EVs.
Figure 19B:
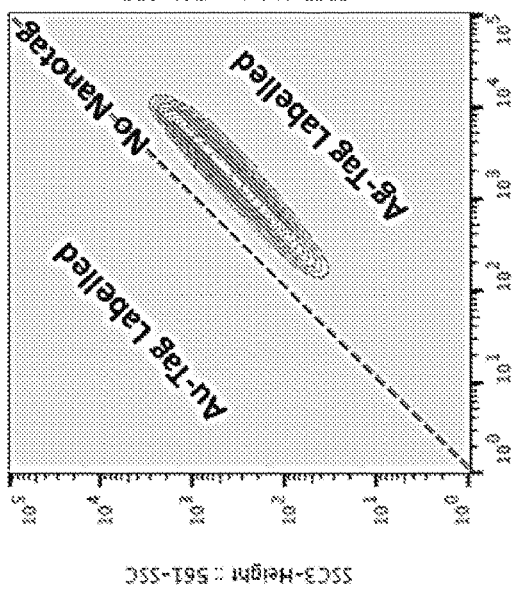
Figure 19C:
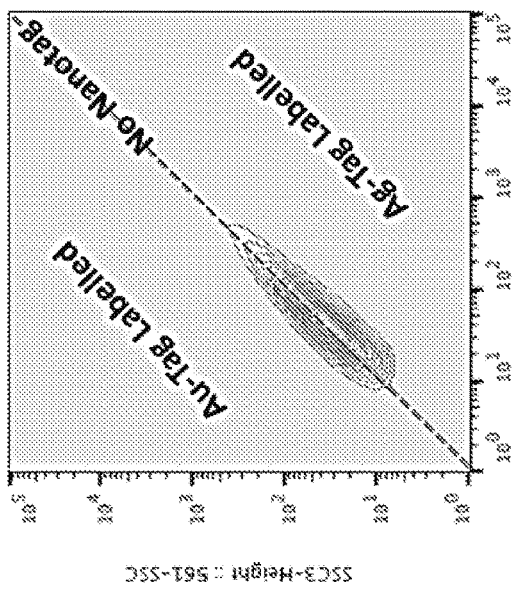

As shown in FIG. 19A fluorescently positive (CFSE+) EVs detected using the 488 nm and 561 nm scattering parameters lie on the dotted line (y=x). FIG. 19B shows 40 nm-streptavidin-silver nanoparticles and shows how the population would shift upwards in 488 nm scatter, if labelled with these silver nanotags. Conversely, FIG. 19C shows 40 nm-streptavidin-gold nanoparticles and shows how the population would shift upwards in 561 nm scattering, if labelled with these silver nanotags.

Example 12

Detection of Nanoparticles

Nanoparticles composed of silver, silver and gold, or polystyrene were detected using a Astrios and a Symphony flow cytometer.

Figure 20:
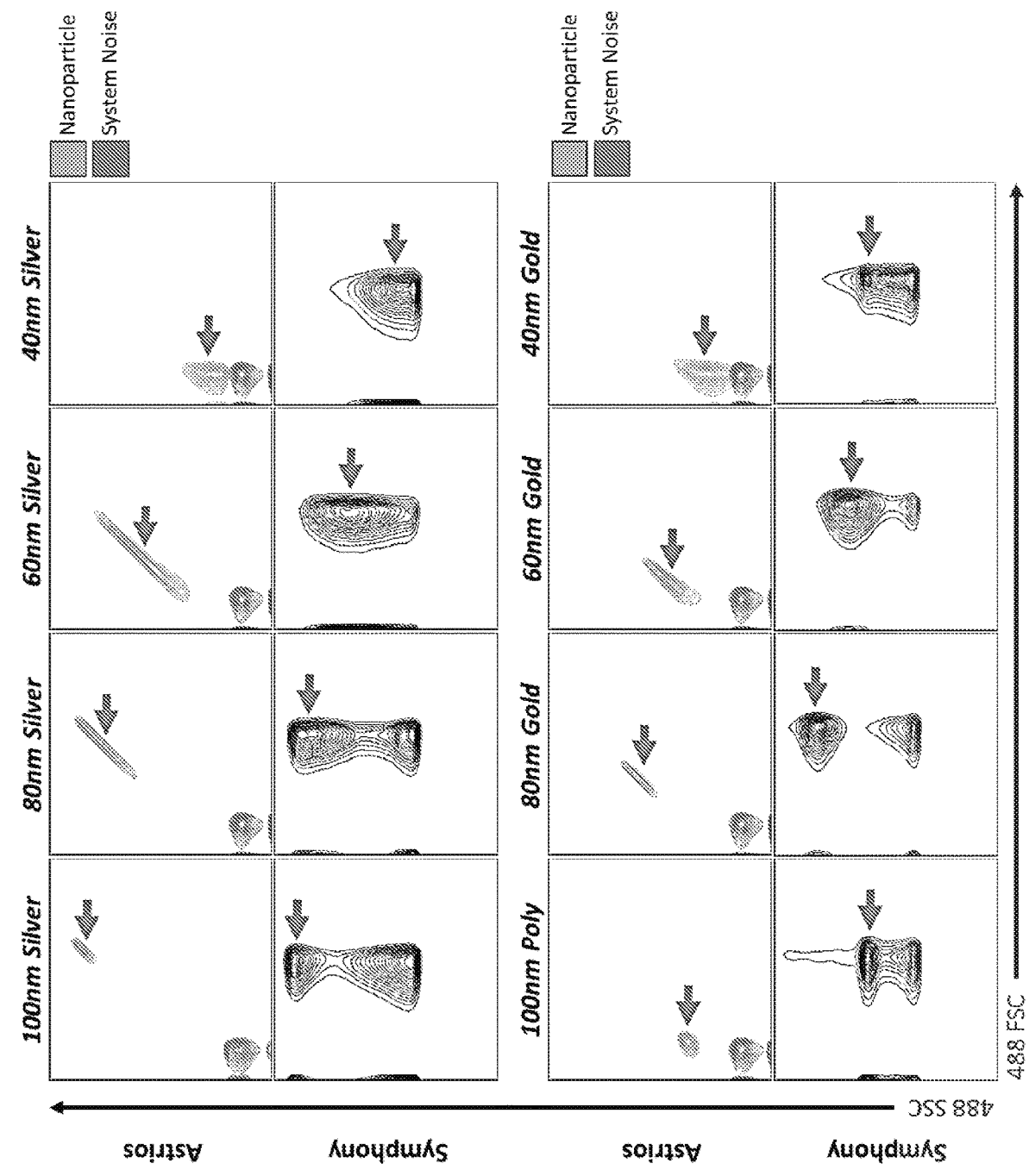
FIG. 20 illustrates raw data obtained using an Astrios instrument or a Symphony instrument to detect 40 nm, 60 nm, or 80 nm, nanoparticles composed of gold and 100 nm nanoparticles composed of polystyrene.

FIG. 20 shows the relative scatter power of gold, silver, and polystyrene particles (arrowhead) against the instruments baseline noise. It can be seen that particles down to 40 nm, composed of gold or silver, can be detected without being bound to any on 488 SSC on the Astrios instrument. This is also true of the FACS Symphony instrument. Because the nanoparticles can be detected individually, they can be quantified individually. Thus, the nanoparticles can be used as individual, non-aggregated, non-multimerized individual labels.

Example 13

Generation, Labeling, and Detection of EVs

Figure 21:
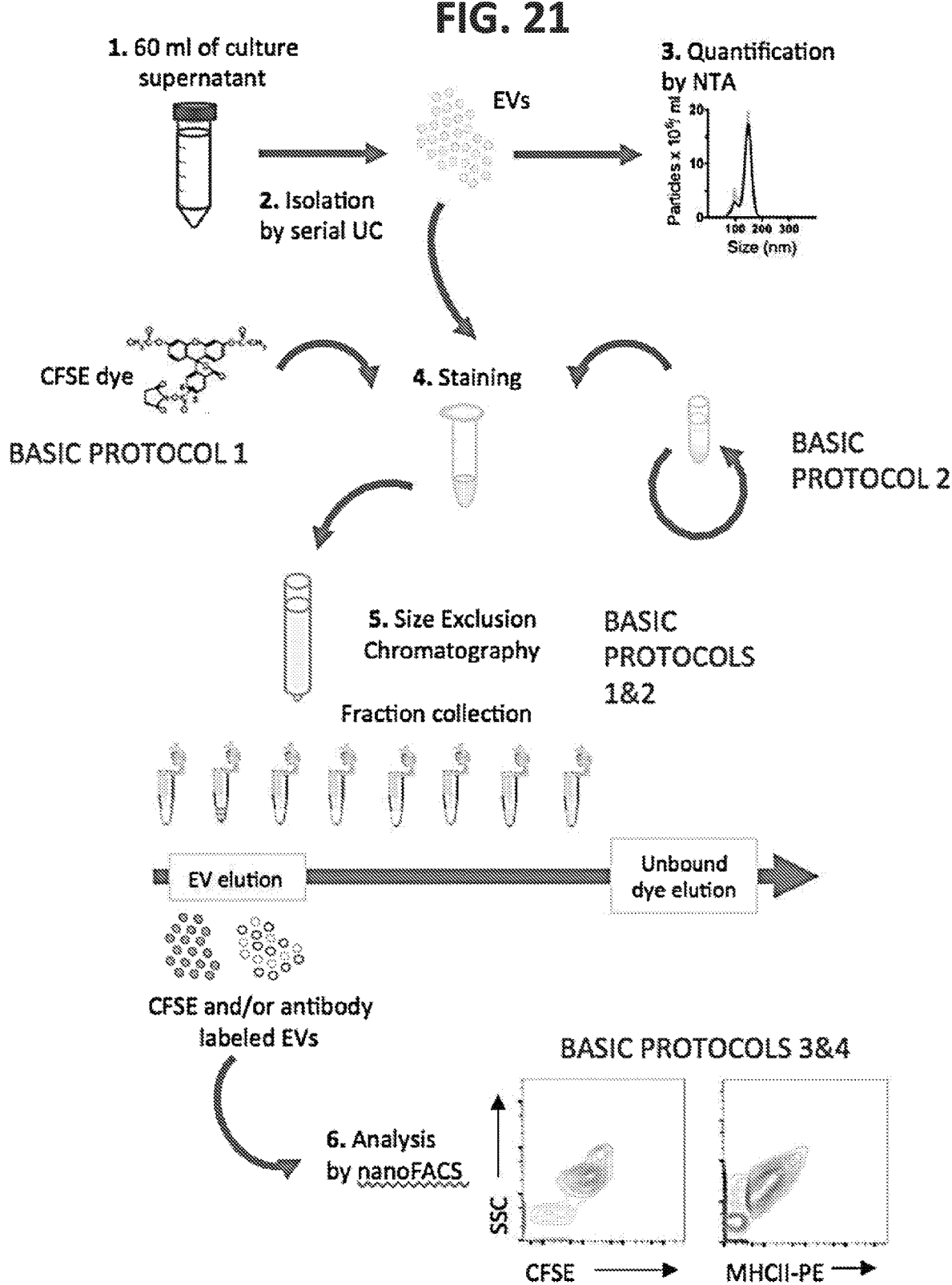
FIG. 21 illustrates a protocol for isolating, labeling and detecting EVs.

FIG. 21 provides an overview of a method to generate, label and detect EVs. This method permits the production and subsequent quantification/analysis of individual nanomaterials.

Cells, which can be primary cells, such as those obtained from a tumor, or tissue culture cells, are used to generated a supernatant. For example, cells are grown in EV-depleted medium and EVs obtained, for example by serial ultracentrifugation (UC) or by using immunogenic capture (for exemplary details see Morales-Kastresana et al., *Scientific Reports*, 7:1878, 2017, herein incorporated by reference). EV-bound molecular nanotags can be removed following flow cytometric analysis, if desired, by separation using a photocleavable linker between the armor (see 12 of FIG. 1) and ligand-binding element (see 14 of FIG. 12), or by elution based on the ligand-binding properties of (see 14 of FIG. 1A, such as that if the ligand-binding element binds to, for example, phosphatidylerine in a calcium dependent manner, then EDTA may be used to separate the molecular nanotags from the EVs, or is streptavidin:biotin biding is used to link the molecular nanotag to the EV-binding ligand, then the molecular nanotags may be removed by adding desthiobiotin (Hirsch et al, *Analytical Chemistry*, 2002). The resulting EVs can be quantified by nanoparticle tracking analysis (NTA). In some examples, the methods of Mehdiani et al. (*J. Vis. Exp.* (95), e50974, doi:10.3791/50974, 2015, herein incorporated by reference), are used to prepare EVs.

The isolated or purified EVs can be labeled, for example with a fluorophore and a molecular nanotag provided herein. For example, EVs can be labeled with CFSE dye using the methods disclosed in Morales-Kastresana et al., *Scientific Reports*, 7:1878, 2017 (herein incorporated by reference).

The EVs can also be detectably labeled with a molecular nanotag provided herein, such as one that includes a gold, silver, or both, nanoparticle, and a first binding partner (e.g., an antibody, nucleic acid molecule, or ligand) specific for a second binding partner on the EV (e.g., an EV membrane protein or a tumor antigen). For example, the nanotag ($1\times10^9$) and the EVs ($1\times10^9$) can be incubated for 30 minutes at 4° C.

The resulting labeled EVs can be subjected to size exclusion chromatography, and fractions collected. This step can be used to remove unbound nanotags and unincorporated fluorophore.

The eluted EVs, which now include one or more molecular nanotags (if the target is present on the EV) and in some examples also a fluorophore, can be analyzed using flow cytometry using the methods provided herein.

Example 14

The Spectral Properties of Nanotag Compositions

A single molecular nanotag with optical properties having a high elastic scattering power or or a component with high inelastic scattering (fluorescence or Raman scattering) that is quantifiable individually, allows detection and sorting of EVs or other nanomaterials based on binding to a single epitope of interest. Phenotyping subsets is a powerful tool that requires the labelling of more than one epitope at a time. In order to label more than one epitope simultaneously, the use of a second, or more, nanotag with distinctive optical properties to distinguish it from the first would be beneficial.

Figure 6A:
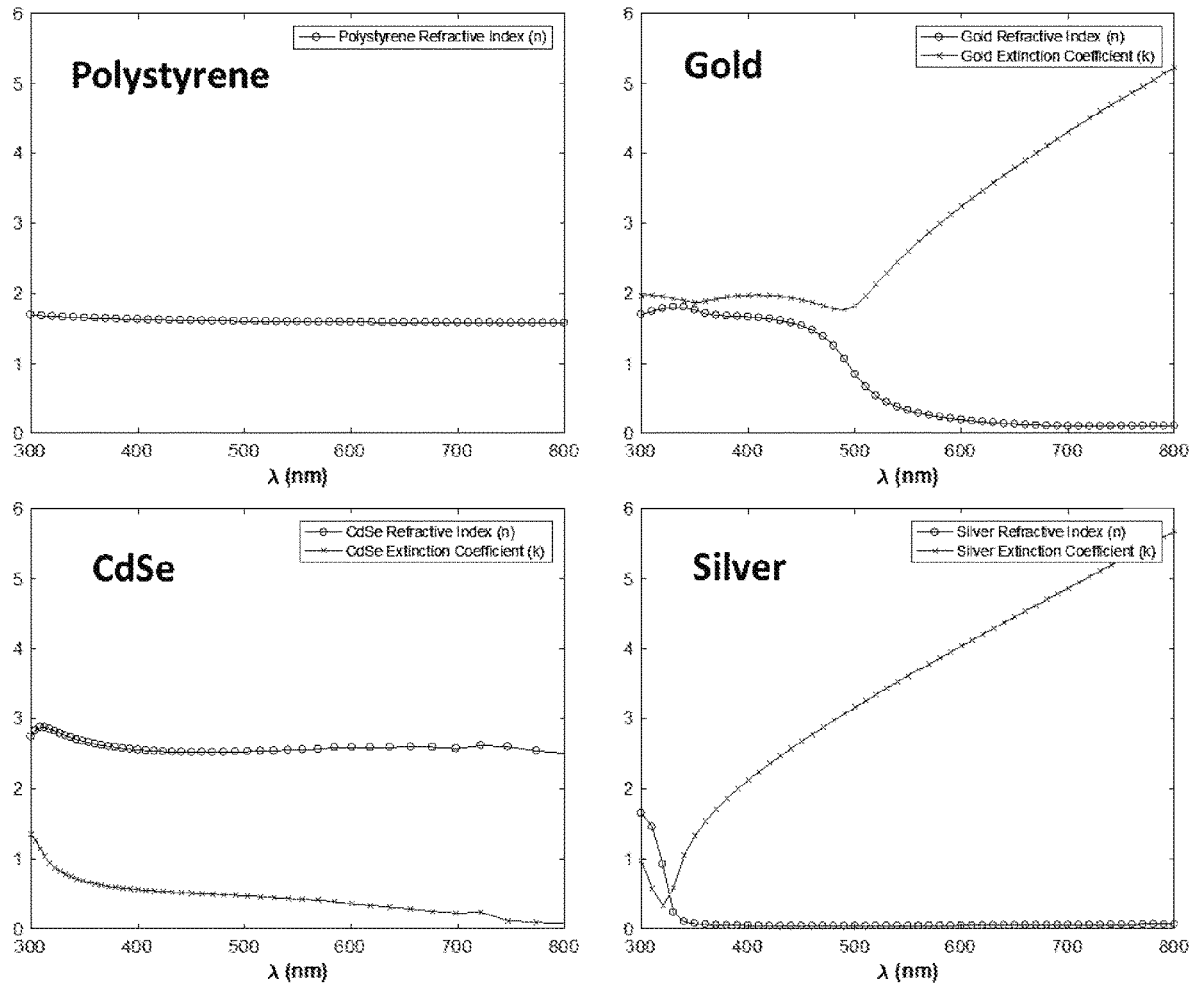
Figure 6B:
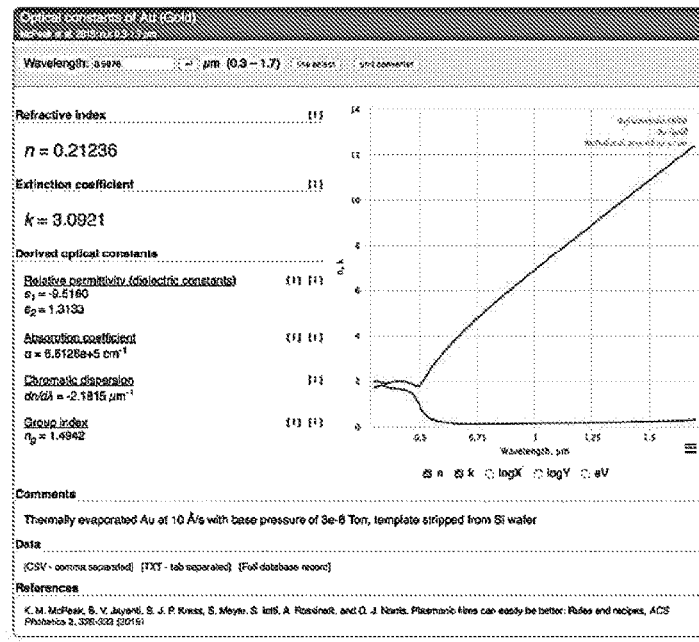

It can be seen that different metals have distinctive dispersion properties in the UV-visible spectrum with respective to refractive index and extinction coefficient (FIG. 6A). These optical properties are available from online databases such as RefractiveIndex.info (FIG. 6B).

Using Mie theory it is possible to approximate the scattering cross-section of spheres using these optical properties and therefore deduce how multiple particles can be used simultaneously due to having distinctive peaks or troughs in their scattering profile at different wavelengths. This method is useful to predict the ability of a flow cytometer with multiple side scatter (SSC) detectors at different laser wavelengths, such as by an AstriosEQ e.g. 405 nm SSC, 488 SSC, 561 SSC, 640 SSC, to detect particles of different diameter and composition. Characteristic multi-wavelength side scatter profiles for different nanotags can be compared with detected side scatter values across a range of wavelengths, including discrete wavelengths or a continuous wavelength range or ranges. Thus, monochromatic and broadband illumination sources can be used to generate side scatter at a target that includes nanotags.

This modelling technique was applied to different materials, including gold, silver, polystyrene, platinum, titanium dioxide, iron oxide, and copper, FIGS. 16A-16E. As shown in FIGS. 18A-18E, smaller particles, approximately 20-60 nm spheres, resulted in distinctive spectral peaks and troughs, such as gold and silver. In addition, it can be seen that metals, such as gold, copper, and silver, are predicted to enhance particle detection (e.g., as compared to polystyrene).

As shown in FIG. 22A-22B, a 100 nm polystyrene sphere is detectable on conventional flow cytometers, such as the FACS Symphony, and has a scattering cross-section of $\sim 1\times10^{-16}$ $m^2$ $sr^{-1}$ across wavelengths of 400-800 nm. A 20 nm Ag sphere also has a scattering cross-section of $\sim 1\times10^{-16}$ $m^2$ $sr^{-1}$ at an illumination wavelength of 380 nm and a 40 nm au sphere having a scattering cross-section of $\sim 1\times10^{-16}$ $m^2$ $sr^{-1}$ at an illumination wavelength of 532 nm.

Figure 17A:
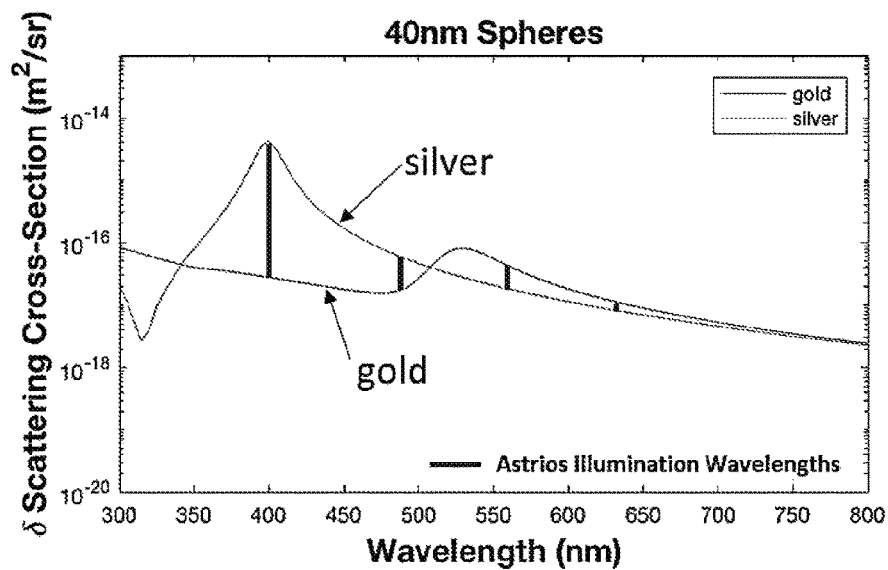
FIG. 17C illustrates based on a mathematical model how gold and silver nanoparticles can be distinguished from one another using appropriate ss detectors.
Figure 17B:
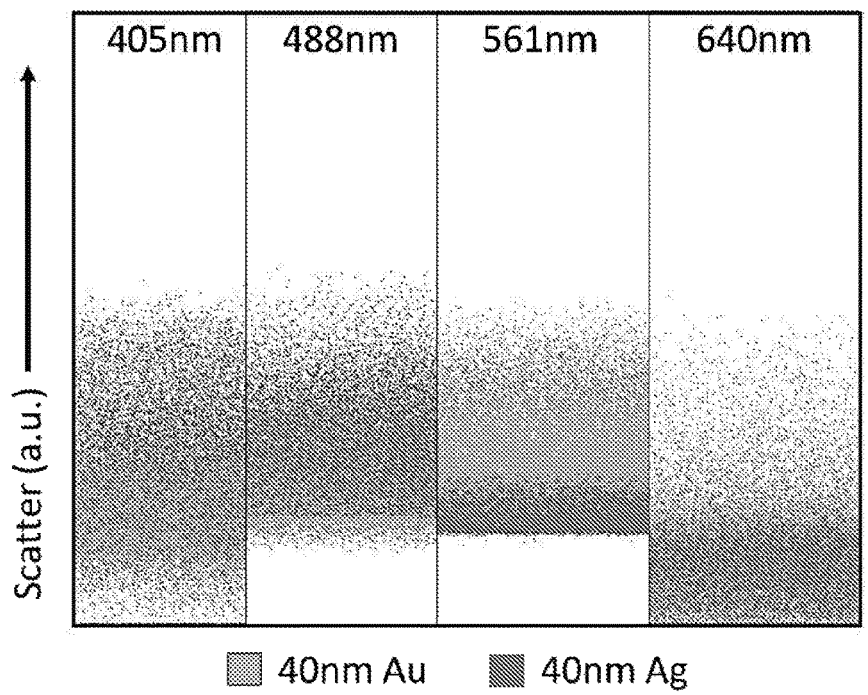
Figure 17C:
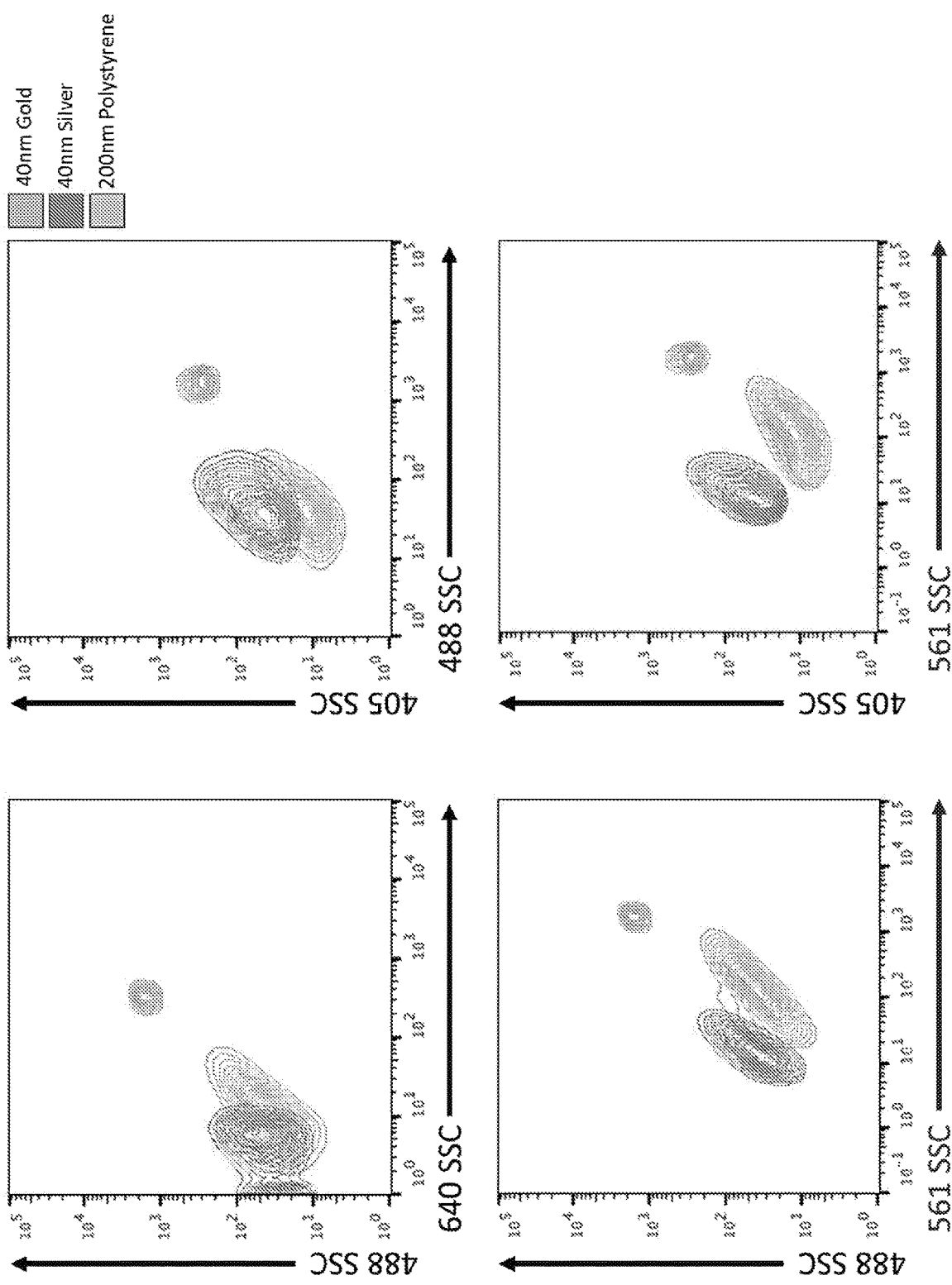

These intrinsic scattering properties of particles with different compositions allow a spectral approach to labelling as fluorescence is used, however by instead utilizing scattering. For example in FIG. 16B, at an illumination wavelength of 405 nm, the collected light scattering of 40 nm silver particles is ~100 times higher than 40 nm gold particles. However, at an illumination wavelength of 561 nm, the collected light scattering of 40 nm gold particles is 5-10 times higher than that of 40 nm silver particles. This modelled data was validated by acquiring 40 nm silver and gold spheres at illumination wavelengths of 405, 488, 561, and 640 nm on an Astrios EQ instrument to evaluate how spectral scattering can be utilized (FIG. 17B). As the models predicted the collected scattering of 40 nm silver particles (red) was less on the 561 nm scatter channel compared (blue) with 40 nm gold, and the collected scatter of 40 nm silver particles was more than 40 nm gold on the 405 nm scatter channel.

Thus, based on the particular SSC detectors available on an instrument, it is possible to select an appropriate material from which to make a molecular nanotag described herein. For example, if an instrument has a 405 nm SSC detector, silver nanoparticles can be used; if an instrument has a 561 or 532 nm SSC detector, gold nanoparticles can be used, and so on Particular examples are shown in Table 1 below.

TABLE 1

Exemplary combinations of materials and ss detectors.

| Nanoparticle Material Example | Peak SS Detector Wavelength |
|---|---|
| Silver nanosphere | 350 to 500 nm, such as 405 nm |
| Gold nanospheres | 500 to 650 nm, such as 532 nm, 561 nm |
| Gold nanourchins | 650 to 800 nm, such as 700 nm |
| Silver and Gold | Intermediate to silver and gold, depending on ratio of composition |

In contrast, if a ss detector is used where there is little distinction between the signals for two or more nanoparticles, such as at 640 nm for gold and silver (see FIG. 17A), deconvolution can be used to determine the individual contribution of scatter (Fogarty and Warner, *Analytical Chemistry*, 53:259, 1981; Liu et al. *Photonics Research* 2:168-171, 2014), in the same manner that spectral deconvolution can be applied to fluorescence or Raman spectral data.

Additional information can be found in U.S. Provisional Application No. 62/575,988 filed Oct. 23, 2017, herein incorporated by reference.

Example 15

The Spectral Properties of Nanotag Compositions

Using mie theory to model the amount of light scatter by spherical particles and taking into account flow cytometer optics, it is possible to produce a model of the scatter-diameter relationship for a particular flow cytometer acquiring particles of different refractive indices, FIGS. 22A-22B.

Using the method of Welsh (Flow cytometer optimisation and standardisation for the study of extracellular vesicles as translational biomarkers, University of Southampton Doctoral Thesis, 209 pp, 2016) Astrios EQ and FACS Symphony flow cytometers were modelled fitting acquired polystyrene and silica particle data to modelled data. This method produces a very high correlation between acquired flow cytometry bead data and modelled bead data and allows on to infer the sensitivity of flow cytometry instruments for particles of low and variable refractive index such as extracellular vesicles, depicted in green in FIGS. 22A-22B.

Utilizing this method extracellular vesicle diameter limits of detection are approached for EVs with low refractive indices at approximately 150nm for the Astrios EQ and 200 nm for the Symphony (FIG. 22B). As the modal diameter of EVs tend to be in the 100 nm region, with subpopulation often appearing below 100 nm it highlights that most conventional flow cytometers are suboptimal for the detection of the full population of extracellular vesicles in biological samples using scatter, in the same way that most flow cytometers are not sufficiently sensitive to detect one fluorescein MESF equivalent (Nolan and Jones, *Platelets* 28:256-62, 2017; Morales-Kastresana et al., *Scientific Reports*, 7:1878, 2017)

Example 16

Analysis of EVs by Multiplexing

Fluorescent barcoding can be used to detect multiple different populations of beads using f flow cytometry. FIG. 23A shows data from a commercially available multiplex bead set for exosomes analysis. 38 different bead populations are characterized by each population having different amounts of red and green label, so that the bead populations are "barcoded," based on defined levels of red and green label (P1 and P2 parameters as shown). Each bead population also carries antibodies against a specific human epitope found on certain EVs, thereby providing a means to capture EVs with 38 different epitope specificities.

FIG. 23B shows that following capture of EVs from plasma with the 38 bead set (with binding capacity>100 EVs per bead), a staining antibody against a different EV epitope to identify 3 bead populations that were bound to EVs with that epitope. The beads in this example are 3 micron beads and detection of any bead as positive requires the presence of >100 detection antibody-bound fluorophores, based on MESF controls.

FIG. 23C shows the use of molecular nanotags, with our nanoFACS configuration, Molecular nanotags can be used to generate a multiplex EV analytical array that allow for single epitope and single EV sensitivity. Barcoding is enabled by incorporation of customized ratios of different fluorophores in the armor, while elastic scattering attributes of N different core types enable addition of N layers, where, for example, the use of gold and silver cores would comprise N=2 distinct core components, such that a molecular nanotag Array with 38 molecular nanotag with gold cores could be combined with 38 molecular nanotag with silver cores, with each of the 76 molecular nanotag types conjugated to molecule with specificity for one ligand, would enable detection of EVs with 76 different epitopes with single-epitope sensitivity for 76 different epitopes. In this manner, the distinctive scattering properties of different core materials based on size, material, or geometry, provides a means of expanding multiplex panels to not only include fluorescence-based barcoding, but also light scattering barcoding. Sorting populations of these molecular nanotags when they are bound to EVs allows multiplex sorting to perform downstream analyses, such as miRNA analysis.

FIG. 23D shows that the cargo of the different subsets of EVs captured by each type of molecular nanotag can interrogated. FIG. 23D shows a comparions of miRNA profiles of EVs sorted based on detection of PSMA on the EVs, versus the bulk EV population miRNA or miRNA of PSMA-negative EVs.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

The invention claimed is:

1. A method for detecting in a flow cytometer a single target molecule in a sample, comprising:
contacting the sample with a nanoscale molecular tag, wherein the nanoscale molecular tag comprises:
(i) a core nanoparticle with a diameter of 30-80 nm and wherein the core nanoparticle comprises a noble metal;
(ii) an optional shell surrounding the core wherein said shell is selected from the group consisting of a layer of gold, silver, or both, noble metals; or includes nucleic acids or PEG; and
(iii) an armor comprising a first portion and a second portion, wherein the first portion reduces the valency of the nanoparticle to only one functional binding site and is bound to the surface of the core nanoparticle, or if present, to the surface of the shell, and the second portion is not bound to the core nanoparticle or shell, and comprises a functionalized end with one binding site, wherein the functionalized end comprises a first binding partner that is capable of specifically binding to a second binding partner or a target ligand and wherein the first and second binding partners are, respectively, selected from:

benzylguanine and a SNAP-Tag;
benzylguanine and a CLIP-Tag;
biotin and streptavidin;
a single-stranded oligonucleotide and a complementary single-stranded oligonucleotide;
a single-stranded oligonucleotide and an aptamer;
DCFPyL and prostate specific membrane antigen (PMSA);
a receptor and a ligand;
a ligand and a receptor;
an antibody and an antigen; or
an antigen and an antibody;
wherein any one of, or any combination of, the core, the shell and the armor contribute to fluorescence, light scattering and/or ligand binding properties of the molecular tag that are detectable by microscopy or an instrument that measures fluorescence and/or light scattering intensity or power; and
wherein components (i) and (iii) or (i), (ii) and (iii) together provide the following functionalities:
(a) light scattering intensity or power of the assembled structure of components (i) and (iii) or (i), (ii), and (iii) is detectable above the specific level of the reference noise of the instrument detecting the light scattering intensity or power;
(b) fluorescence intensity has sufficient brightness for detection above the limit of detection for the instrument; and/or
(c) ligand specificity is conferred by a ligand binding component,
wherein the functionalized end of the nanoscale molecular tag specifically binds the target molecule if present in the sample; and
analyzing the sample using the instrument that measures light scattering intensity or power, wherein the instrument is configured for resolution of small particles to detect individual nanoscale molecular tags bound to the target molecule by detection of side scatter or forward light scatter or detection of fluorescence, or any combination thereof.

2. The method of claim 1, wherein the core nanoparticle is comprised of a nanomaterial having a high refractive index, surface geometry, or other attributes that contribute to light scattering properties that are detectable by the device that measures light scattering intensity or power.

3. The method of claim 1, wherein, a single assembled molecular nanotag is detectable with microscopy or the device that measures light scattering intensity or power.

4. The method of claim 1, wherein the core nanoparticle comprises gold or silver.

5. The method of claim 1, wherein cumulative optical properties of the components of the nanoscale molecular tag, result in a collected power greater than a detection device's limit of sensitivity ($Y_{limit}$) for one or more light scattering wavelengths, wherein the cumulative optical properties comprise one or more of refractive index, extinction coefficient, diameter, resonance, transmittance, and reflectivity.

6. The method of claim 1, wherein the constituent components have a parameter $N_{RAQD} = N_{Refractive\ index, Angular\ and\ Quantum\ properties,\ and\ Diameter}$, where $N_{RAQD}$ must be greater than the limit of detection ($Y_{limit}$) for one or more wavelengths using a device that measures light scattering intensity or power, wherein intensity or power is defined as a unit of power per unit area.

7. The method of claim 1, wherein the armor comprises a polymer.

8. The method of claim 7, wherein the polymer comprises phosphorothioate DNA molecule.

9. The method of claim 7, wherein the polymer has attributes for fluorescent or light scattering properties or both.

10. The method of claim 9, wherein the polymer contributes to the fluorescence, light scattering and/or ligand binding properties of the molecular tag.

11. The method of claim 1, wherein the antigen comprises a tumor-associated antigen.

12. The method of claim 1, wherein the antigen comprises a protein tag.

13. The method of claim 1, wherein the nanoscale molecular tag comprises a fluorophore.

14. The method of claim 1, wherein the sample is analyzed in the device that measures light scattering intensity or power using at least two angles of detection from respective side scatter channels.

15. The method of claim 14, wherein a first side scatter channel is used as a trigger and a second side scatter channel is used as a detector.

16. The method of claim 1, comprising detecting parallel subthreshold events.

17. The method of claim 1, wherein the sample is a biological sample.

18. The method of claim 17, wherein the biological sample comprises a biological membrane.

19. The method of claim 17, wherein the biological sample comprises extracellular vesicles.

20. The method of claim 1, wherein the target molecule comprises a tumor antigen.

21. The method of claim 20, wherein the tumor antigen comprises prostate specific membrane antigen (PSMA), epidermal growth factor receptor (EGFR), HER-2/neu, epithelial cell adhesion molecule (EpCAM), CD24, CD133, CD47, CD147, PD-L1, GPC-1, Muc-1, CD44, CD26, CD147, EpCAM, PSMA, or PD-L1.

22. The method of claim 1, wherein the core nanoparticle has a diameter of less than about 75 nm or less than about 40 nm.

* * * * *